(12) United States Patent
Lizardi

(10) Patent No.: US 6,632,609 B2
(45) Date of Patent: *Oct. 14, 2003

(54) UNIMOLECULAR SEGMENT AMPLIFICATION AND SEQUENCING

(75) Inventor: Paul M. Lizardi, Cuernavaca (MX)

(73) Assignee: Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/841,513

(22) Filed: Apr. 24, 2001

(65) Prior Publication Data

US 2002/0192649 A1 Dec. 19, 2002

Related U.S. Application Data

(63) Continuation of application No. 09/602,428, filed on Jun. 23, 2000, now Pat. No. 6,329,150, which is a continuation of application No. 08/754,681, filed on Nov. 21, 1996, now Pat. No. 6,143,495, which is a continuation-in-part of application No. 08/563,912, filed on Nov. 21, 1995, now Pat. No. 5,854,033.
(60) Provisional application No. 60/016,677, filed on May 1, 1996.

(51) Int. Cl.$^7$ .......................... C12Q 1/68; G01N 33/53; C12P 19/34; C07H 21/02; C07H 21/64
(52) U.S. Cl. .......................... 435/6; 435/7.1; 435/91.2; 536/23.1; 536/24.3
(58) Field of Search .................. 435/6, 7.1, 91.2; 536/23.1, 24.3

(56) References Cited

U.S. PATENT DOCUMENTS

| | | | |
|---|---|---|---|
| 4,748,111 A | 5/1988 | Dattagupta et al. ............ 435/7 |
| 4,883,750 A | 11/1989 | Whiteley et al. |
| 4,965,188 A | 10/1990 | Mullis et al. |
| 4,994,373 A | 2/1991 | Stavrianopoulos et al. |
| 5,001,050 A | 3/1991 | Blanco et al. |
| 5,130,238 A | 7/1992 | Malek et al. ................. 435/91 |
| 5,198,543 A | 3/1993 | Blanco et al. |
| 5,242,794 A | 9/1993 | Whiteley et al. |
| 5,273,638 A | 12/1993 | Konrad et al. .............. 204/299 |
| 5,328,824 A | 7/1994 | Ward et al. |
| 5,354,668 A | 10/1994 | Auerbach ................... 435/91.1 |
| 5,409,818 A | 4/1995 | Davey et al. |
| 5,427,930 A | 6/1995 | Birkenmeyer et al. ... 435/91.52 |
| 5,455,166 A | 10/1995 | Walker |
| 5,521,065 A | 5/1996 | Whiteley et al. |
| 5,591,609 A | 1/1997 | Auerbach ................... 435/91.2 |
| 5,614,389 A | 3/1997 | Auerbach ................... 435/91.2 |
| 5,629,158 A | 5/1997 | Uhlen .......................... 435/6 |
| 5,714,320 A | 2/1998 | Kool |
| 5,733,733 A | 3/1998 | Auerbach ..................... 435/6 |
| 5,854,033 A | 12/1998 | Lizardi ....................... 435/1.2 |
| 6,124,120 A | 9/2000 | Lizardi |
| 6,143,495 A | 11/2000 | Lizardi et al. ................ 435/6 |
| 6,183,960 B1 | 2/2001 | Lizardi |
| 6,210,884 B1 | 4/2001 | Lizardi |
| 6,280,949 B1 | 8/2001 | Lizardi |
| 6,287,824 B1 | 9/2001 | Lizardi |
| 6,316,229 B1 | 11/2001 | Lizardi et al. |
| 6,329,150 B1 * | 12/2001 | Lizardi |
| 6,344,329 B1 | 2/2002 | Lizardi |

FOREIGN PATENT DOCUMENTS

| | | |
|---|---|---|
| AU | 649066 | 5/1994 |
| EP | 0 128 332 A2 | 12/1984 |
| EP | 0 356 021 A2 | 2/1990 |
| EP | 0 439 182 B1 | 7/1991 |
| EP | 0 505 012 A2 | 9/1992 |
| EP | 0 667 393 A2 | 8/1995 |
| JP | 4262799 | 9/1992 |
| JP | 42 262 799 | 9/1992 |
| JP | 4304900 | 10/1992 |

(List continued on next page.)

OTHER PUBLICATIONS

Dynal, Technical Handbook, "Biomagnetic Techniques in Molecular Biology", Dynal A.S. (1995).
Prober, et al., Science 238:336–341 (1987).
Kimpton, et al., PCR Methods and Applications 3:13–22 (1993).

(List continued on next page.)

*Primary Examiner*—Ethan Whisenant
(74) *Attorney, Agent, or Firm*—Needle & Rosenberg, P.C.

(57) ABSTRACT

Disclosed are compositions and a method for amplification of and multiplex detection of molecules of interest involving rolling circle replication. The method is useful for simultaneously detecting multiple specific nucleic acids in a sample with high specificity and sensitivity. The method also has an inherently low level of background signal. A preferred form of the method consists of an association operation, an amplification operation, and a detection operation. The association operation involves association of one or more specially designed probe molecules, either wholly or partly nucleic acid, to target molecules of interest. This operation associates the probe molecules to a target molecules present in a sample. The amplification operation is rolling circle replication of circular nucleic acid molecules, termed amplification target circles, that are either a part of, or hybridized to, the probe molecules. A single round of amplification using rolling circle replication results in a large amplification of the amplification target circles. Following rolling circle replication, the amplified sequences are detected using combinatorial multicolor coding probes that allow separate, simultaneous, and quantitative detection of multiple different amplified target circles representing multiple different target molecules. Since the amplified product is directly proportional to the amount of target sequence present in a sample, quantitative measurements reliably represent the amount of a target sequence in a sample. Major advantages of this method are that a large number of distinct target molecules can be detected simultaneously, and that differences in the amounts of the various target molecules in a sample can be accurately quantified. It is also advantageous that the DNA replication step is isothermal, and that signals are strictly quantitative because the amplification reaction is linear and is catalyzed by a highly processive enzyme.

70 Claims, 43 Drawing Sheets

FOREIGN PATENT DOCUMENTS

| WO | WO91/080307 | 6/1991 |
|---|---|---|
| WO | WO 92/01813 | 2/1992 |
| WO | WO 94/24312 | 10/1994 |
| WO | WO 95/03432 | 2/1995 |
| WO | WO95/22623 | 8/1995 |
| WO | WO 95/22623 | 11/1995 |
| WO | WO 95/35390 | 12/1995 |
| WO | WO92/01813 | 2/1996 |
| WO | WO97/20948 | 6/1997 |
| WO | WO 97/42346 | 11/1997 |

OTHER PUBLICATIONS

Shumaker, et al., Human Mutation 8(4):346–354 (1996).

Aliotta, J.M., et al., "Thermostable Bst DNA polymerase lacks a 3'–5' proofreading exonuclease activity," *Genet. Anal.* 12:185–195 (1996).

Chetverina, H., et al., "Cloning of RNA molecules in vitro," *Nucleic Acids Research* 21:2349–2353 (1993).

Gerdes, M.G., et al., "Dynamic changes in the higher–level chromatin organization of specific sequences revealed by *in situ* hybridization in nuclear halos," *J. Cell Biol.* 126:289–304 (1994).

Guo, Z., et al., "Enhanced discrimination of single nucleotide polymorphisms by artificial mismatch hybridization," *Nature Biotechnology* 15:331–335 (1997).

Hacia, J.G., et al., "Detection of heterozygous mutations in BRCA 1 using high density oligonucleotide arrays and two–color fluorescence analysis," *Nature Genetics* 14:441–447.

Liu, D., et al., "Rolling circle DNA synthesis: Small circular oligonucleotides as efficient templates for DNA polymerases," *J. Am Chem. Soc.* 118:1587–1594 (1996).

Lockhart, et al., "Expression monitoring by hybridization to high–density oligonucleotide arrays," *Nature Biotechnology* 14:1675–1680 (1996).

Lukyanov, C., et al., "Molecule by molecule PCR amplification of complex DNA mixtures for direct sequencing: an approach to in vitro cloning," *Nucleic Acids Research* 20:1691–1696 (1996).

Luo, J., et al., "Improving the fidelity of T*hermus thermophilus* DNA ligase," *Nucl. Acids Res.* 24:3071–3078 (1996).

Maskos, U., et al., "Oligonucleotide hybridizations on glass supports: a novel linker for oligonucleotides synthesized *in situ*," *Nucleic Acids Research* 20:1679–1684 (1992).

Newton, CR, et al., "Analysis of any point mutation in DNA. The amplification refractory mutation refractory mutation system (ARMS)," *Nucl. Acids Res.* 17:2503–2516 (1989).

Velculescu, L., et al., "Serial Analysis of Gene Expression," *Sci.* 270:484–487 (1995).

Vogelstein, B., et al., "Supercoiled loops and eucaryotic DNA replication," *Cell* 22:79–85 (1980).

Nisson, M., et al., "U. Padlock probes reveal single–nucleotide differences, parent of origin and *in situ* distribution of centromeric sequences in human chromosomes 13 and 21," *Nature Genet.* 16:252–255 (1997).

Prakash, G., et al., "Structural effects in the recognition of DNA by circular oligonucleotides," *J. Amer. Chem. Soc.* 114:3523–3527 (1992).

Richards, B., et al., "Conditional mutator phenotypes in hMS2H2–deficient tumor cell lines," *Science* 277:1523–1526 (1997).

Saris, C.J., et al., "Blotting of RNA into RNA exchange paper allowing subsequence characterization by in situ translation in addition to blot hybridization," *Nucleic Acids Res.* 10:4831–4843 (1982).

Schena, M., et al., "Quantitative monitoring of gene expression patterns with a complementary DNA microarray," *Science* 270:467–470 (1995).

Schena, M., et al., "Parallel human genome analysis: Microarray–based expression monitoring of 1000 genes," *Proc. Natl. Acad. Sci. USA* 91:10614–10619 (1994).

Schwarz K., "Improved yields of long PCR products using gene 32 protein," *Nucl. Acids Res.* 18:1079 (1990).

Strauss and Jacobowitz, "Quantitative measure of calretinin and β–actin mRNAIN rat brain micropunches without prior isolation of RNA," *Mol. Brain Res.* 20:229–239 (1993).

Thomas, D.C., et al., "Cascade rolling circle amplification, a homogeneous fluorescence detection system for DNA diagnostics," *Clin Chem* 43:2219 Abs. 38 (1997).

Walker, G.T., et al., "Strand Displacement Amplification an Isothermal, in vitro DNA amplification technique," *Nucleic Acids Research* 20:1691–1696 (1992).

Daubendiek, S.L., et al., "Generation of catalytic RNAs by rolling transcription of synthetic DNA nanocircles," *Nature Biotechnology* 15:273–277 (1997).

Daubendiek, S.L., et al., "Rolling–Circle RNA Synthesis: Circular Oligonucleotides as Efficient Substrates for T7 RNA Polymerase," *J. Am. Chem Soc.* 117:7818–7819 (1995).

Abravaya et al., "Detection of point mutations with a modified ligase chain reaction(Gap–LCR)", *Nucleic Acids Res.*, 23(4):675–682 (1995).

Alves and Carr, "Dot blot detection of point mutations with adjacently hybridising synthetic oligonucleotide probes", *Nucleic Acids Res.*, 16(17):8723 (1988).

Arnold et al., "Assay Formats Involving Acridinium–Ester-Labeled DNA Probes", *Clin. Chem.*, 35(8):1588–1594 (1989).

Barany, "Genetic disease detection and DNA amplification using cloned thermostable ligase", *Proc. Natl. Acad Sci. USA*, 88:189–193 (1991).

Bertina et al., "Mutation in blood coagulation factor V associated with resistance to activated protein C", *Nature*, 369:64–67 (1994).

Birkenmeyer and Mushahwar, "DNA probe amplification methods", *Journal of Virological Methods*, 35:117–126 (1991).

Balanco and Salas, "Characterization and purification of a phage ø29–encoded DNA polymerase required for the initiation of replication", *Proc. Natl. Acad Sci. USA*, 81:5325–5329 (1984).

Blanco et al., "Highly Efficient DNA Synthesis by the Phage ø29 DNA Polymerase", *Journal of Biological Chemistry*, 264(15):8935–8940 (1989).

Blanco et al., "Terminal protein–primed DNA amplification", *Proc. Natl. Acad Sci. USA*, 91:12198–12202 (1994).

Boehmer and Lehman, "Herpes Simplex Virus Type 1 ICP8: Helix–Destabilizing Properties", *Journal of Virology*, 67(2):711–715 (1993).

Broude et al., "Enhanced DNA sequencing by hybridization", *Proc. Natl. Acad Sci. USA*, 91:3072–3076 (1994).

Butler and Chamberlin, "Bacteriophage SP6–specific RNA Polymerase", *Journal of Biological Chemistry*, 257:5772–5778 (1982).

Chatterjee et al., "Cloning and overexpression of the gene encoding bacteriophage T5 DNA polymerase", *Gene*, 97:13–19 (1991).

Davanloo et al., "Cloning and expression of the gene for bacteriophage 7 RNA polymerase", *Proc. Natl. Acad. Sci. USA*, 81:2035–2039 (1984).

Fire and Xu, "Rolling replication of short DNA circles", *Proc. Natl. Acad Sci. USA*, 92: 4641–4645 (1995).

Gasparro et al., "Site–specific targeting of psoralen photoadducts with a triple helix–forming oligonucleotide: characterization of psoralen monoadduct and crosslink formation" *Nucleic Acids Research*, 22(14):2845–2852 (1994).

Gunji et al., "Correlation Between the Serum Level of Hepatitis C Virus RNA and Disease Activities in Acute and Chronic Hepatitis C", *Int. J. Cancer*, 52(5):726–730 (1992).

Guo et al., "Direct fluorescence analysis of genetic polymorphisms by hybridization with oligonucleotide arrays on glass supports", *Nucleic Acids Res.*, 22(24):5456–5465 (1994).

Gupta et al., "Ninth International Conference on AIDS/Fourth STD World Congress", Jun. 6–11, 1993, Berlin, Germany.

Hagiwara et al., "Quantitation of hepatitis C Virus RNA in Serum of Asymptomatic Blood Donors and Patients with Type C Chronic Liver Disease", *Hepatology*, 17(4):545–550 (1993).

Hanvey et al., "Antisense and Antigene Properties of Peptide Nucleic Acids", *Science*, 258:1481–1485 (1992).

Hata et al., "Structure of the Human Ornithine Transcarbamylase Gene", *J. Biochem.*, 103:302–308 (1988).

Hendrickson et al., "High sensitivity multianalyte immunoassay using covalent DNA–labeled antibodies and polymerase chain reaction", *Nucleic Acids Res.*, 23(3):522–529 (1995).

Holloway et al., "An exonuclease–amplification coupled capture technique improves detection of PCR product", *Nucleic Acids Research*, 21:3905–3906 (1993).

Hoy and Schimke, "Bromodeoxyuridine/DNA analysis of replication in CHO cells after exposure to UV light", *Mutation Research*, 290:217–230 (1993).

Hsuih et al., "Quantitative Detection of HCV RNA Using Novel Ligation–Dependnet Polymerase Chain Reaction", *American Association for the Study of Liver Diseases*, (Chicago, IL, Nov. 3–7, 1995) [poster abstract].

Itakura et al., "Synthesis and Use of Synthetic Oligonucleotides", *Annual Review of Biochemistry*, 53:323–356 (1984).

Jacobsen et al., "The N–Terminal Amino–Acid Sequences of DNA Polymerase I from *Escherichia coli* and of the Large and the Small Fragments Obtained by a Limited Proteolysis", *Eur. J. Biochem.*, 45:623–627 (1974).

Jung et al., "Bacteriophage PRDI DNA polymerase: Evolution of DNA polymerases", *Proc. Natl. Acad. Sci. USA*, 84:8287 (1987).

Kaboord and Benkovic, "Accessory proteins function as matchmakers in the assembly of the T4 DNA polymerase holoenzyme", *Current Biology*, 5:149–157 (1995).

Kälin et al., "Evaluation of the ligase chain reaction (LCR) for the detection of point mutations", *Mutation Research*, 283(2):119–123 (1992).

Kellogg et al., "TaqStart Antibody™: "Hot Start" PCR Facilitated by a Neutralizing Monoclonal Antibody Directed Against Taq DNA Polymerase", *Bio Techniques*, 16(6):1134–1137 (1994).

Kerkhof, "A Comparison of Substrates for Qualifying the Signal from a Nonradiolabeled DNA Probe", *Analytical Biochemistry*, 205:359–364 (1992).

Khrapko et al., "Hybridization of DNA with Oligonucleotides Immobilized in Gel: A Convenient Method for Detecting Single Base Substitutions", *Molecular Biology* (Mosk) (USSR) 25:718–730 (1991).

King et al., "Bridging the Gap", *Journal of Biological Chemistry*, 269(18):13061–13064 (1994).

Kong et al., "Characterization of a DNA Polymerase from the Hyperthermophile Archaea *Themococcus literolis*", *Journal of Biological Chemistry*, 268:1965–1975 (1993).

Kunkel et al., "Rapid and Efficient Site–Specific Mutagenesis without Phenotypic Selection", *Methods in Enzymology*, 154:367–382 (1987).

Lamture et al., "Direct detection of nucleic acid hybridization on the surface of a charge coupled device" *Nucleic Acids Research*, 22(11):2121–2125 (1994).

Landegren et al., "A Ligase–Mediated Gene Detection Technique", *Science*, 241:1077–1080 (1988).

Langer et al., "Enzymatic synthesis of biotin–labeled polynucleotides: Novel nucleic acid affinity probes", *Proc. Natl. Acad Sci. USA*, 78(11)6633–6637 (1981).

Lawyer et al., "High–level Expression, Purification, and Enzymatic Characterization of Full–length *Thermus aquaticus* DNA Polymerase and a Truncated Form Deficient in 5' to 3' Exonuclease Activity", *PCR Methods Applications* 2(4):275–287 (1993).

LeFrere et al., "Towards a new predictor of AIDS progression through the quantitation of HIV–1 DNA copies by PCR in HIV–infected individuals", *British Journal of Haematology*, 82(2):467–471 (1992).

Lesnick and Freier, "Relative Thermodynamic Stability of DNA, RNA, and DNA:RNA Hybrid Duplexes: Relationship with Base Composition and Structure", *Biochemistry* 34:10807–10815 (1995).

Lu et al., "High Concentration of Peripheral Blood Mononuclear Cells Harboring Infectious Virus Correlates with Rapid Progression of Human Immunodeficiency Virus Type 1–Related Diseases", *JID*, 168(5):1165–8116 (1993).

Marshall et al., "Detection of HCV RNA by the Asymmetric Gap Ligase Chain Reaction", *PCR Methods and Applications*, 4:80–84 (1994).

Masumoto et al., Primary structure of bacteriophage M2 DNA polymerase: conserved segments within protein–priming DNA polymerases and DNA polymerase 1 of *Escherichia coli*, *Gene* 84(2):247–255 (1989).

Melton et al., "Efficient *in vitro* synthesis of biologically active RNA and RNA hybridization probes from plasmids containing a bacteriophage SP6 promoter", *Nucleric Acids Research*, 12(18): 7035–7056 (1984).

Narang et al., "Chemical Synthesis of Deoxyoligonucleotides by the Modified Triester Method", *Methods Enzymology*, 65:610–620 (1980).

Nielsen et al., "Peptide nucleic acids (PNAs): Potential anti–sense and anti–gene agents", *Anti–Cancer Drug Design*, 8:53–63 (1993).

Nielsen et al., "Peptide Nucleic Acid (PNA). A DNA Mimic with a Peptide Backbone", *Bioconjugate Chemistry*, 5:3–7 (1994).

Nikiforov et al., "The Use of Phosphorothioate Primers and Exonuclease Hydrolysis for the Preparation of Single-stranded PCR Products and their Detection by Solid-phase Hybridization", *PCR Methods and Applications*, 3:285–291 (1994).

Nikiforov et al., "Genetic Bit Analysis: a solid phase method for typing single nucleotide polymorphisms", *Nucleic Acids Research* 22(20):4167–4175 (1994).

Nilsson et al., "Padlock Probes: Circularizing Oligonucleotides for Localized DNA Detection", *Science*, 265:2085–2088 (1994).

Ørum et al., "Single base pair mutation analysis by PNA directed PCR clamping", *Nucleic Acids Research*, 21(23):5332–5336 (1993).

Panasnko et al., A Simple, Three–Step Procedure for the Large Scale Purification of DNA Ligase from a Hybrid λ Lysogen Construction *in Vitro, Journal Biological Chemistry*, 253:4590–4592 (1978).

Pease et al., "Light-generated oligonucleotide arrays for rapid DNA sequence analysis", *Proc. Natl. Acad. Sci. USA* 91(11):5022–5026 (1994).

Piatak et al., "High Levels of HIV-1 in Plasma During All Stages of Infection Determined by Competitive PCR", *Science*, 259(5102): 1749–1754 (1993).

Pokrovskaya and Gurevich, "In Vitro Transcription: Preparative RNA Yields in Analytical Scale Reactions", *Analytical Biochemistry*, 220:420–423 (1994).

Ried et al., "Simultaneous visualization of seven different DNA probes by *in situ* hybridization using combinatorial fluorescence and digital imaging microscopy", *Proc. Natl. Acad. Sci. USA* 89(4): 1388–1392 (1982).

Rigler and Romano, "Differences in the Mechanism of Stimulation of T7 DNA Polymerase by Two Binding Modes of *Escherichia coli* Single-stranded DNA-binding Protein", *Journal of Biological Chemistry*, 270(15):8910–8919 (1995).

Rychlik et al., "Optimization of the annealing temperature for DNA amplification *in vitro*", *Nucleic Acids Research*, 18(21):6409–6412 (1990).

Rys and Persing, "Preventing False Positives: Quantitative Evaluation of Three Protocols for Inactivation of Polymerase Chain Reaction Amplification Products", *Journal of Clinical Microbiology*, 31(9):2356–2360 (1993).

Saksela et al., "Human Immunodeficiency virus type 1 mRNA expression in peripheral blood cells predicts disease progression independently of the numbers of $CD4^+$ lymphocytes", *Proc. Natl. Acad. Sci. USA*, 91(3):1104–1108 (1994).

Sambrook et al., "Molecular Cloning: A Laboratory Manual, Second Edition" (*Cold Spring Harbor Laboratory Press*, Cold Spring Harbor, N.Y., 1989 (Chapters 5, 6)).

Schenborn and Meirendorf, "A novel transcription property of SP6 and 17 RNA polymerases: dependence on template structure", *Nucleic Acids Research*, 13(17):6223–6236 (1985).

Siegel et al., "A Novel DNA Helicase from Calf Thymus", *Journal of Biological Chemistry* 267(19):13629–13635 (1992).

Skaliter and Lehman, "Rolling circle DNA replication *in vitro* by a complex of herpes simplex virus type 1–encoded enzymes", *Proc. Natl. Acad. Sci. USA*, 91(22):10665–10669 (1994).

Speicher et al., "Karyotyping human chromosomes by combinatorial multi–fluor FISH", *Nature Genetics* 12(4):368–375 (1996).

Stimpson et al., "Real-time detection of DNA hybridization and melting on oligonucleotide arrays by using optical wave guides", *Proc. Natl. Acad. Sci. USA* 92(14):6379–6383 (1995).

Studier et al., "Use of T7 RNA Polymerase to Direct Expression of Cloned Genes", *Methods in Enzymology*, 185:60–89 (1990).

Syvänen et al., "Fast Qualification of nucleic acid hybrids by affinity-based hybrid collection", *Nucleic Acids Research*, 14(12):5037–5049 (1986).

Thorbjarnardottir et al., "Sequence of the DNA ligase-encoding gene from *Thermus scotoductus* and conserved motifs in DNA ligases", *Gene* 151(1&2):177–180 (1995).

Tsurumi et al., "Functional Interaction between EpsteinBarr Virus DNA Polymerase Catalytic Subunit and Its Accessory Subunit In Vitro", *Journal of Virology*, 67(12):7648–7653 (1993).

Walter and Strunk, "Strand displacement amplification as an *in vitro* model for rolling–circle replication: Deletion formation and evolution during serial transfer", *Proc. Natl. Acad Sci. USA*, 91:7937–7941 (1994).

Wansink et al., "Fluorescent Labeling of Nascent RNA Polymerase II in Domains Scattered Throughout the Nucleus", 122(2):283–293 (1993).

Wiedmann et al., "Ligase Chain Reaction (LCR)—Overview and Applications", *PCR Methods and Applications* (Cold Spring Harbor Laboratory Press, Cold Spring Harbor Laboratory, NY, 1994) pp. S51–S64.

Winn–Deen et al., "Non-radioactive detection of Mycobacterium tuberculosis LCR products in a microtitre plate format", *Molecular and Cellular Probes*, (England) 7(3):179–186 (1993).

Young and Anderson, "Quanitiative analysis of solution hybridisation", *Nucleic Acid Hybridisation: A Practical Approach* (IRL Press, 1985) pp. 47–71.

Yu et al., "Cyanine dye dUTP analogs for enzymatic labeling of DNA probes", *Nucleic Acids Research*, 22(15):3226–3232 (1994).

Zhu and Ito, "Purification and characterization of PRD1 DNA polymerase", *Biochimica Biophysica Acta* 1219(2):267–276 (1994).

Zijderveld and van der Vliet, "Helix–Destabilizing Properties of the Adenovirus DNA–Binding Protein", *Journal of Virology* 68(2):1158–1164 (1994).

Johnstone and Thorpe, *Immunochemistry In Practice* (Blackwell Scientific Publications, Oxford, England, 1987) pp. 209–216 and 241–242.

Landegren, "Molecular mechanics of nucleic acid sequence amplification," *Trends Genetics*, 9:199–202 (1993).

McGraw et al., "Sequence–dependent oligonucleotide–target duplex stabilities: rules from empirical studies with a set of twenty–mers" *Biotechniques* 8:674–678 (1990).

Burgess and Jacutin,"A new photolabile protecting group for nucleotides"*Am. Chem Soc.* Abstracts vol. 221, abstract 281 (1996).

Ernst et al., "Cyanine dye labeling reagents for sulfhydryl groups" *Cytometry* 10:3–10 (1989).

Kaplan et al., "Rapid photolytic release of adenosine 5'–triphosphate from a protected analogue: utilization by the Na:K pump of human red blood cell ghosts" *Biochem.* 17:1929–1935 (1978).

McCray et al., "A new approach to time–resolved studies of ATP–requiring biological systems: Laser flash photolysis of caged ATP" *Proc. Natl. Acad. Sci. USA* 77:7237–7241 (1980).

Metzker et al., "Termination of DNA synthesis by novel 3'–modified–deoxyribonucleoside 5'–triphosphates" *Nucleic Acids Research* 22:4259–4267 (1994).

Mujumdar et al., "Cyanine dye labeling reagents containing isothiocyanate groups" *Cytometry* 10:11–19 (1989).

Pillai et al., "Photoremovable protecting groups in organic synthesis" *Synthesis* 1–26 (1980).

Schena et al., "Quantitative Monitoring of Gene Expression Patterns with a Complementary DNA Microarray" *Science* 270:467–470 (1995).

Tabor and Richardson, "Selective oxidation of the exonuclease domain of bacteriophage T7 DNA polymerase" *J. Biol. Chem.* 262:15330–15333 (1987).

Tabor and Richardson, "Selective inactivation of the exonuclease activity of bacteriophage T7 DNA polymerase by in vitro mutagenesis" *J. Biol. Chem.* 264:6447–6458 (1989).

Tyagi and Kramer, "Molecular beacons: probes that fluoresce upon hybridization" *Nature Biotechnology* 14:303–308 (1996).

Waggoner A., "Covalent labeling of proteins and nucleic acids with fluorophores" *Meth. Enzymology* 246:362–373 (1995).

Zehavi et al., "Light sensitive glycosides. I. 6–Nitoveratryl β–D–Glucopyranoside and 2–Nitrobenzyl β–D–Glucopyranoside" *Organic Chem.* 37:2281–2288 (1972).

* cited by examiner

ROLLING CIRCLE AMPLIFICATION

ADDRESS PROBE HYBRIDIZING TO TS-DNA PORTION
BRIDGING GAP OLIGONUCLEOTIDE AND TARGET PROBE ENDS

```
                  5'-CCTT-    -3'              GAP
                                               OLIGONUCLEOTIDE

5'-TTTTTTTTTTTTTTGTATT CCTT GCCTG  -3'         ADDRESS
                                               PROBE
```

HYBRIDIZATION OF TS-DNA AND ADDRESS PROBE

```
3'-ACAGACGACGGGAGACATAA GGAA CGGACAGGTCCCTAGACGAG  -5'
                       ||||  |||| |||| |||         TS-DNA
                   GTATT CCTT GCCTG   -3'   ADDRESS PROBE
                       /
5'-TTTTTTTTTTTTTT
```

LM-RCA FOLLOWED BY TRANSCRIPTION
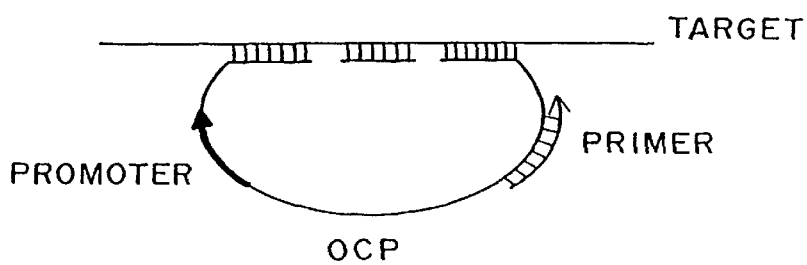
FIG. 8
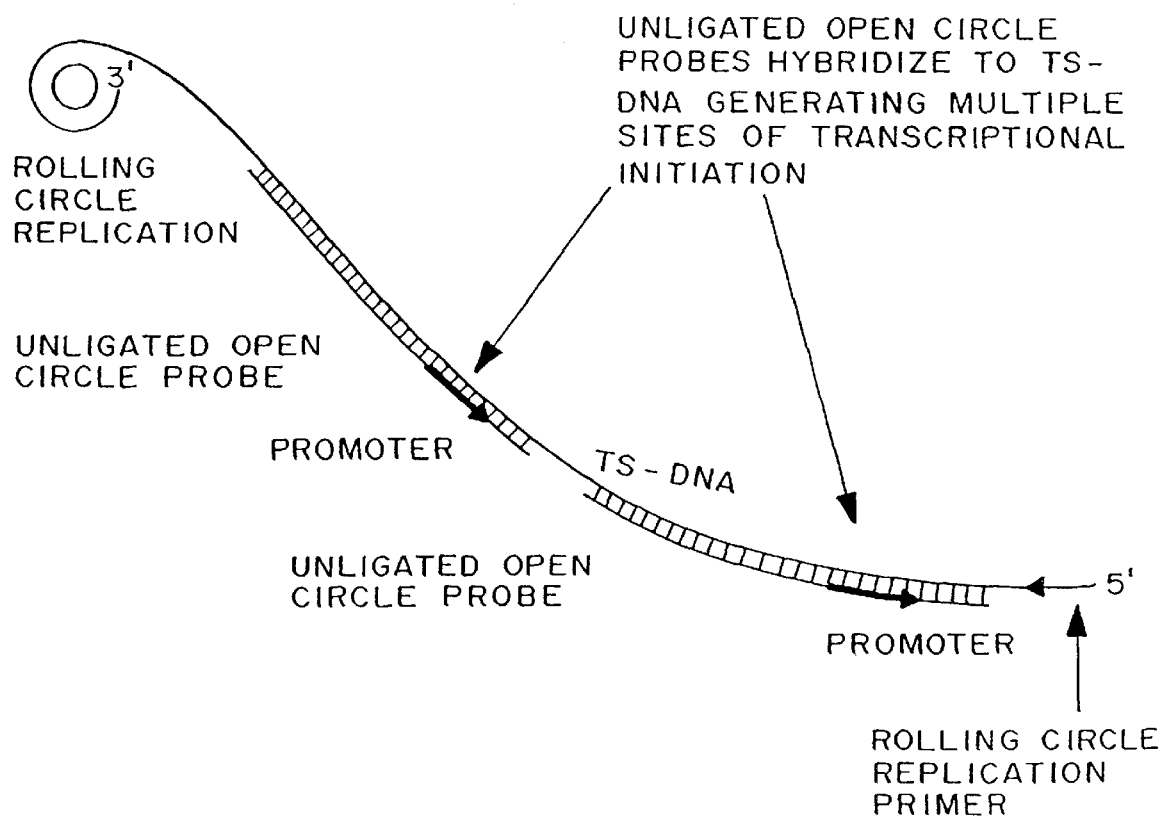

REPORTER ANTIBODIES
IgG1 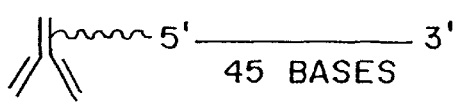 DNA 1
IgG 2 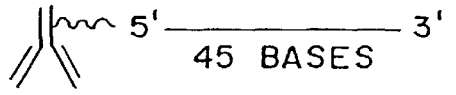 DNA 2
IgG 3 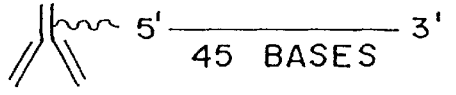 DNA 3
3 DIFFERENT DNA TAGS
ASSAY
ANALYTE → 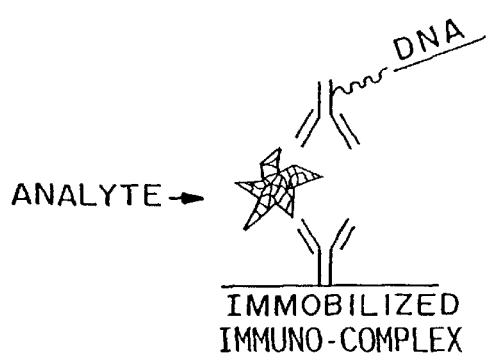
IMMOBILIZED IMMUNO-COMPLEX
LM-RCA OR
——————→
LM-RCT USING 3 SETS OF PROBES
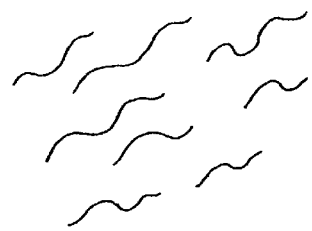
AMPLIFIED DNA OR RNA CORRESPONDING TO DNA TAG SEQUENCE THAT WAS BOUND
FIG. 9

FIG. 10
DETECTION EXAMPLE
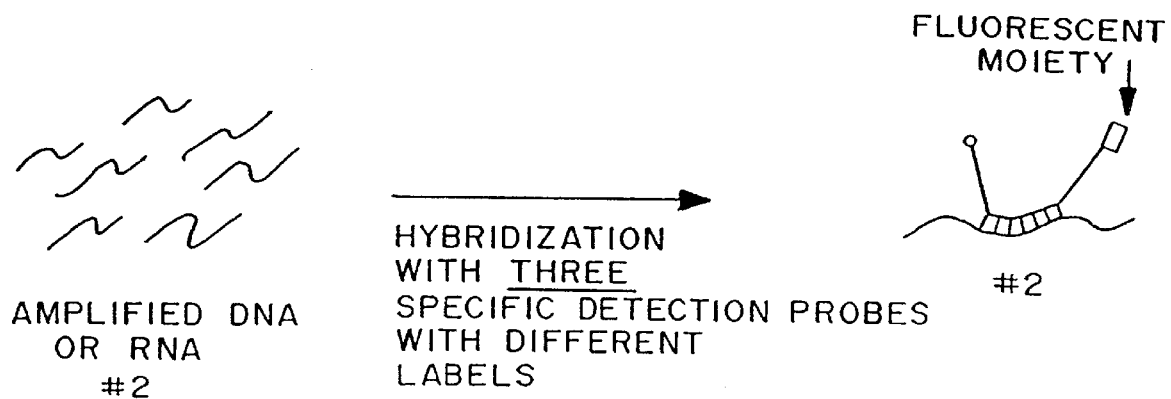
DETECTION EXAMPLE
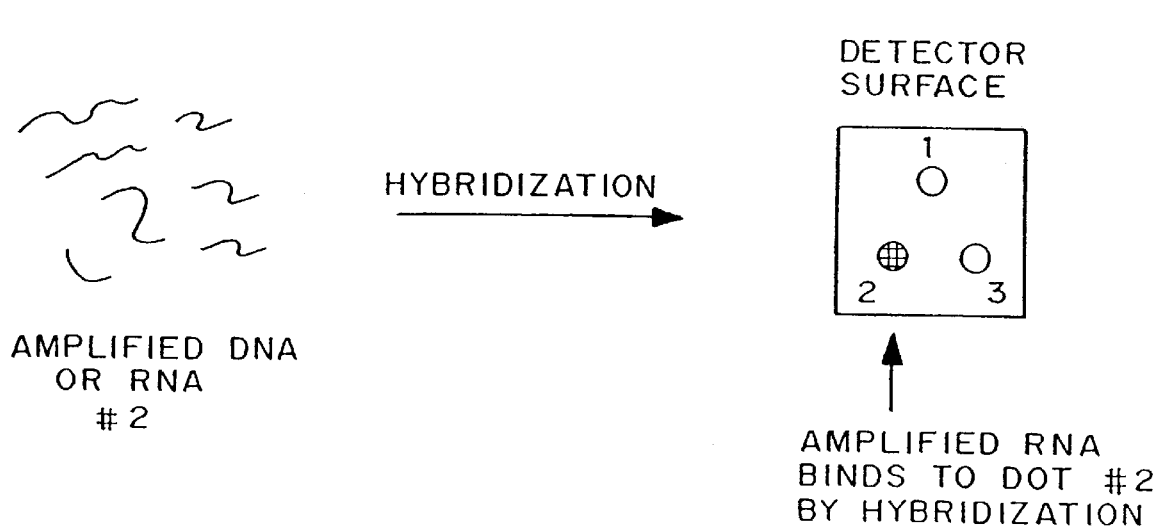

FIG. 12
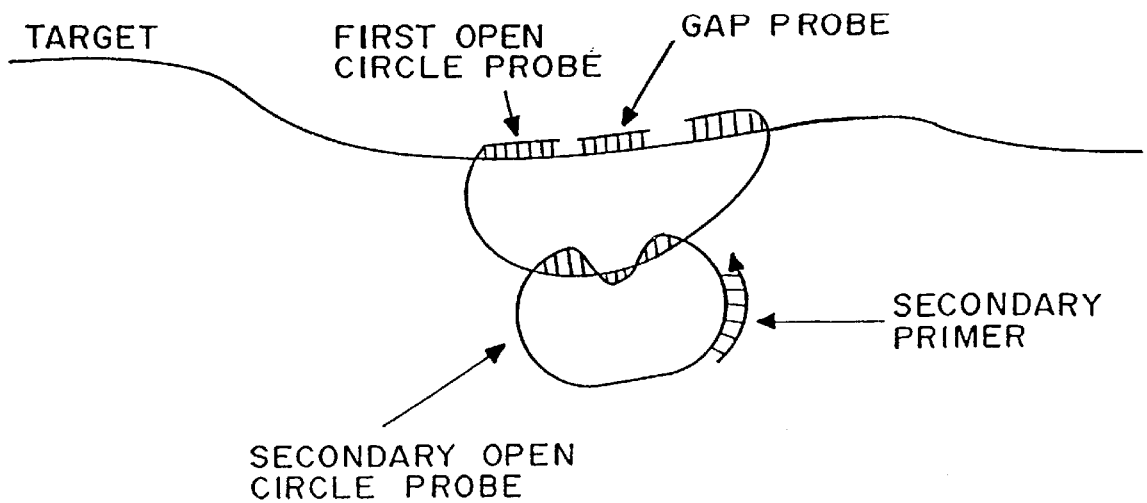
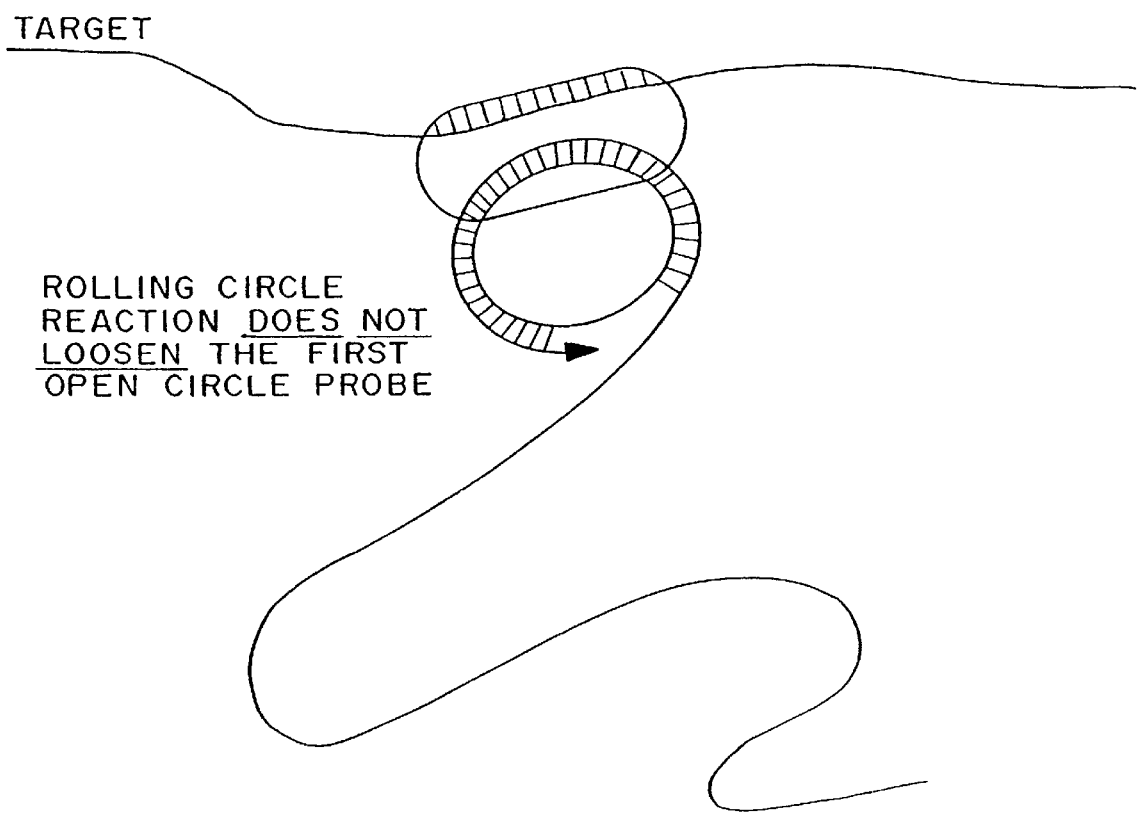

OPPOSITE STRAND AMPLIFICATION

*FIG. 15*
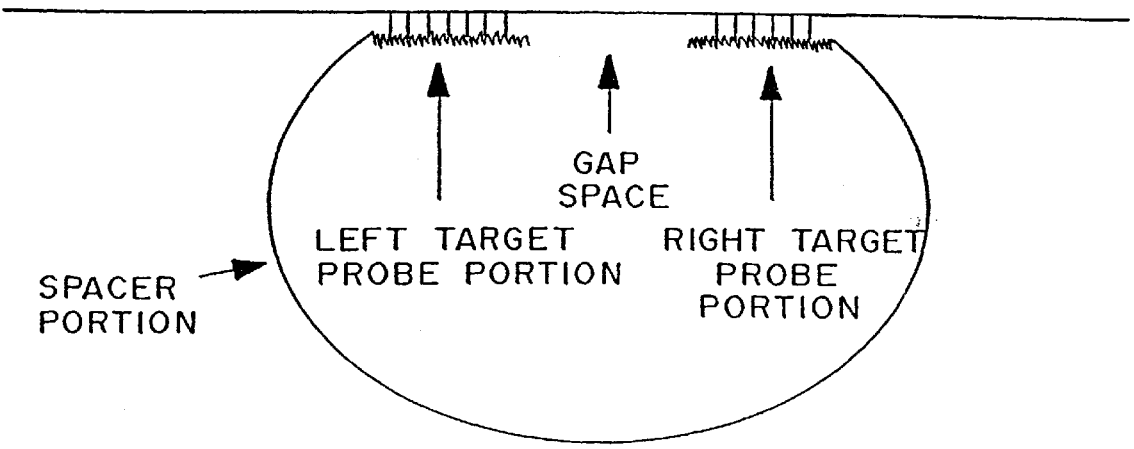
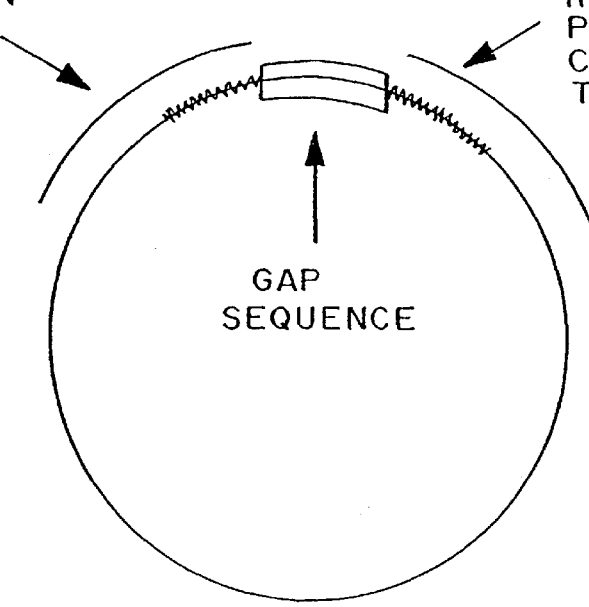

Somatic mutation

Homozygous

Heterozygous

Figure 17A

Target sequence (3' to 5')
...CCGAGCTGTGTAGATTGCTAGCTAGGATCACACACACACACAGTTAGACATAGATCGATACATGCATGCACTTGAA...
   ||||||||||||||||||                                        ||||||||||||||||||
   ...CTCGACATCTAACGATCGAT                                   ATCTAGCTATGTACGTGAAC...
   Left target probe                                         Right target probe CCTAGTGTGTGTGTGTGTGTGTGTCAATCTGT
                    Fill sequence (32 nucleotides)

Figure 17B

Target sequence (3' to 5')
...CCGAGCTGTGTAGATTGCTAGCTAGGATCACACACACACACAGTTAGACATAGATCGATACATGCATGCACTTGAA...
   ||||||||||||||||||                                        ||||||||||||||||||
   ...CTCGACATCTAACGATCGAT                                   ATCTAGCTATGTACGTGAAC...
   Left target probe                                         Right target probe CCTAGTGTGTGTGTGTGTGTGTCAATCTGT
                    Fill sequence (30 nucleotides)

Figure 21A

Normal Sequence – After degenerate probe ligation

Slide 1

Row 1  TCTCGACATCTAACGATCGATCCTA
       TAGAGCTGTAGATTGCTAGCTAGGATCACACACACACACACACACAGTTAGACATAGATC

Row 2  TCTCGACATCTAACGATCGATCCTAGTGTG
       TAGAGCTGTAGATTGCTAGCTAGGATCACACACACACACACACACAGTTAGACATAGATC

Row 3  TCTCGACATCTAACGATCGATCCTAGTGTGTGT
       TAGAGCTGTAGATTGCTAGCTAGGATCACACACACACACACACACAGTTAGACATAGATC

Row 4  TCTCGACATCTAACGATCGATCCTAGTGTGTGTGTGTG
       TAGAGCTGTAGATTGCTAGCTAGGATCACACACACACACACACACAGTTAGACATAGATC

Row 5  TCTCGACATCTAACGATCGATCCTAGTGTGTGTGTGTGTGT
       TAGAGCTGTAGATTGCTAGCTAGGATCACACACACACACACACACAGTTAGACATAGATC

Figure 21B

Normal Sequence - After degenerate probe ligation

Slide 2

Row 1   CTCGACATCTAACGATCGATCCTAG
        TAGAGCTGTAGATTGCTAGCTAGGATCACACACACACACACACAGTTAGACATAGATC

Row 2   CTCGACATCTAACGATCGATCCTAGTGTGT
        TAGAGCTGTAGATTGCTAGCTAGGATCACACACACACACACACAGTTAGACATAGATC

Row 3   CTCGACATCTAACGATCGATCCTAGTGTGTGTG
        TAGAGCTGTAGATTGCTAGCTAGGATCACACACACACACACACAGTTAGACATAGATC

Row 4   CTCGACATCTAACGATCGATCCTAGTGTGTGTGTGTGT
        TAGAGCTGTAGATTGCTAGCTAGGATCACACACACACACACACAGTTAGACATAGATC

Row 5   CTCGACATCTAACGATCGATCCTAGTGTGTGTGTGTGTGTGTC
        TAGAGCTGTAGATTGCTAGCTAGGATCACACACACACACACACAGTTAGACATAGATC

Figure 21C

Normal Sequence - After degenerate probe ligation

Slide 3

Row 1  TCGACATCTAACGATCGATCCTAGT
       TAGAGCTGTAGATTGCTAGGATCACACACACACACAGTTAGACATAGATC

Row 2  TCGACATCTAACGATCGATCCTAGTGTGTG
       TAGAGCTGTAGATTGCTAGGATCACACACACACACAGTTAGACATAGATC

Row 3  TCGACATCTAACGATCGATCCTAGTGTGTGT
       TAGAGCTGTAGATTGCTAGGATCACACACACACACAGTTAGACATAGATC

Row 4  TCGACATCTAACGATCGATCCTAGTGTGTGTGTGTG
       TAGAGCTGTAGATTGCTAGGATCACACACACACACAGTTAGACATAGATC

Row 5  TCGACATCTAACGATCGATCCTAGTGTGTGTGTGTGTCA
       TAGAGCTGTAGATTGCTAGGATCACACACACACACAGTTAGACATAGATC

Figure 21D

Normal Sequence - After degenerate probe ligation

Slide 4

Row 1  CGACATCTAACGATCGATCCTAGTG
       TAGAGCTGTAGATTGCTAGGATCACACACACACACAGTTAGACATAGATC

Row 2  CGACATCTAACGATCGATCCTAGTGTGT
       TAGAGCTGTAGATTGCTAGGATCACACACACACACAGTTAGACATAGATC

Row 3  CGACATCTAACGATCGATCCTAGTGTGTGTGTG
       TAGAGCTGTAGATTGCTAGGATCACACACACACACAGTTAGACATAGATC

Row 4  CGACATCTAACGATCGATCCTAGTGTGTGTGTGTGT
       TAGAGCTGTAGATTGCTAGGATCACACACACACACAGTTAGACATAGATC

Row 5  CGACATCTAACGATCGATCCTAGTGTGTGTGTGTGTGTCAA
       TAGAGCTGTAGATTGCTAGGATCACACACACACACAGTTAGACATAGATC

Figure 21E

Normal Sequence - After degenerate probe ligation

Slide 5

Row 1   GACATCTAACGATCGATCCTAGTGT
        TAGAGCTGTGTAGATTGCTAGCTAGGATCACACACACACACAGTTAGACATAGATC

Row 2   GACATCTAACGATCGATCCTAGTGTGTG
        TAGAGCTGTGTAGATTGCTAGCTAGGATCACACACACACACAGTTAGACATAGATC

Row 3   GACATCTAACGATCGATCCTAGTGTGTGTGT
        TAGAGCTGTGTAGATTGCTAGCTAGGATCACACACACACACAGTTAGACATAGATC

Row 4   GACATCTAACGATCGATCCTAGTGTGTGTGTGTG
        TAGAGCTGTGTAGATTGCTAGCTAGGATCACACACACACACAGTTAGACATAGATC

Row 5   GACATCTAACGATCGATCCTAGTGTGTGTGTGTGTCAAT
        TAGAGCTGTGTAGATTGCTAGCTAGGATCACACACACACACAGTTAGACATAGATC

Figure 22A

Normal Sequence - After primer extension

Slide 1

Row 1 TCTCGACATCTAACGATCGATCCTAG
TAGAGCTGTAGATTGCTAGCTAGGATCACACACACACACACACAGTTAGACATAGATC

Row 2 TCTCGACATCTAACGATCGATCCTAGTGTGT
TAGAGCTGTAGATTGCTAGCTAGGATCACACACACACACACACAGTTAGACATAGATC

Row 3 TCTCGACATCTAACGATCGATCCTAGTGTGTGTG
TAGAGCTGTAGATTGCTAGCTAGGATCACACACACACACACACAGTTAGACATAGATC

Row 4 TCTCGACATCTAACGATCGATCCTAGTGTGTGTGTGT
TAGAGCTGTAGATTGCTAGCTAGGATCACACACACACACACACAGTTAGACATAGATC

Row 5 TCTCGACATCTAACGATCGATCCTAGTGTGTGTGTGTGTGTC
TAGAGCTGTAGATTGCTAGCTAGGATCACACACACACACACACAGTTAGACATAGATC

Figure 22B

Normal Sequence - After primer extension

Slide 2

Row 1  CTCGACATCTAACGATCGATCCTAGT
       TAGAGCTGTAGATTGCTAGCTAGGATCACACACACACACACACAGTTAGACATAGATC

Row 2  CTCGACATCTAACGATCGATCCTAGTGTGTG
       TAGAGCTGTAGATTGCTAGCTAGGATCACACACACACACACACAGTTAGACATAGATC

Row 3  CTCGACATCTAACGATCGATCCTAGTGTGTGTGTGT
       TAGAGCTGTAGATTGCTAGCTAGGATCACACACACACACACACAGTTAGACATAGATC

Row 4  CTCGACATCTAACGATCGATCCTAGTGTGTGTGTGTGTGTG
       TAGAGCTGTAGATTGCTAGCTAGGATCACACACACACACACACAGTTAGACATAGATC

Row 5  CTCGACATCTAACGATCGATCCTAGTGTGTGTGTGTGTGTGTGTCA
       TAGAGCTGTAGATTGCTAGCTAGGATCACACACACACACACACAGTTAGACATAGATC

Figure 22C

Normal Sequence - After primer extension

Slide 3

Row 1  TCGACATCTAACGATCGATCCTAGTG
       TAGAGCTGTAGATTGCTAGCTAGGATCACACACACACACACACAGTTAGACATAGATC

Row 2  TCGACATCTAACGATCGATCCTAGTGTGT
       TAGAGCTGTAGATTGCTAGCTAGGATCACACACACACACACACAGTTAGACATAGATC

Row 3  TCGACATCTAACGATCGATCCTAGTGTGTGTG
       TAGAGCTGTAGATTGCTAGCTAGGATCACACACACACACACACAGTTAGACATAGATC

Row 4  TCGACATCTAACGATCGATCCTAGTGTGTGTGTGTGT
       TAGAGCTGTAGATTGCTAGCTAGGATCACACACACACACACACAGTTAGACATAGATC

Row 5  TCGACATCTAACGATCGATCCTAGTGTGTGTGTGTGTGTCAA
       TAGAGCTGTAGATTGCTAGCTAGGATCACACACACACACACACAGTTAGACATAGATC

Figure 22D

Normal Sequence - After primer extension

Slide 4

Row 1  CGACATCTAACGATCGATCCTAGTGT
       TAGAGCTGTAGATTGCTAGGATCACACACACACACACACAGTTAGACATAGATC

Row 2  CGACATCTAACGATCGATCCTAGTGTGTG
       TAGAGCTGTAGATTGCTAGGATCACACACACACACACACAGTTAGACATAGATC

Row 3  CGACATCTAACGATCGATCCTAGTGTGTGTGT
       TAGAGCTGTAGATTGCTAGGATCACACACACACACACACAGTTAGACATAGATC

Row 4  CGACATCTAACGATCGATCCTAGTGTGTGTGTGTGTG
       TAGAGCTGTAGATTGCTAGGATCACACACACACACACACAGTTAGACATAGATC

Row 5  CGACATCTAACGATCGATCCTAGTGTGTGTGTGTGTGTGTCAAT
       TAGAGCTGTAGATTGCTAGGATCACACACACACACACACAGTTAGACATAGATC

Figure 22E

Normal Sequence - After primer extension

Slide 5

Row 1  GACATCTAACGATCGATCCTAGTGTG
       TAGAGCTGTAGATTGCTAGGATCACACACACACACACAGTTAGACATAGATC

Row 2  GACATCTAACGATCGATCCTAGTGTGTGT
       TAGAGCTGTAGATTGCTAGGATCACACACACACACACAGTTAGACATAGATC

Row 3  GACATCTAACGATCGATCCTAGTGTGTGTGTG
       TAGAGCTGTAGATTGCTAGGATCACACACACACACACAGTTAGACATAGATC

Row 4  GACATCTAACGATCGATCCTAGTGTGTGTGTGTGT
       TAGAGCTGTAGATTGCTAGGATCACACACACACACACAGTTAGACATAGATC

Row 5  GACATCTAACGATCGATCCTAGTGTGTGTGTGTGTGTCAATC
       TAGAGCTGTAGATTGCTAGGATCACACACACACACACAGTTAGACATAGATC

Figure 23A

Deleted Sequence - After degenerate probe ligation

Slide 1

Row 1  TCTCGACATCTAACGATCGATCCTA
       TAGAGCTGTAGATTGCTAGGATCACACACACACACACAGTTAGACATAGATC

Row 2  TCTCGACATCTAACGATCGATCCTAGTGTG
       TAGAGCTGTAGATTGCTAGGATCACACACACACACACAGTTAGACATAGATC

Row 3  TCTCGACATCTAACGATCGATCCTAGTGTGTGT
       TAGAGCTGTAGATTGCTAGGATCACACACACACACAGTTAGACATAGATC

Row 4  TCTCGACATCTAACGATCGATCCTAGTGTGTGTGTG
       TAGAGCTGTAGATTGCTAGGATCACACACACACACAGTTAGACATAGATC

Row 5  TCTCGACATCTAACGATCGATCCTAGTGTGTGTGTGTGTGT
       TAGAGCTGTAGATTGCTAGGATCACACACACACACAGTTAGACATAGATC

Figure 23B

Deleted Sequence - After degenerate probe ligation

Slide 2

Row 1  CTCGACATCTAACGATCGATCCTAG
       TAGAGCTGTAGATTGCTAGGATCACACACACACACAGTTAGACATAGATC

Row 2  CTCGACATCTAACGATCGATCCTAGTGTGT
       TAGAGCTGTAGATTGCTAGGATCACACACACACACAGTTAGACATAGATC

Row 3  CTCGACATCTAACGATCGATCCTAGTGTGTGTG
       TAGAGCTGTAGATTGCTAGGATCACACACACACACAGTTAGACATAGATC

Row 4  CTCGACATCTAACGATCGATCCTAGTGTGTGTGTGTGT
       TAGAGCTGTAGATTGCTAGGATCACACACACACACAGTTAGACATAGATC

Row 5  CTCGACATCTAACGATCGATCCTAGTGTGTGTGTGTGTGTGTC
       TAGAGCTGTAGATTGCTAGGATCACACACACACACAGTTAGACATAGATC

Figure 23C

Deleted Sequence - After degenerate probe ligation

Slide 3

Row 1  TCGACATCTAACGATCGATCCTAGT
       TAGAGCTGTAGATTGCTAGGATCACACACACACACAGTTAGACATAGATC

Row 2  TCGACATCTAACGATCGATCCTAGTGTGTG
       TAGAGCTGTAGATTGCTAGGATCACACACACACACAGTTAGACATAGATC

Row 3  TCGACATCTAACGATCGATCCTAGTGTGTGTGT
       TAGAGCTGTAGATTGCTAGGATCACACACACACACAGTTAGACATAGATC

Row 4  TCGACATCTAACGATCGATCCTAGTGTGTGTGTGTG
       TAGAGCTGTAGATTGCTAGGATCACACACACACACAGTTAGACATAGATC

Row 5  TCGACATCTAACGATCGATCCTAGTGTGTGTGTGTGTCA
       TAGAGCTGTAGATTGCTAGGATCACACACACACACAGTTAGACATAGATC

Figure 23D

Deleted Sequence - After degenerate probe ligation

Slide 4

Row 1   CGACATCTAACGATCGATCCTAGTG
        TAGAGCTGTAGATTGCTAGGATCACACACACACAGTTAGACATAGATC

Row 2   CGACATCTAACGATCGATCCTAGTGTGT
        TAGAGCTGTAGATTGCTAGGATCACACACACACAGTTAGACATAGATC

Row 3   CGACATCTAACGATCGATCCTAGTGTGTGTG
        TAGAGCTGTAGATTGCTAGGATCACACACACACAGTTAGACATAGATC

Row 4   CGACATCTAACGATCGATCCTAGTGTGTGTGTGT
        TAGAGCTGTAGATTGCTAGGATCACACACACACAGTTAGACATAGATC

Row 5   CGACATCTAACGATCGATCCTAGTGTGTGTGTGTCAA
        TAGAGCTGTAGATTGCTAGGATCACACACACACAGTTAGACATAGATC

Figure 23E

Deleted Sequence - After degenerate probe ligation

Slide 5

Row 1   GACATCTAACGATCGATCCCTAGTGT
        TAGAGCTGTAGATTGCTAGGATCACACACACACAGTTAGACATAGATC

Row 2   GACATCTAACGATCGATCCCTAGTGTGTG
        TAGAGCTGTAGATTGCTAGGATCACACACACACAGTTAGACATAGATC

Row 3   GACATCTAACGATCGATCCCTAGTGTGTGTGT
        TAGAGCTGTAGATTGCTAGGATCACACACACACAGTTAGACATAGATC

Row 4   GACATCTAACGATCGATCCCTAGTGTGTGTGTGTG
        TAGAGCTGTAGATTGCTAGGATCACACACACACAGTTAGACATAGATC

Row 5   GACATCTAACGATCGATCCCTAGTGTGTGTGTGTGTGTCAAT
        TAGAGCTGTAGATTGCTAGGATCACACACACACAGTTAGACATAGATC

Figure 24A

Deleted Sequence - After primer extension

Slide 1

Row 1  TCTCGACATCTAACGATCGATCCTAG
       TAGAGCTGTAGATTGCTAGGATCACACACACACACAGTTAGACATAGATC

Row 2  TCTCGACATCTAACGATCGATCCTAGTGT
       TAGAGCTGTAGATTGCTAGGATCACACACACACACAGTTAGACATAGATC

Row 3  TCTCGACATCTAACGATCGATCCTAGTGTGTG
       TAGAGCTGTAGATTGCTAGGATCACACACACACACAGTTAGACATAGATC

Row 4  TCTCGACATCTAACGATCGATCCTAGTGTGTGTGTGT
       TAGAGCTGTAGATTGCTAGGATCACACACACACACAGTTAGACATAGATC

Row 5  TCTCGACATCTAACGATCGATCCTAGTGTGTGTGTGTGTCAA
       TAGAGCTGTAGATTGCTAGGATCACACACACACACAGTTAGACATAGATC

Figure 24B

Deleted Sequence - After primer extension

Slide 2

Row 1    CTCGACATCTAACGATCGATCCTAGT
         TAGAGCTGTAGATTGCTAGGATCACACACACACACAGTTAGACATAGATC

Row 2    CTCGACATCTAACGATCGATCCTAGTGTGTG
         TAGAGCTGTAGATTGCTAGGATCACACACACACACAGTTAGACATAGATC

Row 3    CTCGACATCTAACGATCGATCCTAGTGTGTGTGT
         TAGAGCTGTAGATTGCTAGGATCACACACACACACAGTTAGACATAGATC

Row 4    CTCGACATCTAACGATCGATCCTAGTGTGTGTGTGTGTG
         TAGAGCTGTAGATTGCTAGGATCACACACACACACAGTTAGACATAGATC

Row 5    CTCGACATCTAACGATCGATCCTAGTGTGTGTGTGTGTGTCAAT
         TAGAGCTGTAGATTGCTAGGATCACACACACACACAGTTAGACATAGATC

Figure 24C

Deleted Sequence - After primer extension

Slide 3

Row 1  TCGACATCTAACGATCGATCCTAGTG
       TAGCTGTAGATTGCTAGGATCACACACACACACAGTTAGACATAGATC

Row 2  TCGACATCTAACGATCGATCCTAGTGTGT
       TAGAGCTGTAGATTGCTAGGATCACACACACACACAGTTAGACATAGATC

Row 3  TCGACATCTAACGATCGATCCTAGTGTGTGTG
       TAGAGCTGTAGATTGCTAGGATCACACACACACACAGTTAGACATAGATC

Row 4  TCGACATCTAACGATCGATCCTAGTGTGTGTGTGTGT
       TAGAGCTGTAGATTGCTAGGATCACACACACACACAGTTAGACATAGATC

Row 5  TCGACATCTAACGATCGATCCTAGTGTGTGTGTGTGTGTCAATC
       TAGAGCTGTAGATTGCTAGGATCACACACACACACAGTTAGACATAGATC

Figure 24D

Deleted Sequence - After primer extension

Slide 4

Row 1  CGACATCTAACGATCGATCCTAGTGT
TAGAGCTGTAGATTGCTAGCTAGGATCACACACACACAGTTAGACATAGATC

Row 2  CGACATCTAACGATCGATCCTAGTGTGTG
TAGAGCTGTAGATTGCTAGCTAGGATCACACACACACAGTTAGACATAGATC

Row 3  CGACATCTAACGATCGATCCTAGTGTGTGTGT
TAGAGCTGTAGATTGCTAGCTAGGATCACACACACACAGTTAGACATAGATC

Row 4  CGACATCTAACGATCGATCCTAGTGTGTGTGTGTC
TAGAGCTGTAGATTGCTAGCTAGGATCACACACACACAGTTAGACATAGATC

Row 5  CGACATCTAACGATCGATCCTAGTGTGTGTGTGTGTCAATCT
TAGAGCTGTAGATTGCTAGCTAGGATCACACACACACAGTTAGACATAGATC

Figure 24E

Deleted Sequence - After primer extension

Slide 5

Row 1   GACATCTAACGATCGATCCTAGTGTG
        TAGAGCTGTAGATTGCTAGGATCACACACACACAGTTAGACATAGATC

Row 2   GACATCTAACGATCGATCCTAGTGTGTGT
        TAGAGCTGTAGATTGCTAGGATCACACACACACAGTTAGACATAGATC

Row 3   GACATCTAACGATCGATCCTAGTGTGTGTGTG
        TAGAGCTGTAGATTGCTAGGATCACACACACACAGTTAGACATAGATC

Row 4   GACATCTAACGATCGATCCTAGTGTGTGTGTGTGTCA
        TAGAGCTGTAGATTGCTAGGATCACACACACACAGTTAGACATAGATC

Row 5   GACATCTAACGATCGATCCTAGTGTGTGTGTGTGTGTCAATCTG
        TAGAGCTGTAGATTGCTAGGATCACACACACACAGTTAGACATAGATC

SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 1:

GCCTGTCCAG GGATCTGCTC AAGACTCGTC ATGTCTCAGT AGCTTCTAAC GGTCACAAGC        60

TTCTAACGGT CACAAGCTTC TAACGGTCAC ATGTCTGCTG CCCTCTGTAT T               111

(2) INFORMATION FOR SEQ ID NO: 2:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 2

GAGCAGATCC CTGGACAGGC AAGGAATACA GAGGGCAGCA GACA                         44

(2) INFORMATION FOR SEQ ID NO: 3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 3

GTATTCCTTG CCTGGTATTC CTTGCCTG                                           28

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 4

ATCAGTCTAG TCTATNNNNN                                                    20

(2) INFORMATION FOR SEQ ID NO: 5:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 5

GAGGAGAATA AAAGTTTCTC ATAAGACTCG TCATGTCTCA GCAGCTTCTA ACGGTCACTA      60

ATACGACTCA CTATAGGTTC TGCCTCTGGG AACAC                                95

(2) INFORMATION FOR SEQ ID NO: 6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 6

GCTGAGACAT GACGAGTC                                                   18

(2) INFORMATION FOR SEQ ID NO: 7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 7

TTTTTTTTTT TCCAACCTCC ATCACTAGT                                       29

(2) INFORMATION FOR SEQ ID NO: 8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 8

TTTTTTTTTT TCCAACCTCG ATCACTAGT                                       29

(2) INFORMATION FOR SEQ ID NO: 9:

(i) SEQUENCE CHARACTERISTICS:

```
        (A) LENGTH: 29 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 9

TTTTTTTTTT TTTTTTGATC GAGGAGAAT                                         29

(2) INFORMATION FOR SEQ ID NO: 10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 10

NNNNNATAGA CTAGACTGAT NNN                                               23

(2) INFORMATION FOR SEQ ID NO: 11:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 11

TAAAAGACTT CATCATCCAT CTCATAAGAC TCGTCATGTC TCAGCAGCTT CTAACGGTCA       60

CTAATACGAC TCACTATAGG GGAACACTAG TGATGG                                 96

(2) INFORMATION FOR SEQ ID NO: 12:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 12

TAAAAGACTT CATCATCCAT CTCATAAGAC TCGTCATGTC TCAGCAGCTT CTAACGGTCA       60

CTAATACGAC TCACTATAGG GGAACACTAG TGATCG                                 96

(2) INFORMATION FOR SEQ ID NO: 13:
```

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 13

TTTTTTTTTT TCCAAATTCT CCTCCATCA                                        29

(2) INFORMATION FOR SEQ ID NO: 14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 14

TTTTTTTTTT TCCAAATTCT CCTCGATCA                                        29

(2) INFORMATION FOR SEQ ID NO: 15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 15

TGTCCACTTT CTGTTTTCTG CCTC                                             24

(2) INFORMATION FOR SEQ ID NO: 16:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 16

ATCACTAGTG TTCCTTCTCA TAAGACTCGT CATGTCTCAG CAGCTTCTAA CGGTCACTAA       60

TACGACTCAC TATAGGGGAT GATGAAGTCT TTTAT                                 95

(2) INFORMATION FOR SEQ ID NO: 17:

(i) SEQUENCE CHARACTERISTICS:

(A) LENGTH: 29 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 17

TTTTTTTTTT TTTTTTGATG GAGGAGAAT                              29

(2) INFORMATION FOR SEQ ID NO: 18:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 18

TCTCGACATC TAACGATCGA TCCTAGTGTG TGTGTGTGTG TGTCAATCTG T     51

(2) INFORMATION FOR SEQ ID NO: 19:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 19

CTAGATACAG ATTGACACAC ACACACACAC ACACTAGGAT CGATCGTTAG ATGTCGAGAT    60

(2) INFORMATION FOR SEQ ID NO: 20:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 20

GAACTATATT GTCTTTCTCT GTTTTCTTGC ATGGTCACAC GTCGTTCTAG TACGCTTCTA    60

ACTTAGTGTG ATTCCACCTT CTCNAA                                        86

(2) INFORMATION FOR SEQ ID NO: 21:

(i) SEQUENCE CHARACTERISTICS:
        (A) LENGTH: 54 base pairs (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 21

AGTTTGCAGA GAAAGACAAT ATAGTTCTTK GAGAAGGTGG AATCACACTG AGTG            54

(2) INFORMATION FOR SEQ ID NO: 22:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 22

ATAGTTCTTN GAGAAGGTGG AATCACACTA AGTTAGAAG                              39

(2) INFORMATION FOR SEQ ID NO: 23:

(i) SEQUENCE CHARACTERISTICS:
            (A) LENGTH: 78 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 23

AAGTTCACGT ACGTACATAG CTAGATACAG ATTGACACAC ACACACACAC ACTAGGATCG      60

ATCGTTAGAT GTCGAGCC                                                    78

(2) INFORMATION FOR SEQ ID NO: 24:

(i) SEQUENCE CHARACTERISTICS:
            (A) LENGTH: 80 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 24

AAGTTCACGT ACGTACATAG CTAGATACAG ATTGACACAC ACACACACAC ACACTAGGAT      60

CGATCGTTAG ATGTCGAGCC                                                  80

(2) INFORMATION FOR SEQ ID NO: 25:

(i) SEQUENCE CHARACTERISTICS:

(A) LENGTH: 128 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 25

ATCTAGCTAT GTACGTACGT GAACTTTTCT TGCATGGTCA CACGTCGTTC TAGTACGCTT        60

CTAACTTTTA ACATATCTCG ACATCTAACG ATCGATCCTA GTGTGTGTGT GTGTGTGTGT       120

CAATCTGT                                                               128

(2) INFORMATION FOR SEQ ID NO: 26:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 26

CTAGATACAG ATTGACACAC ACACACACAC ACTAGGATCG ATCGTTAGAT GTCGAGAT          58

(2) INFORMATION FOR SEQ ID NO: 27:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 27

TTTTTTTTTT GCTGAGACAT GACGAGTC                                          28

(2) INFORMATION FOR SEQ ID NO: 28:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 28

AAATCTCCAA CTGGAAACTG TTCTGACTCG TCATGTCTCA GCTCTAGTAC GCTGATCTCA        60

GTCTGATCTC AGTCATTTGG TCTCAAAGTG ATTG                                   94

UNIMOLECULAR SEGMENT AMPLIFICATION AND SEQUENCING

CROSS-REFERENCE TO RELATED APPLICATIONS

This application is a continuation of, and claims the benefit of, Ser. No. 09/602,428 filed on Jun. 23, 2000, now U.S. Pat. No. 6,329,150 which is a continuation of Ser. No. 08/754,681, filed Nov. 21, 1996, now U.S. Pat. No. 6,143,495, issued Nov. 7, 2000, which is a continuation-in-part of U.S. Ser. No. 08/563,912, filed Nov. 21, 1995, now U.S. Pat. No. 5,854,033, issued Dec. 29, 1998, and claims benefit of Provisional Application Serial No. 60/016,677, filed May 1, 1996, which is abandoned, which applications are hereby incorporated herein in their entirety by reference.

BACKGROUND OF THE INVENTION

The disclosed invention is generally in the field of assays for detection of nucleic acids, and specifically in the field of nucleic acid amplification and sequencing.

A number of methods have been developed which permit the implementation of extremely sensitive diagnostic assays based on nucleic acid detection. Most of these methods employ exponential amplification of targets or probes. These include the polymerase chain reaction (PCR), ligase chain reaction (LCR), self-sustained sequence replication (3SR), nucleic acid sequence based amplification (NASBA), strand displacement amplification (SDA), and amplification with Qβ replicase (Birkenmeyer and Mushahwar, *J. Virological Methods,* 35:117–126 (1991); Landegren, *Trends Genetics,* 9:199–202 (1993)).

While all of these methods offer good sensitivity, with a practical limit of detection of about 100 target molecules, all of them suffer from relatively low precision in quantitative measurements. This lack of precision manifests itself most dramatically when the diagnostic assay is implemented in multiplex format, that is, in a format designed for the simultaneous detection of several different target sequences.

In practical diagnostic applications it is desirable to assay for many targets simultaneously. Such multiplex assays are typically used to detect five or more targets. It is also desirable to obtain accurate quantitative data for the targets in these assays. For example, it has been demonstrated that viremia can be correlated with disease status for viruses such as HIV-1 and hepatitis C (Lefrere et al., *Br. J. Haematol.,* 82(2):467471 (1992), Gunji et al., *Int. J. Cancer,* 52(5):726–730 (1992), Hagiwara et al., *Hepatology,* 17(4):545–550 (1993), Lu et al.,*J. Infect. Dis.,* 168(5):1165–8116 (1993), Piatak et al., *Science,* 259(5102):1749–1754 (1993), Gupta et al., Ninth International Conference on AIDS/Fourth STD World Congress, Jun. 7–11, 1993, Berlin, Germany, Saksela et al., *Proc. Natl. Acad. Sci. USA,* 91(3):1104–1108 (1994)). A method for accurately quantitating viral load would be useful.

In a multiplex assay, it is especially desirable that quantitative measurements of different targets accurately reflect the true ratio of the target sequences. However, the data obtained using multiplexed, exponential nucleic acid amplification methods is at best semi-quantitative. A number of factors are involved:

1. When a multiplex assay involves different priming events for different target sequences, the relative efficiency of these events may vary for different targets. This is due to the stability and structural differences between the various primers used.
2. If the rates of product strand renaturation differ for different targets, the extent of competition with priming events will not be the same for all targets.
3. For reactions involving multiple ligation events, such as LCR, there may be small but significant differences in the relative efficiency of ligation events for each target sequence. Since the ligation events are repeated many times, this effect is magnified.
4. For reactions involving reverse transcription (3SR, NASBA) or klenow strand displacement (SDA), the extent of polymerization processivity may differ among different target sequences.
5. For assays involving different replicatable RNA probes, the replication efficiency of each probe is usually not the same, and hence the probes compete unequally in replication reactions catalyzed by Qβ replicase.
6. A relatively small difference in yield in one cycle of amplification results in a large difference in amplification yield after several cycles. For example, in a PCR reaction with 25 amplification cycles and a 10% difference in yield per cycle, that is, 2-fold versus 1.8-fold amplification per cycle, the yield would be $2.0^{25}$=33,554,000 versus $1.8^{25}$= 2,408,800. The difference in overall yield after 25 cycles is 14-fold. After 30 cycles of amplification, the yield difference would be more than 20-fold.

Accordingly, there is a need for amplification methods that are less likely to produce variable and possibly erroneous signal yields in multiplex assays.

It is therefore an object of the disclosed invention to provide a method of amplifying diagnostic nucleic acids with amplification yields proportional to the amount of a target sequence in a sample.

It is another object of the disclosed invention to provide a method of detecting specific target nucleic acid sequences present in a sample where detection efficiency is not dependent on the structure of the target sequences.

It is another object of the disclosed invention to provide a method of determining the amount of specific target nucleic acid sequences present in a sample where the signal level measured is proportional to the amount of a target sequence in a sample and where the ratio of signal levels measured for different target sequences substantially matches the ratio of the amount of the different target sequences present in the sample.

It is another object of the disclosed invention to provide a method of detecting and determining the amount of multiple specific target nucleic acid sequences in a single sample where the ratio of signal levels measured for different target nucleic acid sequences substantially matches the ratio of the amount of the different target nucleic acid sequences present in the sample.

It is another object of the disclosed invention to provide a method of detecting the presence of single copies of target nucleic acid sequences in situ.

It is another object of the disclosed invention to provide a method of detecting the presence of target nucleic acid sequences representing individual alleles of a target genetic element.

It is another object of the disclosed invention to provide a method for detecting, and determining the relative amounts of, multiple molecules of interest in a sample.

It is another object of the disclosed invention to provide a method for determining the sequence of a target nucleic acid sequence.

It is another object of the present invention to provide a method of determining the range of sequences present in a mixture of target nucleic acid sequences.

SUMMARY OF THE INVENTION

Disclosed are compositions and a method for amplifying nucleic acid sequences based on the presence of a specific target sequence or analyte. The method is useful for detecting specific nucleic acids or analytes in a sample with high specificity and sensitivity. The method also has an inherently low level of background signal. Preferred embodiments of the method consist of a DNA ligation operation, an amplification operation, and, optionally, a detection operation. The DNA ligation operation circularizes a specially designed nucleic acid probe molecule. This step is dependent on hybridization of the probe to a target sequence and forms circular probe molecules in proportion to the amount of target sequence present in a sample. The amplification operation is rolling circle replication of the circularized probe. A single round of amplification using rolling circle replication results in a large amplification of the circularized probe sequences, orders of magnitude greater than a single cycle of PCR replication and other amplification techniques in which each cycle is limited to a doubling of the number of copies of a target sequence. Rolling circle amplification can also be performed independently of a ligation operation. By coupling a nucleic acid tag to a specific binding molecule, such as an antibody, amplification of the nucleic acid tag can be used to detect analytes in a sample. This is preferred for detection of analytes where an amplification target circle serves as an amplifiable tag on a reporter binding molecule, or where an amplification target circle is amplified using a rolling circle replication primer that is part of a reporter binding molecule. Optionally, an additional amplification operation can be performed on the DNA produced by rolling circle replication.

Following amplification, the amplified sequences can be detected and quantified using any of the conventional detection systems for nucleic acids such as detection of fluorescent labels, enzyme-linked detection systems, antibody-mediated label detection, and detection of radioactive labels. Since the amplified product is directly proportional to the amount of target sequence present in a sample, quantitative measurements reliably represent the amount of a target sequence in a sample. Major advantages of this method are that the ligation operation can be manipulated to obtain allelic discrimination, the amplification operation is isothermal, and signals are strictly quantitative because the amplification reaction is linear and is catalyzed by a highly processive enzyme. In multiplex assays, the primer oligonucleotide used for DNA replication can be the same for all probes.

Following amplification, the nucleotide sequence of the amplified sequences can be determined either by conventional means or by primer extension sequencing of amplified target sequence. Two preferred modes of primer extension sequencing are disclosed. Unimolecular Segment Amplification and Sequencing (USA-SEQ), a form of single nucleotide primer extension sequencing, involves interrogation of a single nucleotide in an amplified target sequence by incorporation of a specific and identifiable nucleotide based on the identity of the interrogated nucleotide. Unimolecular Segment Amplification and CAGE Sequencing (USA-CAGESEQ), a form of degenerate probe primer extension sequencing, involves sequential addition of degenerate probes to an interrogation primer hybridized to amplified target sequences. Addition of multiple probes is prevented by the presence of a removable cage at the 3' end. After addition of the degenerate probes, the cage is removed and further degenerate probes can be added or, as the final operation, the nucleotide next to the end of the interrogation primer or the last added degenerate probe is interrogated as in USA-SEQ to determine its identity. The disclosed primer extension sequencing methods are useful for identifying the presence of multiple distinct sequences in a mixture of target sequences.

The disclosed method has two features that provide simple, quantitative, and consistent amplification and detection of a target nucleic acid sequence. First, target sequences are amplified via a small diagnostic probe with an arbitrary primer binding sequence. This allows consistency in the priming and replication reactions, even between probes having very different target sequences. Second, amplification takes place not in cycles, but in a continuous, isothermal replication: rolling circle replication. This makes amplification less complicated and much more consistent in output.

Also disclosed are compositions and a method for of multiplex detection of molecules of interest involving rolling circle replication. The method is useful for simultaneously detecting multiple specific nucleic acids in a sample with high specificity and sensitivity. The method also has an inherently low level of background signal. A preferred form of the method consists of an association operation, an amplification operation, and a detection operation. The association operation involves association of one or more specially designed probe molecules, either wholly or partly nucleic acid, to target molecules of interest. This operation associates the probe molecules to a target molecules present in a sample. The amplification operation is rolling circle replication of circular nucleic acid molecules, termed amplification target circles, that are either a part of, or hybridized to, the probe molecules. A single round of amplification using rolling circle replication results in a large amplification of the amplification target circles, orders of magnitude greater than a single cycle of PCR replication and other amplification techniques in which each cycle is limited to a doubling of the number of copies of a target sequence. By coupling a nucleic acid tag to a specific binding molecule, such as an antibody, amplification of the nucleic acid tag can be used to detect analytes in a sample.

Following rolling circle replication, the amplified sequences can be detected using combinatorial multicolor coding probes that allow separate, simultaneous, and quantitative detection of multiple different amplified target sequences representing multiple different target molecules. Since the amplified product is directly proportional to the amount of target sequence present in a sample, quantitative measurements reliably represent the amount of a target sequence in a sample. Major advantages of this method are that a large number of distinct target molecules can be detected simultaneously, and that differences in the amounts of the various target molecules in a sample can be accurately quantified. It is also advantageous that the DNA replication step is isothermal, and that signals are strictly quantitative because the amplification reaction is linear and is catalyzed by a highly processive enzyme.

The disclosed method has two features that provide simple, quantitative, and consistent detection of multiple target molecules. First, amplification takes place not in cycles, but in a continuous, isothermal replication: rolling circle replication. This makes amplification less complicated and much more consistent in output. Second, combinatorial multicolor coding allows sensitive simultaneous detection of a large number different target molecules.

BRIEF DESCRIPTION OF THE DRAWINGS

FIG. 8 is a diagram of an example of ligation-mediated rolling circle replication followed by transcription (LM-RCT). Diagramed at the top is a gap oligonucleotide and an open circle probe, having a primer complement portion and a promoter portion next to the right and left target probe portions, respectively, hybridized to a target sequence. Diagramed at the bottom is the rolling circle replication product hybridized to unligated copies of the open circle probe and gap oligonucleotide. This hybridization forms the double-stranded substrate for transcription.

FIG. 9 is a diagram of an example of a multiplex antibody assay employing open circle probes and LM-RCT for generation of an amplified signal. Diagramed are three reporter antibodies, each with a different oligonucleotide as a DNA tag. Diagramed at the bottom is amplification of only that DNA tag coupled to a reporter antibody that bound.

FIG. 10 is a diagram of two schemes for multiplex detection of specific amplified nucleic acids. Diagramed at the top is hybridization of detection probes with different labels to amplified nucleic acids. Diagramed at the bottom is hybridization of amplified nucleic acid to a solid-state detector with address probes for the different possible amplification products attached in a pattern.

FIG. 11B illustrates secondary DNA strand displacement carried out simultaneously with rolling circle replication.

FIG. 12 is a diagram of an example of nested RCA using an unamplified first open circle probe as the target sequence. Diagramed at the top is a gap oligonucleotide and a first open circle probe hybridized to a target sequence, and a secondary open circle probe hybridized to the first open circle probe. Diagramed at the bottom is the rolling circle replication product of the secondary open circle probe.

FIG. 15 is a diagram of an open circle probe including a gap sequence. The lower half of the diagram illustrates a preferred relationship between sequences in the open circle probe and interrogation primers.

FIG. 16A is representative of a sample that is homozygous for the wild type sequence (indicated by incorporation of cystine). FIG. 16B is representative of a sample that is heterozygous for the wild type and a mutant (indicated by an equal number of TS-DNA molecules resulting in incorporation of cystine and adenine). FIG. 16C is representative of a sample that is homozygous but includes a few cells with a somatic mutation.

FIGS. 17A and 17B are diagrams of an example of the relationship of an open circle probe to two target sequences having a different amount of a repeating sequence. The hybridization of the left target probe and the right target probe of the open circle probe to the two different target sequences is shown (with ¦ indicating hydrogen bonding). The fill sequences are the nucleotides, complementary to the sequence in the target sequence opposite the gap space, which will fill the gap space between the left and right target probes to join the open circle probe into an amplification target circle. The sequences depicted in the diagrams relate to the assay described in Example 10. In FIG. 17A, the target sequence is SEQ ID NO:24, the left target sequence is nucleotides 76 to 96 of SEQ ID NO:25, the right target sequence is nucleotides 1 to 24 of SEQ ID NO:25, and the fill sequence is nucleotides 97 to 128 of SEQ ID NO:25. In FIG. 17B, the target sequence is SEQ ID NO:23, the left target sequence is nucleotides 2 to 21 of SEQ ID NO: 18, the right target sequence is nucleotides 1 to 24 of SEQ ID NO:25, and the fill sequence is nucleotides 22 to 51 of SEQ ID NO: 18.

FIGS. 21A, 21B, 21C, 21D, 21E, 22A, 22B, 22C, 22D, 22E, 23A, 23B, 23C, 23D, 23E, 24A, 24B, 24C, 24D, and 24E depict interrogation primers, formed from interrogation probes and degenerate probes, hybridized to TS-DNA. The figures depict five slides and TS-DNA representing a single column of five sample dots from each slide. In each row, the top (shorter) sequence is the interrogation primer and the bottom (longer) sequence is a portion of the TS-DNA. The non-underlined portions of the interrogation primers represent the interrogation probe. The underlined portions of the interrogation primers were formed by sequential ligation of one or more degenerate probes to the end of the interrogation probe. The nucleotide in boldface is the nucleotide added to the interrogation primer during primer extension. The TS-DNA sequences shown in FIGS. 21A, 21B, 21C, 21D, 21E, 22A, 22B, 22C, 22D, and 22E are related to the target sequence shown in FIG. 17A and correspond to nucleotides 1 to 60 of SEQ ID NO: 19. The interrogation primer sequences in FIGS. 21A, 21B, 21C, 21D, 21E, 22A, 22B, 22C, 22D, and 22E correspond to various portions of nucleotides 76 to 125 of SEQ ID NO:25. The sequences shown in FIGS. 23A, 23B, 23C, 23D, 23E, 24A, 24B, 24C, 24D, and 24E are related to the target sequence shown in FIG. 17B and correspond to nucleotides 1 to 58 of SEQ ID NO:26. The interrogation primer sequences in FIGS. 23A, 23B, 23C, 23D, 23E, 24A, 24B, 24C, 24D, and 24E correspond to various portions of nucleotides 1 to 50 of SEQ ID NO:18.

In FIG. 25B, an amplification target circle is shown hybridized to the oligonucleotide portion (that is, the rolling circle replication primer).

In FIG. 26B, an amplification target circle is shown hybridized to the oligonucleotide portion (that is, the rolling circle replication primer).

In FIG. 27B, an amplification target circle is shown hybridized to the oligonucleotide portion (that is, the rolling circle replication primer).

In FIG. 28B, an amplification target circle is shown hybridized to the oligonucleotide portion (that is, the rolling circle replication primer).

In FIG. 29B, an amplification target circle is shown hybridized to the oligonucleotide portion (that is, the rolling circle replication primer).

DETAILED DESCRIPTION OF THE INVENTION

The disclosed composition and method make use of certain materials and procedures which allow consistent and quantitative amplification and detection of target nucleic acid sequences. These materials and procedures are described in detail below.

Some major features of the disclosed method are:

1. The ligation operation can be manipulated to obtain allelic discrimination, especially with the use of a gap-filling step.
2. The amplification operation is isothermal.
3. Signals can be strictly quantitative because in certain embodiments of the amplification operation amplification is linear and is catalyzed by a highly processive enzyme. In multiplex assays, the primer used for DNA replication is the same for all probes.
4. Modified nucleotides or other moieties may be incorporated during DNA replication or transcription.
5. The amplification product is a repetitive DNA molecule, and may contain arbitrarily chosen tag sequences that are useful for detection.

I. Materials

A. Open Circle Probes

Figure 5:
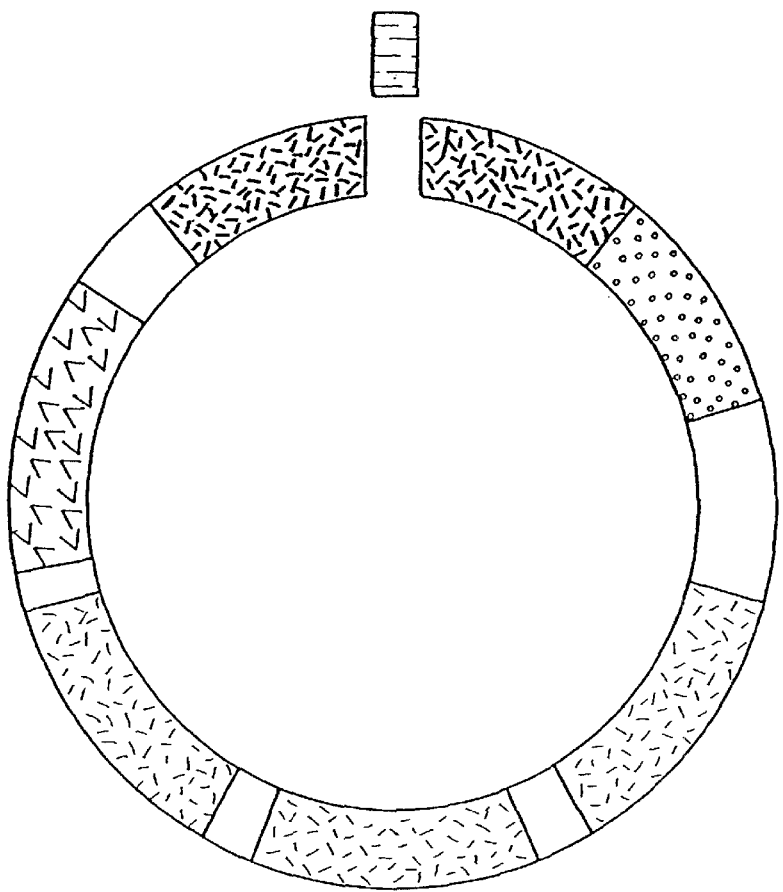
FIG. 5 is a diagram of an example of an open circle probe. Various portions of the open circle probe are indicated by different fills.

An open circle probe (OCP) is a linear single-stranded DNA molecule, generally containing between 50 to 1000 nucleotides, preferably between about 60 to 150 nucleotides, and most preferably between about 70 to 100 nucleotides. The OCP has a 5' phosphate group and a 3' hydroxyl group. This allows the ends to be ligated using a DNA ligase, or extended in a gap-filling operation. Portions of the OCP have specific functions making the OCP useful for RCA and LM-RCA. These portions are referred to as the target probe portions, the primer complement portion, the spacer region, the detection tag portions, the secondary target sequence portions, the address tag portions, and the promoter portion (FIG. 5). The target probe portions and the primer complement portion are required elements of an open circle probe. The primer complement portion is part of the spacer region. Detection tag portions, secondary target sequence portions, and promoter portions are optional and, when present, are part of the spacer region. Address tag portions are optional and, when present, may be part of the spacer region. Generally, an open circle probe is a single-stranded, linear DNA molecule comprising, from 5' end to 3' end, a 5' phosphate group, a right target probe portion, a spacer region, a left target probe portion, and a 3' hydroxyl group, with a primer complement portion present as part of the spacer region. Those segments of the spacer region that do not correspond to a specific portion of the OCP can be arbitrarily chosen sequences. It is preferred that OCPs do not have any sequences that are self-complementary. It is considered that this condition is met if there are no complementary regions greater than six nucleotides long without a mismatch or gap. It is also preferred that OCPs containing a promoter portion do not have any sequences that resemble a transcription terminator, such as a run of eight or more thymidine nucleotides.

The open circle probe, when ligated and replicated, gives rise to a long DNA molecule containing multiple repeats of sequences complementary to the open circle probe. This long DNA molecule is referred to herein as tandem sequences DNA (TS-DNA). TS-DNA contains sequences complementary to the target probe portions, the primer complement portion, the spacer region, and, if present on the open circle probe, the detection tag portions, the secondary target sequence portions, the address tag portions, and the promoter portion. These sequences in the TS-DNA are referred to as target sequences (which match the original target sequence), primer sequences (which match the sequence of the rolling circle replication primer), spacer sequences (complementary to the spacer region), detection tags, secondary target sequences, address tags, and promoter sequences.

A particularly preferred embodiment is an open circle probe of 70 to 100 nucleotides including a left target probe of 20 nucleotides and a right target probe of 20 nucleotides. The left target probe and right target probe hybridize to a target sequence leaving a gap of five nucleotides, which is filled by a single pentanucleotide gap oligonucleotide.

1. Target Probe Portions

There are two target probe portions on each OCP, one at each end of the OCP. The target probe portions can each be any length that supports specific and stable hybridization between the target probes and the target sequence. For this purpose, a length of 10 to 35 nucleotides for each target probe portion is preferred, with target probe portions 15 to 20 nucleotides long being most preferred. The target probe portion at the 3' end of the OCP is referred to as the left target probe, and the target probe portion at the 5' end of the OCP is referred to as the right target probe. These target probe portions are also referred to herein as left and right target probes or left and right probes. The target probe portions are complementary to a target nucleic acid sequence.

Figure 1:
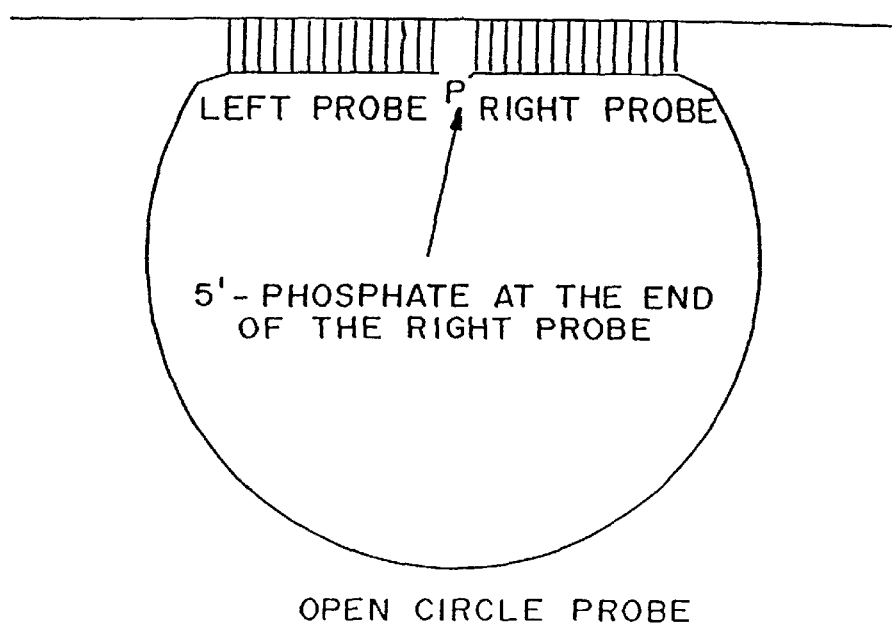
FIG. 1 is a diagram of an example of an open circle probe hybridized to a target sequence. The diagram shows the relationship between the target sequence and the right and left target probes.
Figure 2:
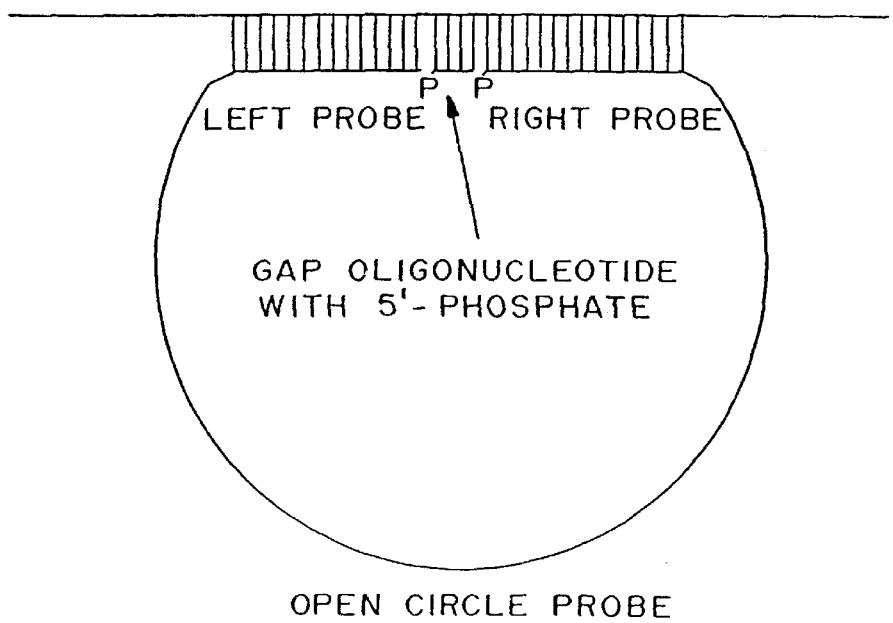
FIG. 2 is a diagram of an example of a gap oligonucleotide and an open circle probe hybridized to a target sequence. The diagram shows the relationship between the target sequence, the gap oligonucleotide, and the right and left target probes.
Figure 3:
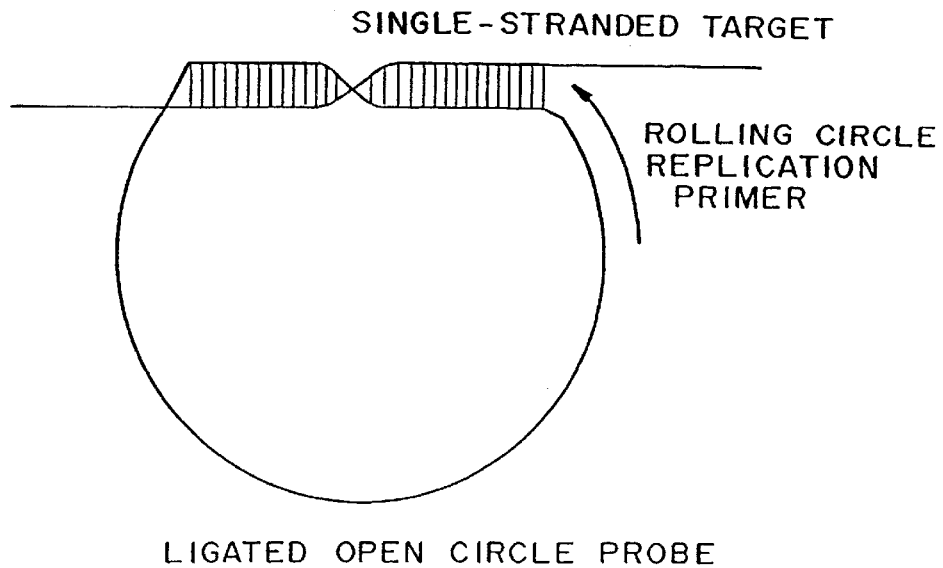
FIG. 3 is a diagram of an open circle probe hybridized and ligated to a target sequence. The diagram shows how the open circle probe becomes topologically locked to the target sequence.

The target probe portions are complementary to the target sequence, such that upon hybridization the 5' end of the right target probe portion and the 3' end of the left target probe portion are base-paired to adjacent nucleotides in the target sequence, with the objective that they serve as a substrate for ligation (FIG. 1). Optionally, the 5' end and the 3' end of the target probe portions may hybridize in such a way that they are separated by a gap space. In this case the 5' end and the 3' end of the OCP may only be ligated if one or more additional oligonucleotides, referred to as gap oligonucleotides, are used, or if the gap space is filled during the ligation operation. The gap oligonucleotides hybridize to the target sequence in the gap space to a form continuous probe/target hybrid (FIG. 2). The gap space may be any length desired but is generally ten nucleotides or less. It is preferred that the gap space is between about three to ten nucleotides in length, with a gap space of four to eight nucleotides in length being most preferred. Alternatively, a gap space could be filled using a DNA polymerase during the ligation operation (see Example 3). When using such a gap-filling operation, a gap space of three to five nucleotides in length is most preferred. As another alternative, the gap space can be partially bridged by one or more gap oligonucleotides, with the remainder of the gap filled using DNA polymerase.

2. Primer Complement Portion

The primer complement portion is part of the spacer region of an open circle probe. The primer complement portion is complementary to the rolling circle replication primer (RCRP). Each OCP should have a single primer complement portion. This allows rolling circle replication to initiate at a single site on ligated OCPs. The primer complement portion and the cognate primer can have any desired sequence so long as they are complementary to each other. In general, the sequence of the primer complement can be chosen such that it is not significantly similar to any other portion of the OCP. The primer complement portion can be any length that supports specific and stable hybridization between the primer complement portion and the primer. For this purpose, a length of 10 to 35 nucleotides is preferred, with a primer complement portion 16 to 20 nucleotides long being most preferred. The primer complement portion can be located anywhere within the spacer region of an OCP. It is preferred that the primer complement portion is adjacent to the right target probe, with the right target probe portion and the primer complement portion preferably separated by three to ten nucleotides, and most preferably separated by six nucleotides. This location prevents the generation of any other spacer sequences, such as detection tags and secondary target sequences, from unligated open circle probes during DNA replication.

3. Detection Tag Portions

Detection tag portions are part of the spacer region of an open circle probe. Detection tag portions have sequences matching the sequence of the complementary portion of detection probes. These detection tag portions, when amplified during rolling circle replication, result in TS-DNA having detection tag sequences that are complementary to the complementary portion of detection probes. If present, there may be one, two, three, or more than three detection tag portions on an OCP. It is preferred that an OCP have two, three or four detection tag portions. Most preferably, an OCP will have three detection tag portions. Generally, it is preferred that an OCP have 60 detection tag portions or less. There is no fundamental limit to the number of detection tag portions that can be present on an OCP except the size of the OCP. When there are multiple detection tag portions, they may have the same sequence or they may have different sequences, with each different sequence complementary to a different detection probe. It is preferred that an OCP contain detection tag portions that have the same sequence such that they are all complementary to a single detection probe. For some multiplex detection methods, it is preferable that OCPs contain up to six detection tag portions and that the detection tag portions have different sequences such that each of the detection tag portions is complementary to a different detection probe. The detection tag portions can each be any length that supports specific and stable hybridization between the detection tags and the detection probe. For this purpose, a length of 10 to 35 nucleotides is preferred, with a detection tag portion 15 to 20 nucleotides long being most preferred.

4. Secondary Target Sequence Portions

Secondary target sequence portions are part of the spacer region of an open circle probe. Secondary target sequence portions have sequences matching the sequence of target probes of a secondary open circle probe. These secondary target sequence portions, when amplified during rolling circle replication, result in TS-DNA having secondary target sequences that are complementary to target probes of a secondary open circle probe. If present, there may be one, two, or more than two secondary target sequence portions on an OCP. It is preferred that an OCP have one or two secondary target sequence portions. Most preferably, an OCP will have one secondary target sequence portion. Generally, it is preferred that an OCP have 50 secondary target sequence portions or less. There is no fundamental limit to the number of secondary target sequence portions that can be present on an OCP except the size of the OCP. When there are multiple secondary target sequence portions, they may have the same sequence or they may have different sequences, with each different sequence complementary to a different secondary OCP. It is preferred that an OCP contain secondary target sequence portions that have the same sequence such that they are all complementary to a single target probe portion of a secondary OCP. The secondary target sequence portions can each be any length that supports specific and stable hybridization between the secondary target sequence and the target sequence probes of its cognate OCP. For this purpose, a length of 20 to 70 nucleotides is preferred, with a secondary target sequence portion 30 to 40 nucleotides long being most preferred. As used herein, a secondary open circle probe is an open circle probe where the target probe portions match or are complementary to secondary target sequences in another open circle probe or an amplification target circle. It is contemplated that a secondary open circle probe can itself contain secondary target sequences that match or are complementary to the target probe portions of another secondary open circle probe. Secondary open circle probes related to each other in this manner are referred to herein as nested open circle probes.

5. Address Tag Portion

Figures 6, 7:
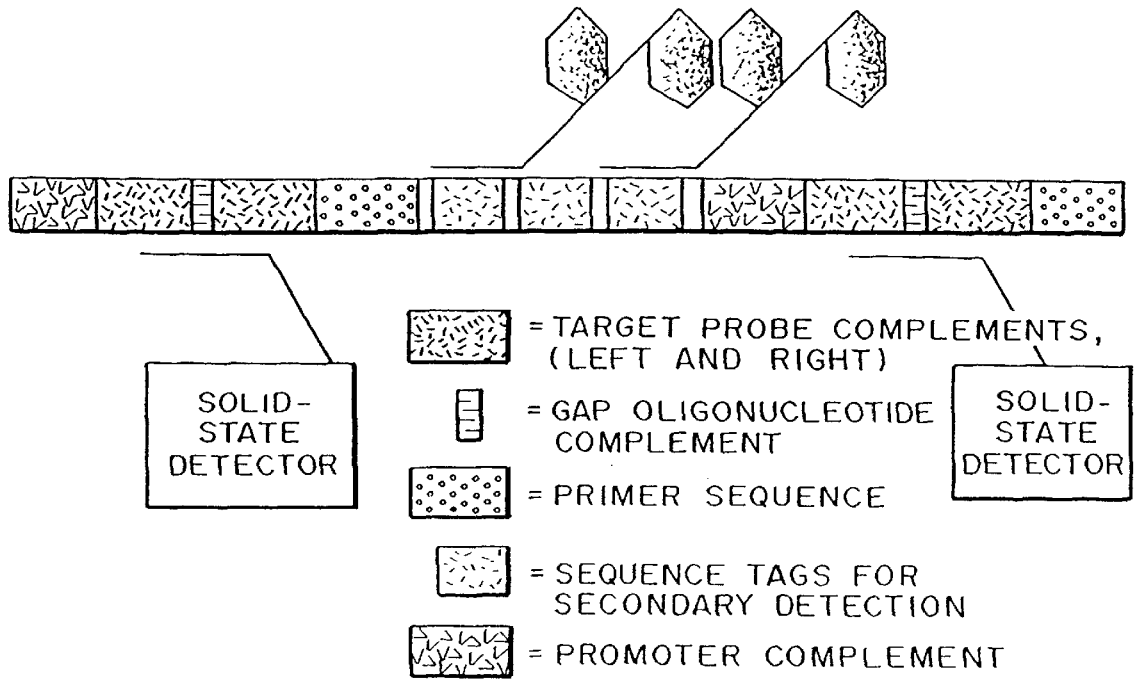
FIG. 6 is a diagram of tandem sequence DNA (TS-DNA) and an address probe designed to hybridize to the portion of the TS-DNA corresponding to part of the right and left target probes of the open circle probe and the gap oligonucleotide. The TS-DNA is SEQ ID NO:2 and the address probe is SEQ ID NO:3.
FIG. 7 is a diagram of the capture and detection of TS-DNA. Capture is effected by hybridization of the TS-DNA to address probes attached to a solid-state detector. Detection is effected by hybridization of secondary detection probes to the captured TS-DNA. Portions of the TS-DNA corresponding to various portions of the open circle probe are indicated by different fills.

The address tag portion is part of either the target probe portions or the spacer region of an open circle probe. The address tag portion has a sequence matching the sequence of the complementary portion of an address probe. This address tag portion, when amplified during rolling circle replication, results in TS-DNA having address tag sequences that are complementary to the complementary portion of address probes. If present, there may be one, or more than one, address tag portions on an OCP. It is preferred that an OCP have one or two address tag portions. Most preferably, an OCP will have one address tag portion. Generally, it is preferred that an OCP have 50 address tag portions or less. There is no fundamental limit to the number of address tag portions that can be present on an OCP except the size of the OCP. When there are multiple address tag portions, they may have the same sequence or they may have different sequences, with each different sequence complementary to a different address probe. It is preferred that an OCP contain address tag portions that have the same sequence such that they are all complementary to a single address probe. Preferably, the address tag portion overlaps all or a portion of the target probe portions, and all of any intervening gap space (FIG. 6). Most preferably, the address tag portion overlaps all or a portion of both the left and right target probe portions. The address tag portion can be any length that supports specific and stable hybridization between the address tag and the address probe. For this purpose, a length between 10 and 35 nucleotides long is preferred, with an address tag portion 15 to 20 nucleotides long being most preferred.

6. Promoter Portion

The promoter portion corresponds to the sequence of an RNA polymerase promoter. A promoter portion can be included in an open circle probe so that transcripts can be generated from TS-DNA. The sequence of any promoter may be used, but simple promoters for RNA polymerases without complex requirements are preferred. It is also preferred that the promoter is not recognized by any RNA polymerase that may be present in the sample containing the target nucleic acid sequence. Preferably, the promoter portion corresponds to the sequence of a T7 or SP6 RNA polymerase promoter. The T7 and SP6 RNA polymerases are highly specific for particular promoter sequences. Other promoter sequences specific for RNA polymerases with this characteristic would also be preferred. Because promoter sequences are generally recognized by specific RNA polymerases, the cognate polymerase for the promoter portion of the OCP should be used for transcriptional amplification. Numerous promoter sequences are known and any promoter specific for a suitable RNA polymerase can be used. The promoter portion can be located anywhere within the spacer region of an OCP and can be in either orientation. Preferably, the promoter portion is immediately adjacent to the left target probe and is oriented to promote transcription toward the 3' end of the open circle probe. This orientation results in transcripts that are complementary to TS-DNA, allowing independent detection of TS-DNA and the transcripts, and prevents transcription from interfering with rolling circle replication.

B. Gap Oligonucleotides

Gap oligonucleotides are oligonucleotides that are complementary to all or a part of that portion of a target sequence which covers a gap space between the ends of a hybridized open circle probe. An example of a gap oligonucleotide and its relationship to a target sequence and open circle probe is shown in FIG. 2. Gap oligonucleotides have a phosphate group at their 5' ends and a hydroxyl group at their 3' ends. This facilitates ligation of gap oligonucleotides to open circle probes, or to other gap oligonucleotides. The gap space between the ends of a hybridized open circle probe can be filled with a single gap oligonucleotide, or it can be filled with multiple gap oligonucleotides. For example, two 3 nucleotide gap oligonucleotides can be used to fill a six nucleotide gap space, or a three nucleotide gap oligonucleotide and a four nucleotide gap oligonucleotide can be used to fill a seven nucleotide gap space. Gap oligonucleotides are particularly useful for distinguishing between closely related target sequences. For example, multiple gap oligonucleotides can be used to amplify different allelic variants of a target sequence. By placing the region of the target sequence in which the variation occurs in the gap space formed by an open circle probe, a single open circle probe can be used to amplify each of the individual variants by using an appropriate set of gap oligonucleotides.

C. Amplification Target Circles

An amplification target circle (ATC) is a circular single-stranded DNA molecule, generally containing between 40 to 1000 nucleotides, preferably between about 50 to 150 nucleotides, and most preferably between about 50 to 100 nucleotides. Portions of ATCs have specific functions making the ATC useful for rolling circle amplification (RCA). These portions are referred to as the primer complement portion, the detection tag portions, the secondary target sequence portions, the address tag portions, and the promoter portion. The primer complement portion is a required element of an amplification target circle. Detection tag portions, secondary target sequence portions, address tag portions, and promoter portions are optional. Generally, an amplification target circle is a single-stranded, circular DNA molecule comprising a primer complement portion. Those segments of the ATC that do not correspond to a specific portion of the ATC can be arbitrarily chosen sequences. It is preferred that ATCs do not have any sequences that are self-complementary. It is considered that this condition is met if there are no complementary regions greater than six nucleotides long without a mismatch or gap. It is also preferred that ATCs containing a promoter portion do not have any sequences that resemble a transcription terminator, such as a run of eight or more thymidine nucleotides. Ligated open circle probes are a type of ATC, and as used herein the term amplification target circle includes ligated open circle probes. An ATC can be used in the same manner as described herein for OCPs that have been ligated.

An amplification target circle, when replicated, gives rise to a long DNA molecule containing multiple repeats of sequences complementary to the amplification target circle. This long DNA molecule is referred to herein as tandem sequences DNA (TS-DNA). TS-DNA contains sequences complementary to the primer complement portion and, if present on the amplification target circle, the detection tag portions, the secondary target sequence portions, the address tag portions, and the promoter portion. These sequences in the TS-DNA are referred to as primer sequences (which match the sequence of the rolling circle replication primer), spacer sequences (complementary to the spacer region), detection tags, secondary target sequences, address tags, and promoter sequences. Amplification target circles are useful as tags for specific binding molecules.

D. Rolling Circle Replication Primer

A rolling circle replication primer (RCRP) is an oligonucleotide having sequence complementary to the primer complement portion of an OCP or ATC. This sequence is referred to as the complementary portion of the RCRP. The complementary portion of a RCRP and the cognate primer complement portion can have any desired sequence so long as they are complementary to each other. In general, the sequence of the RCRP can be chosen such that it is not significantly complementary to any other portion of the OCP or ATC. The complementary portion of a rolling circle replication primer can be any length that supports specific and stable hybridization between the primer and the primer complement portion. Generally this is 10 to 35 nucleotides long, but is preferably 16 to 20 nucleotides long.

It is preferred that rolling circle replication primers also contain additional sequence at the 5' end of the RCRP that is not complementary to any part of the OCP or ATC. This sequence is referred to as the non-complementary portion of the RCRP. The non-complementary portion of the RCRP, if present, serves to facilitate strand displacement during DNA replication. The non-complementary portion of a RCRP may be any length, but is generally 1 to 100 nucleotides long, and preferably 4 to 8 nucleotides long. The rolling circle replication primer may also include modified nucleotides to make it resistant to exonuclease digestion. For example, the primer can have three or four phosphorothioate linkages between nucleotides at the 5' end of the primer. Such nuclease resistant primers allow selective degradation of excess unligated OCP and gap oligonucleotides that might otherwise interfere with hybridization of detection probes, address probes, and secondary OCPs to the amplified nucleic acid. A rolling circle replication primer can be used as the tertiary DNA strand displacement primer in strand displacement cascade amplification.

E. Detection Labels

To aid in detection and quantitation of nucleic acids amplified using RCA and RCT, detection labels can be directly incorporated into amplified nucleic acids or can be coupled to detection molecules. As used herein, a detection label is any molecule that can be associated with amplified nucleic acid, directly or indirectly, and which results in a measurable, detectable signal, either directly or indirectly. Many such labels for incorporation into nucleic acids or coupling to nucleic acid or antibody probes are known to those of skill in the art. Examples of detection labels suitable for use in RCA and RCT are radioactive isotopes, fluorescent molecules, phosphorescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels for combinatorial multicolor coding are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, Oreg. and Research Organics, Cleveland, Ohio.

Labeled nucleotides are preferred form of detection label since they can be directly incorporated into the products of RCA and RCT during synthesis. Examples of detection labels that can be incorporated into amplified DNA or RNA include nucleotide analogs such as BrdUrd (Hoy and Schimke, *Mutation Research* 290:217–230 (1993)), BrUTP (Wansick et al., *J. Cell Biology* 122:283–293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226–3232 (1994)). A preferred nucleotide analog detection label for DNA is BrdUrd (BUDR triphosphate, Sigma), and a preferred nucleotide analog detection label for RNA is Biotin-16-uridine-5'-triphosphate (Biotin-16-dUTP, Boehringher Mannheim). Fluorescein, Cy3, and Cy5 can be linked to dUTP for direct labelling. Cy3.5 and Cy7 are available as avidin or anti-digoxygenin conjugates for secondary detection of biotin- or digoxygenin-labelled probes.

Detection labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [$3.3.1.1^{3,7}$]decane]-4-yl) phenyl phosphate; Tropix, Inc.).

A preferred detection label for use in detection of amplified RNA is acridinium-ester-labeled DNA probe (GenProbe, Inc., as described by Arnold et al., *Clinical Chemistry* 35:1588–1594 (1989)). An acridinium-ester-labeled detection probe permits the detection of amplified RNA without washing because unhybridized probe can be destroyed with alkali (Arnold et al. (1989)).

Molecules that combine two or more of these detection labels are also considered detection labels. Any of the known detection labels can be used with the disclosed probes, tags, and method to label and detect nucleic acid amplified using the disclosed method. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. Such methods can be used directly in the disclosed method of amplification and detection. As used herein, detection molecules are molecules which interact with amplified nucleic acid and to which one or more detection labels are coupled.

F. Detection Probes

Detection probes are labeled oligonucleotides having sequence complementary to detection tags on TS-DNA or transcripts of TS-DNA. The complementary portion of a detection probe can be any length that supports specific and stable hybridization between the detection probe and the detection tag. For this purpose, a length of 10 to 35 nucleotides is preferred, with a complementary portion of a detection probe 16 to 20 nucleotides long being most preferred. Detection probes can contain any of the detection labels described above. Preferred labels are biotin and fluorescent molecules. A particularly preferred detection probe is a molecular beacon. Molecular beacons are detection probes labeled with fluorescent moieties where the fluorescent moieties fluoresce only when the detection probe is hybridized (Tyagi and Kramer, *Nature Biotechnology* 14:303–308 (1996)). The use of such probes eliminates the need for removal of unhybridized probes prior to label detection because the unhybridized detection probes will not produce a signal. This is especially useful in multiplex assays.

A preferred form of detection probe, referred to herein as a collapsing detection probe, contains two separate complementary portions. This allows each detection probe to hybridize to two detection tags in TS-DNA. In this way, the detection probe forms a bridge between different parts of the TS-DNA. The combined action of numerous collapsing detection probes hybridizing to TS-DNA will be to form a collapsed network of cross-linked TS-DNA. Collapsed TS-DNA occupies a much smaller volume than free, extended TS-DNA, and includes whatever detection label present on the detection probe. This result is a compact and discrete detectable signal for each TS-DNA. Collapsing TS-DNA is useful both for in situ hybridization applications and for multiplex detection because it allows detectable signals to be spatially separate even when closely packed. Collapsing TS-DNA is especially preferred for use with combinatorial multicolor coding.

TS-DNA collapse can also be accomplished through the use of ligand/ligand binding pairs (such as biotin and avidin) or hapten/antibody pairs. As described in Example 6, a nucleotide analog, BUDR, can be incorporated into TS-DNA during rolling circle replication. When biotinylated antibodies specific for BUDR and avidin are added, a cross-linked network of TS-DNA forms, bridged by avidin-biotin-antibody conjugates, and the TS-DNA collapses into a compact structure. Collapsing detection probes and biotin-mediated collapse can also be used together to collapse TS-DNA.

G. Address Probes

An address probe is an oligonucleotide having a sequence complementary to address tags on TS-DNA or transcripts of TS-DNA. The complementary portion of an address probe can be any length that supports specific and stable hybridization between the address probe and the address tag. For this purpose, a length of 10 to 35 nucleotides is preferred, with a complementary portion of an address probe 12 to 18 nucleotides long being most preferred. Preferably, the complementary portion of an address probe is complementary to all or a portion of the target probe portions of an OCP. Most preferably, the complementary portion of an address probe is complementary to a portion of either or both of the left and right target probe portions of an OCP and all or a part of any gap oligonucleotides or gap sequence created in a gap-filling operation (see FIG. 6). Address probe can contain a single complementary portion or multiple complementary portions. Preferably, address probes are coupled, either directly or via a spacer molecule, to a solid-state support. Such a combination of address probe and solid-state support are a preferred form of solid-state detector.

H. DNA Strand Displacement Primers

Primers used for secondary DNA strand displacement are referred to herein as DNA strand displacement primers. One form of DNA strand displacement primer, referred to herein as a secondary DNA strand displacement primer, is an oligonucleotide having sequence matching part of the sequence of an OCP or ATC. This sequence is referred to as the matching portion of the secondary DNA strand displacement primer. This matching portion of a secondary DNA strand displacement primer is complementary to sequences in TS-DNA. The matching portion of a secondary DNA strand displacement primer may be complementary to any sequence in TS-DNA. However, it is preferred that it not be complementary TS-DNA sequence matching either the rolling circle replication primer or a tertiary DNA strand displacement primer, if one is being used. This prevents hybridization of the primers to each other. The matching portion of a secondary DNA strand displacement primer may be complementary to all or a portion of the target sequence. In this case, it is preferred that the 3' end nucleotides of the secondary DNA strand displacement primer are complementary to the gap sequence in the target sequence. It is most preferred that nucleotide at the 3' end of the secondary DNA strand displacement primer falls complementary to the last nucleotide in the gap sequence of the target sequence, that is, the 5' nucleotide in the gap sequence of the target sequence. The matching portion of a secondary DNA strand displacement primer can be any length that supports specific and stable hybridization between the primer and its complement. Generally this is 12 to 35 nucleotides long, but is preferably 18 to 25 nucleotides long.

It is preferred that secondary DNA strand displacement primers also contain additional sequence at their 5' end that does not match any part of the OCP or ATC. This sequence is referred to as the non-matching portion of the secondary DNA strand displacement primer. The non-matching portion of the secondary DNA strand displacement primer, if present, serves to facilitate strand displacement during DNA replication. The non-matching portion of a secondary DNA strand displacement primer may be any length, but is generally 1 to 100 nucleotides long, and preferably 4 to 8 nucleotides long.

Another form of DNA strand displacement primer, referred to herein as a tertiary DNA strand displacement primer, is an oligonucleotide having sequence complementary to part of the sequence of an OCP or ATC. This sequence is referred to as the complementary portion of the tertiary DNA strand displacement primer. This complementary portion of the tertiary DNA strand displacement primer matches sequences in TS-DNA. The complementary portion of a tertiary DNA strand displacement primer may be complementary to any sequence in the OCP or ATC. However, it is preferred that it not be complementary OCP or ATC sequence matching the secondary DNA strand displacement primer. This prevents hybridization of the primers to each other. Preferably, the complementary portion of the tertiary DNA strand displacement primer has sequence complementary to a portion of the spacer portion of an OCP. The complementary portion of a tertiary DNA strand displacement primer can be any length that supports specific and stable hybridization between the primer and its complement. Generally this is 12 to 35 nucleotides long, but is preferably 18 to 25 nucleotides long. It is preferred that tertiary DNA strand displacement primers also contain additional sequence at their 5' end that is not complementary to any part of the OCP or ATC. This sequence is referred to as the non-complementary portion of the tertiary DNA strand displacement primer. The non-complementary portion of the tertiary DNA strand displacement primer, if present, serves to facilitate strand displacement during DNA replication. The non-complementary portion of a tertiary DNA strand displacement primer may be any length, but is generally 1 to 100 nucleotides long, and preferably 4 to 8 nucleotides long. A rolling circle replication primer is a preferred form of tertiary DNA strand displacement primer.

DNA strand displacement primers may also include modified nucleotides to make them resistant to exonuclease digestion. For example, the primer can have three or four phosphorothioate linkages between nucleotides at the 5' end of the primer. Such nuclease resistant primers allow selective degradation of excess unligated OCP and gap oligonucleotides that might otherwise interfere with hybridization of detection probes, address probes, and secondary OCPs to the amplified nucleic acid. DNA strand displacement primers can be used for secondary DNA strand displacement and strand displacement cascade amplification, both described below.

I. Interrogation Probes

An interrogation probe is an oligonucleotide having a sequence complementary to portions of TS-DNA or transcripts of TS-DNA. Interrogation probes are intended for use in primer extension sequencing operations following rolling circle amplification of an OCP or amplification target circle (for example, USA-SEQ and USA-CAGESEQ). Interrogation probes can be used directly as interrogation primers in a primer extension sequencing operation, or they can be combined with other interrogation probes or with degenerate probes to form interrogation primers. As use herein, interrogation primers are oligonucleotides serving as primers for primer extension sequencing. The relationship of interrogation probes to sequences in OCPs or ATCs (and, therefore, in amplified target sequences) is preferably determined by the relationship of the interrogation primer (which is formed from the interrogation probe) to sequences in OCPs or ATCs.

The complementary portion of an interrogation probe can be any length that supports hybridization between the interrogation probe and TS-DNA. For this purpose, a length of 10 to 40 nucleotides is preferred, with a complementary portion of an interrogation probe 15 to 30 nucleotides long being most preferred. The preferred use of interrogation probes is to form interrogation primers for primer extension sequencing of an amplified target sequence. For this purpose, interrogation probes should hybridize to TS-DNA 5' of the portion of the amplified target sequences that are to be sequenced.

For primer extension sequencing operations (for example, USA-CAGESEQ), it is preferred that a nested set of interrogation probes are designed to hybridize just 5' to a region of amplified target sequence for which the sequence is to be determined. Thus, for example, a set of interrogation probes can be designed where each probe is complementary to a nucleotide region of the target sequence with each 20 nucleotide region offset from the previous region by one nucleotide. This preferred relationship can be illustrated as follows:

```
Probe 1  TCTCGACATCTAACGATCGA
Probe 2   CTCGACATCTAACGATCGAT
Probe 3    TCGACATCTAACGATCGATC
Probe 4     CGACATCTAACGATCGATCC
Probe 5      GACATCTAACGATCGATCCT
             ||||||||||||||||||||
             ||||||||||||||||||||
Target   TAGAGCTGTAGATTGCTAGCTAGGATCACACACACACACACA
```

Probe 1 is nucleotides 76 to 95 of SEQ ID NO:25, probe 2 is nucleotides 77 to 96 of SEQ ID NO:25, probe 3 is nucleotides 78 to 97 of SEQ ID NO:25, probe 4 is nucleotides 79 to 98 of SEQ ID NO:25, probe 5 is nucleotides 80 to 99 of SEQ ID NO:25, and the target (shown 3' to 5') is nucleotides 19 to 60 of SEQ ID NO: 19. It is preferred that the number of interrogation probes in such a nested set be equal to the length of the degenerate probes used in the primer extension sequencing operation.

It is also preferred that the 3' hydroxyl of interrogation probes be reversibly blocked in order to prevent unwanted ligation to other oligonucleotides. Such blocked probes allow controlled ligation of additional probes, such as degenerate probes, to an interrogation probe. For example, USA-CAGESEQ, a form of degenerate probe primer extension sequencing, makes use of reversibly blocked interrogation probes to allow sequential, and controlled, addition of degenerate probes to interrogation probes. Any of the known means of reversibly blocking 3'-hydroxyls in oligonucleotides can be used to produce blocked interrogation probes. Preferred forms of reversible blocking elements are the cage structures described below. Caged oligonucleotides useful as blocked interrogation probes are described below.

J. Degenerate Probes

Degenerate probes are oligonucleotides intended for use in primer extension sequencing operations following rolling circle amplification of an OCP or amplification target circle (for example, USA-SEQ and USA-CAGESEQ). Degenerate probes are combined with interrogation probes to form interrogation primers. This is accomplished by hybridizing an interrogation probe and degenerate primers to TS-DNA and ligating together the interrogation probe and whichever degenerate probe that is hybridized adjacent to the interrogation probe. For this purpose, it is preferred that a full set of degenerate probes be used together. This ensures that at least one of the degenerate probes will be complementary to the portion of TS-DNA immediately adjacent to a hybridized interrogation probe. This preferred relationship can be illustrated as follows:

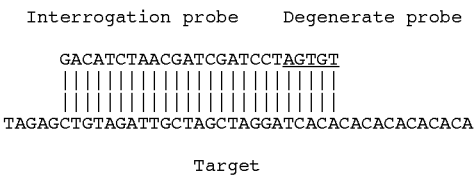

```
Interrogation probe    Degenerate probe

GACATCTAACGATCGATCCTAGTGT
    |||||||||||||||||||||||||
    |||||||||||||||||||||||||
    TAGAGCTGTAGATTGCTAGCTAGGATCACACACACACACA

Target
```

The interrogation probe and degenerate probe together represent nucleotides 80 to 104 of SEQ ID NO:25, and the target (shown 3' to 5') is nucleotides 19 to 60 of SEQ ID NO:19. The underlined sequence represents the degenerate probe which is ligated to the interrogation probe (non-underlined portion of the top sequence).

It is preferred that a full set of degenerate probes be used in primer extension sequencing operations involving degenerate probes. As used herein, a full set of degenerate probes refers to a set of oligonucleotides, all of the same length, where every possible nucleotide sequence is represented. The number of such probes is described by the formula $4^N$ where 4 represents the four types of nucleotides found in DNA (or in RNA) and N is the length of the oligonucleotides in the set. Thus, a full set of degenerate probes three nucleotides in length would include 64 different oligonucleotides, a full set of degenerate probes four nucleotides in length would include 256 different oligonucleotides, and a full set of degenerate probes five nucleotides in length would include 1024 different oligonucleotides. It is preferred that the number of interrogation probes in such a nested set be equal to the length of the degenerate probes used in degenerate probe primer extension sequencing. Sets of degenerate probes can be used with a single interrogation probe or with sets of interrogation probes. It is preferred that such sets of interrogation probes represent a nested set as described above.

In a primer extension operation, only one of the degenerate probes in a set of degenerate probes will hybridize adjacent to a given interrogation probe hybridized to an amplified target sequence. The nucleotide sequence adjacent to (that is, 3' of) the region of the target sequence hybridized to the interrogation probe determines which degenerate probe will hybridize. Only degenerate probes hybridized immediately adjacent to the interrogation probe should be ligated to the interrogation probe. For this reason, it is preferred that the region of the target sequence to be sequenced is adjacent to the region hybridized to the interrogation probe. Preferably, this region is a gap sequence in TS-DNA (representing all or a portion of a filled gap space). The use of gap-filling ligation allows the presence of gap sequences in TS-DNA representing a potential, expected, or known region of sequence variability in the target nucleic aid which is amplified in RCA.

Degenerate probes can be combined with interrogation probes or with other degenerate probes to form interrogation primers. As used herein, interrogation primers are oligonucleotides serving as primers for primer extension sequencing.

It is also preferred that the 3' hydroxyl of degenerate probes be reversibly blocked in order to prevent unwanted ligation to other oligonucleotides. Such blocked probes allow controlled ligation of additional degenerate probes to a degenerate probe. For example, USA-CAGESEQ makes use of reversibly blocked degenerate probes to allow sequential, and controlled, addition of the degenerate probes to interrogation probes. Any of the known means of reversibly blocking 3'-hydroxyls in oligonucleotides can be used to produce blocked degenerate probes. Preferred forms of reversible blocking elements are the cage structures described below. Caged oligonucleotides useful as blocked degenerate probes are described below.

Where a nested set of interrogation probes are used, they can be used in a set of primer extension sequencing operations to determine the identity of adjacent nucleotides. Using the set of interrogation probes illustrated above, and a full set of pentamer degenerate probes, the highlighted nucleotides in the target sequence can be identified where a single degenerate probe is ligated to each of the interrogation probes:

```
Probe 1   TCTCGACATCTAACGATCGA
Probe 2    CTCGACATCTAACGATCGAT
Probe 3     TCGACATCTAACGATCGATC
Probe 4      CGACATCTAACGATCGATCC
Probe 5       GACATCTAACGATCGATCCT
              ||||||||||||||||||||
              ||||||||||||||||||||
Target    TAGAGCTGTAGATTGCTAGCTAGGATCACACACACACACACA
```

Probe 1 is nucleotides 76 to 95 of SEQ ID NO:25, probe 2 is nucleotides 77 to 96 of SEQ ID NO:25, probe 3 is nucleotides 78 to 97 of SEQ ID NO:25, probe 4 is nucleotides 79 to 98 of SEQ ID NO:25, probe 5 is nucleotides 80 to 99 of SEQ ID NO:25, and the target (shown 3' to 5') is nucleotides 19 to 60 of SEQ ID NO: 19. The highlighted nucleotides represent the nucleotides adjacent to (that is, 3' of) the interrogation primers formed by the ligation of the interrogation probes and the degenerate primers. The identity of additional nucleotides can be determined by ligating additional degenerate probes to the degenerate probes already ligated to the interrogation probes. This process is illustrated Example 10. It is preferred that the length of the degenerate probes be equal to the number of interrogation probes in a nested set.

K. Interrogation Primers

An interrogation primer is an oligonucleotide having a sequence complementary to portions of TS-DNA or transcripts of TS-DNA. Interrogation primers are intended for use in primer extension sequencing operations following rolling circle amplification of an amplification target circle (for example, USA-SEQ and USA-CAGESEQ). Preferably, an interrogation primer is complementary to a portion of the target sequences in TS-DNA representing all or a portion of the left target probe portion of an OCP. For use with secondary TS-DNA, it is preferred that interrogation primers are complementary to a portion of the target sequences in secondary TS-DNA representing the right target probe portion of an OCP. Such interrogation primers are also preferably complementary to a portion of the spacer region adjacent to the left target probe portion. Thus, preferred interrogation primers are complementary to a contiguous segment of TS-DNA representing the 5' end of the OCP. This preferred relationship allows primer extension sequencing of gap sequences in TS-DNA. An example of this preferred relationship between interrogation primers and an OCP is shown in FIG. 15. An interrogation probe can, however, be complementary to any desired sequence in amplified nucleic acid.

In general, interrogation primers can be an unligated interrogation probe, a combination of two or more interrogation probes (that is, interrogation probes ligated together), or a combination of one or more interrogation probes and one or more degenerate probes (that is, interrogation probes and degenerate probes ligated together). Thus, interrogation probes can be used directly as interrogation primers in a primer extension sequencing operation, or they can be combined with other interrogation probes or with degenerate probes to form interrogation primers. As use herein, interrogation primers are oligonucleotides serving as primers for primer extension sequencing. Where an interrogation primer is made from probes with blocked 3'-hydroxyls, and the resulting interrogation primer is blocked, the block must be removed prior to the primer extension operation.

The complementary portion of an interrogation primer can be any length that supports specific and stable hybridization between the interrogation primer and TS-DNA. For this purpose, a length of 10 to 40 nucleotides is preferred, with a complementary portion of an interrogation primer 15 to 30 nucleotides long being most preferred. The preferred use of interrogation primers as primers in primer extension sequencing of an amplified target sequence. For this purpose, interrogation primers should hybridize to TS-DNA 5' of the portion of the amplified target sequences that are to be sequenced. It is preferred that the portion of the amplified target sequences that are to be sequenced represent gap sequences. Such gap sequences preferably collectively represent known, expected, or potential sequence variants present in the portion of the target nucleic acid opposite the gap space formed when an OCP hybridizes to the target nucleic acid. For this purpose, it is preferred that the gap space is filled by DNA polymerase in a gap-filling ligation operation.

L. Caged Oligonucleotides

Caged oligonucleotides are oligonucleotides having a caged nucleotide at their 3' end. The cage structure is a removable blocking group which prevents the 3' hydroxyl from participating in nucleotide addition and ligation reactions. Caged oligonucleotides are useful as primers and probes as described above for use in the amplification, detection, and sequencing operations disclosed herein. Many cage structures are known. A preferred form of cage structure are photolabile structures which allow their removal by exposure to light. Examples of cage structures useful for reversibly blocking the 3' end of oligonucleotides are described by Metzker et al., *Nucleic Acids Research* 22:4259–4267 (1994), Burgess and Jacutin, *Am. Chem Soc.* Abstracts volume 221, abstract 281 (1996), Zehavi et al., *J. Organic Chem.* 37:2281–2288 (1972), Kaplan et al., *Biochem.* 17:1929–1935 (1978), and McCray et al., *Proc. Natl. Acad. Sci. USA* 77:7237–7241 (1980). Preferred forms of caged nucleotides for use in caged oligonucleotides are described by Metzker et al. A most preferred cage structures is a 3'-O-(2-nitrobenzyl) group, which is labile upon exposure to ultraviolet light (Pillai, *Synthesis* 1–26 (1980)). Removal of this cage structure is preferably accomplished by illuminating the material containing the caged nucleotide with long wavelength ultraviolet light (preferably 354 nm) using a transilluminator for 3 to 10 minutes.

Disclosed and known cage structures can be incorporated into oligonucleotides by adapting known and established oligonucleotide synthesis methodology (described below) to use protected caged nucleotides or by adding the cage structure following oligonucleotide synthesis.

As described above, caged oligonucleotides can be used as interrogation probes or degenerate probes. Caged oligonucleotides can also be used as replication primers, such as rolling circle replication primers, either for the entire population of, or a portion of, the primers in an amplification reaction. This allows the pool of functional (that is, extendable) primers to be increased at a specified point in the reaction or amplification operation. For example, when using different rolling circle replication primers to produce different lengths of TS-DNA (see Section II B below), one of the rolling circle replication primers can be a caged oligonucleotide.

M. Peptide Nucleic Acid Clamps

Peptide nucleic acids (PNA) are a modified form of nucleic acid having a peptide backbone. Peptide nucleic acids form extremely stable hybrids with DNA (Hanvey et al., *Science* 258:1481–1485 (1992); Nielsen et al., *Anticancer Drug Des.* 8:53–63 (1993)), and have been used as specific blockers of PCR reactions (Orum et al., *Nucleic Acids Res.*, 21:5332–5336 (1993)). PNA clamps are peptide nucleic acids complementary to sequences in both the left target probe portion and right target probe portion of an OCP, but not to the sequence of any gap oligonucleotides or filled gap space in the ligated OCP. Thus, a PNA clamp can hybridize only to the ligated junction of OCPs that have been illegitimately ligated, that is, ligated in a non-target-directed manner. The PNA clamp can be any length that supports specific and stable hybridization between the clamp and its complement. Generally this is 7 to 12 nucleotides long, but is preferably 8 to 10 nucleotides long. PNA clamps can be used to reduce background signals in rolling circle amplifications by preventing replication of illegitimately ligated OCPs.

N. Oligonucleotide Synthesis

Open circle probes, gap oligonucleotides, rolling circle replication primers, detection probes, address probes, amplification target circles, DNA strand displacement primers, and any other oligonucleotides can be synthesized using established oligonucleotide synthesis methods. Methods to produce or synthesize oligonucleotides are well known in the art. Such methods can range from standard enzymatic digestion followed by nucleotide fragment isolation (see for example, Sambrook et al., *Molecular Cloning: A Laboratory Manual,* 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323–356 (1984), (phosphotriester and phosphite-triester methods), and Narang et al., *Methods Enzymol.,* 65:610–620 (1980), (phosphotriester method). Protein nucleic acid molecules can be made using known methods such as those described by Nielsen et al., *Bioconjug. Chem.* 5:3–7 (1994).

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807–10815 (1995), McGraw et al., *Biotechniques* 8:674–678 (1990), and Rychlik et al., *Nucleic Acids Res.* 18:6409–6412 (1990).

O. Solid-State Detectors

Solid-state detectors are solid-state substrates or supports to which address probes or detection molecules have been coupled. A preferred form of solid-state detector is an array detector. An array detector is a solid-state detector to which multiple different address probes or detection molecules have been coupled in an array, grid, or other organized pattern.

Solid-state substrates for use in solid-state detectors can include any solid material to which oligonucleotides can be coupled. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles. A preferred form for a solid-state substrate is a microtiter dish. The most preferred form of microtiter dish is the standard 96-well type.

Address probes immobilized on a solid-state substrate allow capture of the products of RCA and RCT on a solid-state detector. Such capture provides a convenient means of washing away reaction components that might interfere with subsequent detection steps. By attaching different address probes to different regions of a solid-state detector, different RCA or RCT products can be captured at different, and therefore diagnostic, locations on the solid-state detector. For example, in a microtiter plate multiplex assay, address probes specific for up to 96 different TS-DNAs (each amplified via a different target sequence) can be immobilized on a microtiter plate, each in a different well. Capture and detection will occur only in those wells corresponding to TS-DNAs for which the corresponding target sequences were present in a sample.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022–5026 (1994), and Khrapko et al., *Mol Biol (Mosk) (USSR)* 25:718–730 (1991). A method for immobilization of 3'-amine oligonucleotides on casein-coated slides is described by Stimpson et al., *Proc. Natl. Acad. Sci. USA* 92:6379–6383 (1995). A preferred method of attaching oligonucleotides to solid-state substrates is described by Guo et al., *Nucleic Acids Res.* 22:5456–5465 (1994).

Some solid-state detectors useful in RCA and RCT assays have detection antibodies attached to a solid-state substrate. Such antibodies can be specific for a molecule of interest. Captured molecules of interest can then be detected by binding of a second, reporter antibody, followed by RCA or RCT. Such a use of antibodies in a solid-state detector allows RCA assays to be developed for the detection of any molecule for which antibodies can be generated. Methods for immobilizing antibodies to solid-state substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is glutaraldehyde. These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209–216 and 241–242, and *Immobilized Affinity Ligands*, Craig T. Hermanson et al., eds. (Academic Press, New York, 1992). Antibodies can be attached to a substrate by chemically cross-linking a free amino group on the antibody to reactive side groups present within the solid-state substrate. For example, antibodies may be chemically cross-linked to a substrate that contains free amino or carboxyl groups using glutaraldehyde or carbodiimides as cross-linker agents. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

P. Solid-State Samples

Solid-state samples are solid-state substrates or supports to which target molecules or target sequences have been coupled or adhered. Target molecules or target sequences are preferably delivered in a target sample or assay sample. A preferred form of solid-state sample is an array sample. An array sample is a solid-state sample to which multiple different target samples or assay samples have been coupled or adhered in an array, grid, or other organized pattern.

Solid-state substrates for use in solid-state samples can include any solid material to which target molecules or target sequences can be coupled or adhered. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, slides, fibers, woven fibers, shaped polymers, particles and microparticles. Preferred forms for a solid-state substrate are microtiter dishes and glass slides. The most preferred form of microtiter dish is the standard 96-well type.

Target molecules and target sequences immobilized on a solid-state substrate allow formation of target-specific TS-DNA localized on the solid-state substrate. Such localization provides a convenient means of washing away reaction components that might interfere with subsequent detection steps, and a convenient way of assaying multiple different samples simultaneously. Diagnostic TS-DNA can be independently formed at each site where a different sample is adhered. For immobilization of target sequences or other oligonucleotide molecules to form a solid-state sample, the methods described above for can be used. Where the target molecule is a protein, the protein can be immobilized on a solid-state substrate generally as described above for the immobilization of antibodies.

A preferred form of solid-state substrate is a glass slide to which up to 256 separate target or assay samples have been adhered as an array of small dots. Each dot is preferably from 0.1 to 2.5 mm in diameter, and most preferably around 2.5 mm in diameter. Such microarrays can be fabricated, for example, using the method described by Schena et al., *Science* 270:487–470 (1995). Briefly, microarrays can be fabricated on poly-L-lysine-coated microscope slides (Sigma) with an arraying machine fitted with one printing tip. The tip is loaded with 1 μl of a DNA sample (0.5 mg/ml) from, for example, 96-well microtiter plates and deposited ~0.005 μl per slide on multiple slides at the desired spacing. The printed slides can then be rehydrated for 2 hours in a humid chamber, snap-dried at 100° C. for 1 minute, rinsed in 0.1% SDS, and treated with 0.05% succinic anhydride prepared in buffer consisting of 50% 1-methyl-2-pyrrolidinone and 50% boric acid. The DNA on the slides can then be denatured in, for example, distilled water for 2 minutes at 90° C. immediately before use. Microarray solid-state samples can scanned with, for example, a laser fluorescent scanner with a computer-controlled XY stage and a microscope objective. A mixed gas, multiline laser allows sequential excitation of multiple fluorophores.

Q. Reporter Binding Agents

Figure 29A:
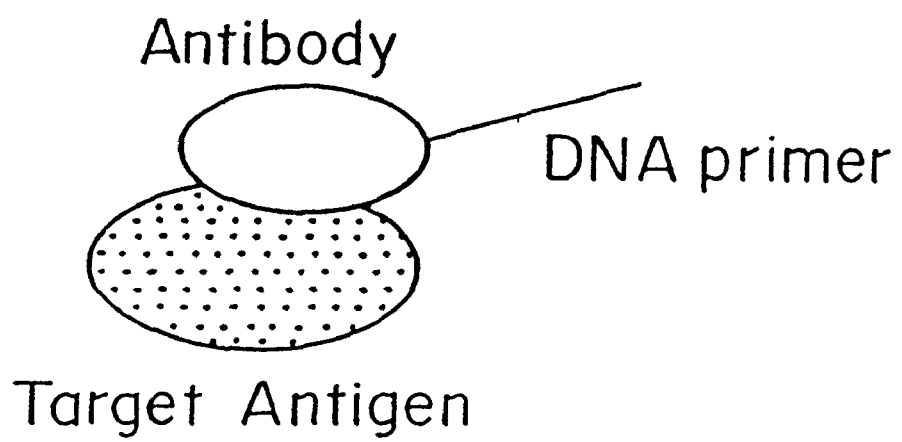
FIGS. 29A and 29B are diagrams of a reporter binding molecule made up of an antibody (as the affinity portion) and a rolling circle replication primer (as the oligonucleotide portion). The affinity portion is shown bound to a target antigen.

A reporter binding agent is a specific binding molecule coupled or tethered to an oligonucleotide. The specific binding molecule is referred to as the affinity portion of the reporter binding agent and the oligonucleotide is referred to as the oligonucleotide portion of the reporter binding agent. As used herein, a specific binding molecule is a molecule that interacts specifically with a particular molecule or moiety. The molecule or moiety that interacts specifically with a specific binding molecule is referred to herein as a target molecule. It is to be understood that the term target molecule refers to both separate molecules and to portions of molecules, such as an epitope of a protein, that interacts specifically with a specific binding molecule. Antibodies, either member of a receptor/ligand pair, and other molecules with specific binding affinities are examples of specific binding molecules, useful as the affinity portion of a reporter binding molecule. A reporter binding molecule with an affinity portion which is an antibody is referred to herein as a reporter antibody. By tethering an amplification target circle or coupling a target sequence to such specific binding molecules, binding of a specific binding molecule to its specific target can be detected by amplifying the ATC or target sequence with rolling circle amplification. This amplification allows sensitive detection of a very small number of bound specific binding molecules. A reporter binding molecule that interacts specifically with a particular target molecule is said to be specific for that target molecule. For example, a reporter binding molecule with an affinity portion which is an antibody that binds to a particular antigen is said to be specific for that antigen. The antigen is the target molecule. Reporter binding agents are also referred to herein as reporter binding molecules. FIGS. 25, 26, 27, 28, and 29 illustrate examples of several preferred types of reporter binding molecules and their use. FIG. 29 illustrates a reporter binding molecule using an antibody as the affinity portion.

A special form of reporter binding molecule, referred to herein as a reporter binding probe, has an oligonucleotide or oligonucleotide derivative as the specific binding molecule. Reporter binding probes are designed for and used to detect specific nucleic acid sequences. Thus, the target molecule for reporter binding probes are nucleic acid sequences. The target molecule for a reporter binding probe can be a nucleotide sequence within a larger nucleic acid molecule. It is to be understood that the term reporter binding molecule encompasses reporter binding probes. The specific binding molecule of a reporter binding probe can be any length that supports specific and stable hybridization between the reporter binding probe and the target molecule. For this purpose, a length of 10 to 40 nucleotides is preferred, with a specific binding molecule of a reporter binding probe 16 to 25 nucleotides long being most preferred. It is preferred that the specific binding molecule of a reporter binding probe is peptide nucleic acid. As described above, peptide nucleic acid forms a stable hybrid with DNA. This allows a reporter binding probe with a peptide nucleic acid specific binding molecule to remain firmly adhered to the target sequence during subsequent amplification and detection operations. This useful effect can also be obtained with reporter binding probes with oligonucleotide specific binding molecules by making use of the triple helix chemical bonding technology described by Gasparro et al., Nucleic Acids Res. 1994 22(14):2845–2852 (1994). Briefly, the affinity portion of a reporter binding probe is designed to form a triple helix when hybridized to a target sequence. This is accomplished generally as known, preferably by selecting either a primarily homopurine or primarily homopyrimidine target sequence. The matching oligonucleotide sequence which constitutes the affinity portion of the reporter binding probe will be complementary to the selected target sequence and thus be primarily homopyrimidine or primarily homopurine, respectively. The reporter binding probe (corresponding to the triple helix probe described by Gasparro et al.) contains a chemically linked psoralen derivative. Upon hybridization of the reporter binding probe to a target sequence, a triple helix forms. By exposing the triple helix to low wavelength ultraviolet radiation, the psoralen derivative mediates cross-linking of the probe to the target sequence. FIGS. 25, 26, 27, and 28 illustrate examples of reporter binding molecules that are reporter binding probes.

The specific binding molecule in a reporter binding probe can also be a bipartite DNA molecule, such as ligatable DNA probes adapted from those described by Landegren et al., Science 241:1077–1080 (1988). When using such a probe, the affinity portion of the probe is assembled by target-mediated ligation of two oligonucleotide portions which hybridize to adjacent regions of a target nucleic acid. Thus, the components used to form the affinity portion of such reporter binding probes are a truncated reporter binding probe (with a truncated affinity portion which hybridizes to part of the target sequence) and a ligation probe which hybridizes to an adjacent part of the target sequence such that it can be ligated to the truncated reporter binding probe. The ligation probe can also be separated from (that is, not adjacent to) the truncated reporter binding probe when both are hybridized to the target sequence. The resulting space between them can then be filled by a second ligation probe or by gap-filling synthesis. For use in the disclosed methods, it is preferred that the truncated affinity portion be long enough to allow target-mediated ligation but short enough to, in the absence of ligation to the ligation probe, prevent stable hybridization of the truncated reporter binding probe to the target sequence during the subsequent amplification operation. For this purpose, a specific step designed to eliminate hybrids between the target sequence and unligated truncated reporter binding probes can be used following the ligation operation.

In one embodiment, the oligonucleotide portion of a reporter binding agent includes a sequence, referred to as a target sequence, that serves as a target sequence for an OCP. The sequence of the target sequence can be arbitrarily chosen. In a multiplex assay using multiple reporter binding agents, it is preferred that the target sequence for each reporter binding agent be substantially different to limit the possibility of non-specific target detection. Alternatively, it may be desirable in some multiplex assays, to use target sequences with related sequences. By using different, unique gap oligonucleotides to fill different gap spaces, such assays can use one or a few OCPs to amplify and detect a larger number of target sequences. The oligonucleotide portion can be coupled to the affinity portion by any of several established coupling reactions. For example, Hendrickson et al., Nucleic Acids Res., 23(3):522–529 (1995) describes a suitable method for coupling oligonucleotides to antibodies.

In another embodiment, the oligonucleotide portion of a reporter binding agent includes a sequence, referred to as a rolling circle replication primer sequence, that serves as a rolling circle replication primer for an ATC. This allows rolling circle replication of an added ATC where the resulting TS-DNA is coupled to the reporter binding agent. Because of this, the TS-DNA will be effectively immobilized at the site of the target molecule. Preferably, the immobilized TS-DNA can then be collapsed in situ prior to detection. The sequence of the rolling circle replication primer sequence can be arbitrarily chosen. In a multiplex assay using multiple reporter binding agents, it is preferred that the rolling circle replication primer sequence for each reporter binding agent be substantially different to limit the possibility of non-specific target detection. Alternatively, it may be desirable in some multiplex assays, to use rolling circle replication primer sequences with related sequences. Such assays can use one or a few ATCs to detect a larger number of target molecules. When the oligonucleotide portion of a reporter binding agent is used as a rolling circle replication primer, the oligonucleotide portion can be any length that supports specific and stable hybridization between the oligonucleotide portion and the primer complement portion of an amplification target circle. Generally this is 10 to 35 nucleotides long, but is preferably 16 to 20 nucleotides long. FIGS. 25, 26, 27, 28, and 29 illustrate examples of reporter binding molecules in which the oligonucleotide portion is a rolling circle replication primer.

In another embodiment, the oligonucleotide portion of a reporter binding agent can include an amplification target circle which serves as a template for rolling circle replication. In a multiplex assay using multiple reporter binding agents, it is preferred that address tag portions and detection tag portions of the ATC comprising the oligonucleotide portion of each reporter binding agent be substantially different to unique detection of each reporter binding agent. It is desirable, however, to use the same primer complement portion in all of the ATCs used in a multiplex assay. The ATC is tethered to the specific binding molecule by looping the ATC around a tether loop. This allows the ATC to rotate freely during rolling circle replication while remaining coupled to the affinity portion. The tether loop can be any material that can form a loop and be coupled to a specific binding molecule. Linear polymers are a preferred material for tether loops.

A preferred method of producing a reporter binding agent with a tethered ATC is to form the tether loop by ligating the ends of oligonucleotides coupled to a specific binding molecule around an ATC. Oligonucleotides can be coupled to specific binding molecules using known techniques. For example, Hendrickson et al. (1995), describes a suitable method for coupling oligonucleotides to antibodies. This method is generally useful for coupling oligonucleotides to any protein. To allow ligation, oligonucleotides comprising the two halves of the tether loop should be coupled to the specific binding molecule in opposite orientations such that the free end of one is the 5' end and the free end of the other is the 3' end. Ligation of the ends of the tether oligonucleotides can be mediated by hybridization of the ends of the tether oligonucleotides to adjacent sequences in the ATC to be tethered. In this way, the ends of the tether oligonucleotides are analogous to the target probe portions of an open circle probe, with the ATC containing the target sequence.

Another preferred method of producing a reporter binding agent with a tethered ATC is to ligate an open circle probe while hybridized to an oligonucleotide tether loop on a specific binding molecule. This is analogous to the ligation operation of LM-RCA. In this case, the target sequence is part of an oligonucleotide with both ends coupled to a specific binding molecule. In this method, both ends of a single tether oligonucleotide are coupled to a specific binding molecule. This can be accomplished using known coupling techniques as described above.

The ends of tether loops can be coupled to any specific binding molecule with functional groups that can be derivatized with suitable activating groups. When the specific binding molecule is a protein, or a molecule with similar functional groups, coupling of tether ends can be accomplished using known methods of protein attachment. Many such methods are described in *Protein immobilization: fundamentals and applications* Richard F. Taylor, ed. (M. Dekker, New York, 1991).

Antibodies useful as the affinity portion of reporter binding agents, can be obtained commercially or produced using well established methods. For example, Johnstone and Thorpe, on pages 30–85, describe general methods useful for producing both polyclonal and monoclonal antibodies. The entire book describes many general techniques and principles for the use of antibodies in assay systems.

R. DNA Ligases

Any DNA ligase is suitable for use in the disclosed amplification method. Preferred ligases are those that preferentially form phosphodiester bonds at nicks in double-stranded DNA. That is, ligases that fail to ligate the free ends of single-stranded DNA at a significant rate are preferred. Thermostable ligases are especially preferred. Many suitable ligases are known, such as T4 DNA ligase (Davis et al., *Advanced Bacterial Genetics—A Manual for Genetic Engineering* (Cold Spring Harbor Laboratory, Cold Spring Harbor, N.Y., 1980)), *E. coli* DNA ligase (Panasnko et al., *J. Biol. Chem.* 253:4590–4592 (1978)), AMPLIGASE® (Kalin et al., *Mutat. Res.*, 283(2):119–123 (1992); Winn-Deen et al., *Mol Cell Probes* (England) 7(3):179–186 (1993)), Taq DNA ligase (Barany, *Proc. Natl. Acad. Sci. USA* 88:189–193 (1991), *Thermus thermophilus* DNA ligase (Abbott Laboratories), *Thermus scotoductus* DNA ligase and *Rhodothermus marinus* DNA ligase (Thorbjarnardottir et al., *Gene* 151:177–180 (1995)). T4 DNA ligase is preferred for ligations involving RNA target sequences due to its ability to ligate DNA ends involved in DNA:RNA hybrids (Hsuih et al., *Quantitative detection of HCV RNA using novel ligation-dependent polymerase chain reaction*, American Association for the Study of Liver Diseases (Chicago, Ill., Nov. 3–7, 1995)).

The frequency of non-target-directed ligation catalyzed by a ligase can be determined as follows. LM-RCA is performed with an open circle probe and a gap oligonucleotide in the presence of a target sequence. Non-targeted-directed ligation products can then be detected by using an address probe specific for the open circle probe ligated without the gap oligonucleotide to capture TS-DNA from such ligated probes. Target directed ligation products can be detected by using an address probe specific for the open circle probe ligated with the gap oligonucleotide. By using a solid-state detector with regions containing each of these address probes, both target directed and non-target-directed ligation products can be detected and quantitated. The ratio of target-directed and non-target-directed TS-DNA produced provides a measure of the specificity of the ligation operation. Target-directed ligation can also be assessed as discussed in Barany (1991).

S. DNA Polymerases

DNA polymerases useful in the rolling circle replication step of RCA must perform rolling circle replication of primed single-stranded circles. Such polymerases are referred to herein as rolling circle DNA polymerases. For rolling circle replication, it is preferred that a DNA polymerase be capable of displacing the strand complementary to the template strand, termed strand displacement, and lack a 5' to 3' exonuclease activity. Strand displacement is necessary to result in synthesis of multiple tandem copies of the ligated OCP. A 5' to 3' exonuclease activity, if present, might result in the destruction of the synthesized strand. It is also preferred that DNA polymerases for use in the disclosed method are highly processive. The suitability of a DNA polymerase for use in the disclosed method can be readily determined by assessing its ability to carry out rolling circle replication. Preferred rolling circle DNA polymerases are bacteriophage Φ29 DNA polymerase (U.S. Pat. Nos. 5,198,543 and 5,001,050 to Blanco et al.), phage M2 DNA polymerase (Matsumoto et al., *Gene* 84:247 (1989)), phage ΦPRD1 DNA polymerase (Jung et al., *Proc. Natl. Acad. Sci. USA* 84:8287 (1987)), VENT® DNA polymerase (Kong et al., *J. Biol. Chem.* 268:1965–1975 (1993)), Klenow fragment of DNA polymerase I (Jacobsen et al., *Eur. J. Biochem.* 45:623–627 (1974)), T5 DNA polymerase (Chatterjee et al., *Gene* 97:13–19 (1991)), PRD1 DNA polymerase (Zhu and Ito, *Biochim. Biophys. Acta.* 1219:267–276 (1994)), modified T7 DNA polymerase (Tabor and Richardson, *J. Biol. Chem.* 262:15330–15333 (1987); Tabor and Richardson, *J. Biol. Chem.* 264:6447–6458 (1989); Sequenase™ (U.S. Biochemicals)), and T4 DNA polymerase holoenzyme (Kaboord and Benkovic, *Curr. Biol.* 5:149–157 (1995)). Φ29 DNA polymerase is most preferred.

Strand displacement can be facilitated through the use of a strand displacement factor, such as helicase. It is considered that any DNA polymerase that can perform rolling circle replication in the presence of a strand displacement factor is suitable for use in the disclosed method, even if the DNA polymerase does not perform rolling circle replication in the absence of such a factor. Strand displacement factors useful in RCA include BMRF1 polymerase accessory subunit (Tsurumi et al., *J. Virology* 67(12):7648–7653 (1993)), adenovirus DNA-binding protein (Zijderveld and van der Vliet, *J. Virology* 68(2):1158–1164 (1994)), herpes simplex viral protein ICP8 (Boehmer and Lehman, *J. Virology* 67(2):711–715 (1993); Skaliter and Lehman, *Proc. Natl. Acad. Sci. USA* 91(22):10665–10669 (1994)), single-stranded DNA binding proteins (SSB; Rigler and Romano, *J. Biol. Chem.* 270:8910–8919 (1995)), and calf thymus helicase (Siegel et al., *J. Biol. Chem.* 267:13629–13635 (1992)).

The ability of a polymerase to carry out rolling circle replication can be determined by using the polymerase in a rolling circle replication assay such as those described in Fire and Xu, *Proc. Natl. Acad. Sci. USA* 92:4641–4645 (1995) and in Example 1.

Another type of DNA polymerase can be used if a gap-filling synthesis step is used, such as in gap-filling LM-RCA (see Example 3). When using a DNA polymerase to fill gaps, strand displacement by the DNA polymerase is undesirable. Such DNA polymerases are referred to herein as gap-filling DNA polymerases. Unless otherwise indicated, a DNA polymerase referred to herein without specifying it as a rolling circle DNA polymerase or a gap-filling DNA polymerase, is understood to be a rolling circle DNA polymerase and not a gap-filling DNA polymerase. Preferred gap-filling DNA polymerases are T7 DNA polymerase (Studier et al., *Methods Enzymol.* 185:60–89 (1990)), DEEP VENT® DNA polymerase (New England Biolabs, Beverly, Mass.), modified T7 DNA polymerase (Tabor and Richardson, *J. Biol. Chem.* 262:15330–15333 (1987); Tabor and Richardson, *J. Biol. Chem.* 264:6447–6458 (1989); Sequenase™ (U.S. Biochemicals)), and T4 DNA polymerase (Kunkel et al., *Methods Enzymol.* 154:367–382 (1987)). An especially preferred type of gap-filling DNA polymerase is the *Thermus flavus* DNA polymerase (MBR, Milwaukee, Wis.). The most preferred gap-filling DNA polymerase is the Stoffel fragment of Taq DNA polymerase (Lawyer et al., *PCR Methods Appl.* 2(4):275–287 (1993), King et al., *J. Biol. Chem.* 269(18):13061–13064 (1994)).

The ability of a polymerase to fill gaps can be determined by performing gap-filling LM-RCA. Gap-filling LM-RCA is performed with an open circle probe that forms a gap space when hybridized to the target sequence. Ligation can only occur when the gap space is filled by the DNA polymerase. If gap-filling occurs, TS-DNA can be detected, otherwise it can be concluded that the DNA polymerase, or the reaction conditions, is not useful as a gap-filling DNA polymerase.

T. RNA polymerases

Any RNA polymerase which can carry out transcription in vitro and for which promoter sequences have been identified can be used in the disclosed rolling circle transcription method. Stable RNA polymerases without complex requirements are preferred. Most preferred are T7 RNA polymerase (Davanloo et al., *Proc. Natl. Acad. Sci. USA* 81:2035–2039 (1984)) and SP6 RNA polymerase (Butler and Chamberlin, *J. Biol. Chem.* 257:5772–5778 (1982)) which are highly specific for particular promoter sequences (Schenborn and Meirendorf, *Nucleic Acids Research* 13:6223–6236 (1985)). Other RNA polymerases with this characteristic are also preferred. Because promoter sequences are generally recognized by specific RNA polymerases, the OCP or ATC should contain a promoter sequence recognized by the RNA polymerase that is used. Numerous promoter sequences are known and any suitable RNA polymerase having an identified promoter sequence can be used. Promoter sequences for RNA polymerases can be identified using established techniques.

The materials described above can be packaged together in any suitable combination as a kit useful for performing the disclosed method.

II. Method

The disclosed rolling circle amplification (RCA) method involves replication of circular single-stranded DNA molecules. In RCA, a rolling circle replication primer hybridizes to circular OCP or ATC molecules followed by rolling circle replication of the OCP or ATC molecules using a strand-displacing DNA polymerase. Amplification takes place during rolling circle replication in a single reaction cycle. Rolling circle replication results in large DNA molecules containing tandem repeats of the OCP or ATC sequence. This DNA molecule is referred to as a tandem sequence DNA (TS-DNA). Rolling circle amplification is also referred to herein as unimolecular segment amplification (USA). The term unimolecular segment amplification is generally used herein to emphasis the amplification of individual segments of nucleic acid, such as a target sequence, that are of interest.

A preferred embodiment, ligation-mediated rolling circle amplification (LM-RCA) method involves a ligation operation prior to replication. In the ligation operation, an OCP hybridizes to its cognate target nucleic acid sequence, if present, followed by ligation of the ends of the hybridized OCP to form a covalently closed, single-stranded OCP. After ligation, a rolling circle replication primer hybridizes to OCP molecules followed by rolling circle replication of the circular OCP molecules using a strand-displacing DNA polymerase. Generally, LM-RCA comprises (a) mixing an open circle probe (OCP) with a target sample, resulting in an OCP-target sample mixture, and incubating the OCP-target sample mixture under conditions promoting hybridization between the open circle probe and a target sequence, (b) mixing ligase with the OCP-target sample mixture, resulting in a ligation mixture, and incubating the ligation mixture under conditions promoting ligation of the open circle probe to form an amplification target circle (ATC), (c) mixing a rolling circle replication primer (RCRP) with the ligation mixture, resulting in a primer-ATC mixture, and incubating the primer-ATC mixture under conditions that promote hybridization between the amplification target circle and the rolling circle replication primer, (d) mixing DNA polymerase with the primer-ATC mixture, resulting in a polymerase-ATC mixture, and incubating the polymerase-ATC mixture under conditions promoting replication of the amplification target circle, where replication of the amplification target circle results in formation of tandem sequence DNA (TS-DNA).

The open circle probe is a single-stranded, linear DNA molecule comprising, from 5' end to 3' end, a 5' phosphate group, a right target probe portion, a primer complement portion, a spacer region, a left target probe portion, and a 3' hydroxyl group, wherein the left target probe portion is complementary to the 5' region of a target sequence and the right target probe portion is complementary to the 3' region of the target sequence.

The left and right target probe portions hybridize to the two ends of the target nucleic acid sequence, with or without a central gap to be filled by one or more gap oligonucleotides. Generally, LM-RCA using gap oligonucleotides can be performed by, in an LM-RCA reaction, (1) using a target sequence with a central region located between a 5' region and a 3' region, and an OCP where neither the left target probe portion of the open circle probe nor the right target probe portion of the open circle probe is complementary to the central region of the target sequence, and (2) mixing one or more gap oligonucleotides with the target sample, such that the OCP-target sample mixture contains the open circle probe, the one or more gap oligonucleotides, and the target sample, where each gap oligonucleotide consists of a single-stranded, linear DNA molecule comprising a 5' phosphate group and a 3' hydroxyl group, where each gap oligonucleotide is complementary all or a portion of the central region of the target sequence.

A. The Ligation Operation

An open circle probe, optionally in the presence of one or more gap oligonucleotides, is incubated with a sample containing DNA, RNA, or both, under suitable hybridization conditions, and then ligated to form a covalently closed circle. The ligated open circle probe is a form of amplification target circle. This operation is similar to ligation of padlock probes described by Nilsson et al., *Science*, 265:2085–2088 (1994). The ligation operation allows subsequent amplification to be dependent on the presence of a target sequence. Suitable ligases for the ligation operation are described above. Ligation conditions are generally known. Most ligases require $Mg^{++}$. There are two main types of ligases, those that are ATP-dependent and those that are NAD-dependent. ATP or NAD, depending on the type of ligase, should be present during ligation.

The ligase and ligation conditions can be optimized to limit the frequency of ligation of single-stranded termini. Such ligation events do not depend on the presence of a target sequence. In the case of AMPLIGASE®-catalyzed ligation, which takes place at 60° C., it is estimated that no more than 1 in 1,000,000 molecules with single-stranded DNA termini will be ligated. This is based on the level of non-specific amplification seen with this ligase in the ligase chain reaction. Any higher nonspecific ligation frequency would cause enormously high background amplification in the ligase chain reaction. Using this estimate, an approximate frequency for the generation of non-specifically ligated open circles with a correctly placed gap oligonucleotide in at the ligation junction can be calculated. Since two ligation events are involved, the frequency of such events using AMPLIGASE® should be the square of 1 in 1,000,000, or 1 in $1\times10^{12}$. The number of probes used in a typical ligation reaction of 50 $\mu$l is $2\times10^{12}$. Thus, the number of non-specifically ligated circles containing a correct gap oligonucleotide would be expected to be about 2 per reaction.

When RNA is to be detected, it is preferred that a reverse transcription operation be performed to make a DNA target sequence. An example of the use of such an operation is described in Example 4. Alternatively, an RNA target sequence can be detected directly by using a ligase that can perform ligation on a DNA:RNA hybrid substrate. A preferred ligase for this is T4 DNA ligase.

B. The Replication Operation

Figure 4:
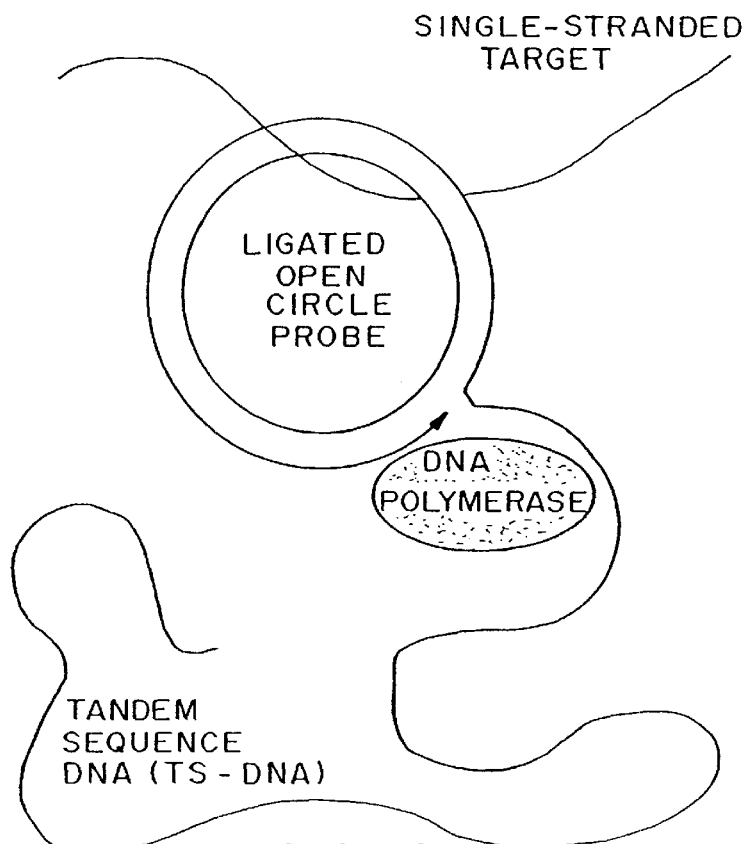
FIG. 4 is a diagram of rolling circle amplification of an open circle probe topologically locked to the nucleic acid containing the target sequence.

The circular open circle probes formed by specific ligation and amplification target circles serve as substrates for a rolling circle replication. This reaction requires the addition of two reagents: (a) a rolling circle replication primer, which is complementary to the primer complement portion of the OCP or ATC, and (b) a rolling circle DNA polymerase. The DNA polymerase catalyzes primer extension and strand displacement in a processive rolling circle polymerization reaction that proceeds as long as desired, generating a molecule of up to 100,000 nucleotides or larger that contains up to approximately 1000 tandem copies of a sequence complementary to the amplification target circle or open circle probe (FIG. 4). This tandem sequence DNA (TS-DNA) consists of, in the case of OCPs, alternating target sequence and spacer sequence. Note that the spacer sequence of the TS-DNA is the complement of the sequence between the left target probe and the right target probe in the original open circle probe. A preferred rolling circle DNA polymerase is the DNA polymerase of the bacteriophage Φ29.

During rolling circle replication one may additionally include radioactive, or modified nucleotides such as bromodeoxyuridine triphosphate, in order to label the DNA generated in the reaction. Alternatively, one may include suitable precursors that provide a binding moiety such as biotinylated nucleotides (Langer et al. (1981)).

Rolling circle amplification can be engineered to produce TS-DNA of different lengths in an assay involving multiple ligated OCPs or ATCs. This can be useful for extending the number of different targets that can be detected in a single assay. TS-DNA of different lengths can be produced in several ways. In one embodiment, the base composition of the spacer region of different classes of OCP or ATC can be designed to be rich in a particular nucleotide. Then a small amount of the dideoxy nucleotide complementary to the enriched nucleotide can be included in the rolling circle amplification reaction. After some amplification, the dideoxy nucleotides will terminate extension of the TS-DNA product of the class of OCP or ATC enriched for the complementary nucleotide. Other OCPs or ATCs will be less likely to be terminated, since they are not enriched for the complementary nucleotide, and will produce longer TS-DNA products, on average.

In another embodiment, two different classes of OCP or ATC can be designed with different primer complement portions. These different primer complement portions are designed to be complementary to a different rolling circle replication primer. Then the two different rolling circle replication primers are used together in a single rolling circle amplification reaction, but at significantly different concentrations. The primer at high concentration immediately primes rolling circle replication due to favorable kinetics, while the primer at lower concentration is delayed in priming due to unfavorable kinetics. Thus, the TS-DNA product of the class of OCP or ATC designed for the primer at high concentration will be longer than the TS-DNA product of the class of OCP or ATC designed for the primer at lower concentration since it will have been replicated for a longer period of time. As another option, one of the rolling circle replication primers can be a caged oligonucleotide. In this case, the two rolling circle replication primers can be at similar concentrations. The caged rolling circle replication primer will not support rolling circle replication until the cage structure is removed. Thus, the first, uncaged rolling circle replication primer begins amplification of its cognate amplification target circle(s) when the replication operation begins, the second, caged rolling circle replication primer begins amplification of its cognate amplification target circle (s) only after removal of the cage. The amount of TS-DNA produced from each rolling circle replication primer will differ proportionate to the different effective times of replication. Thus, the amount of TS-DNA made using each type of rolling circle replication primer can be controlled using a caged primer. The use of such a caged primer has the advantage that the caged primer can be provided at a sufficient concentration to efficiently initiate rolling circle replication as soon as it is uncaged (rather than at a lower concentration).

C. Modifications and Additional Operations

1. Detection of Amplification Products

Current detection technology makes a second cycle of RCA unnecessary in many cases. Thus, one may proceed to detect the products of the first cycle of RCA directly. Detection may be accomplished by primary labeling or by secondary labeling, as described below.

(a) Primary Labeling

Primary labeling consists of incorporating labeled moieties, such as fluorescent nucleotides, biotinylated nucleotides, digoxygenin-containing nucleotides, or bromodeoxyuridine, during rolling circle replication in RCA, or during transcription in RCT. For example, one may incorporate cyanine dye UTP analogs (Yu et al. (1994)) at a frequency of 4 analogs for every 100 nucleotides. A preferred method for detecting nucleic acid amplified in situ is to label the DNA during amplification with BrdUrd, followed by binding of the incorporated BUDR with a biotinylated anti-BUDR antibody (Zymed Labs, San Francisco, Calif.), followed by binding of the biotin moieties with Streptavidin-Peroxidase (Life Sciences, Inc.), and finally development of fluorescence with Fluorescein-tyramide (DuPont de Nemours & Co., Medical Products Dept.).

(b) Secondary Labeling With Detection Probes

Secondary labeling consists of using suitable molecular probes, referred to as detection probes, to detect the amplified DNA or RNA. For example, an open circle may be designed to contain several repeats of a known arbitrary sequence, referred to as detection tags. A secondary hybridization step can be used to bind detection probes to these detection tags (FIG. 7). The detection probes may be labeled as described above with, for example, an enzyme, fluorescent moieties, or radioactive isotopes. By using three detection tags per open circle probe, and four fluorescent moieties per each detection probe, one may obtain a total of twelve fluorescent signals for every open circle probe repeat in the TS-DNA, yielding a total of 12,000 fluorescent moieties for every ligated open circle probe that is amplified by RCA.

(c) Multiplexing and Hybridization Array Detection

RCA is easily multiplexed by using sets of different open circle probes, each set carrying different target probe sequences designed for binding to unique targets. Note that although the target probe sequences designed for each target are different, the primer complement portion may remain unchanged, and thus the primer for rolling circle replication can remain the same for all targets. Only those open circle probes that are able to find their targets will give rise to TS-DNA. The TS-DNA molecules generated by RCA are of high molecular weight and low complexity; the complexity being the length of the open circle probe. There are two alternatives for capturing a given TS-DNA to a fixed position in a solid-state detector. One is to include within the spacer region of the open circle probes a unique address tag sequence for each unique open circle probe. TS-DNA generated from a given open circle probe will then contain sequences corresponding to a specific address tag sequence. A second and preferred alternative is to use the target sequence present on the TS-DNA as the address tag.

(d) Combinatorial Multicolor Coding

A preferred form of multiplex detection involves the use of a combination of labels that either fluoresce at different wavelengths or are colored differently. One of the advantages of fluorescence for the detection of hybridization probes is that several targets can be visualized simultaneously in the same sample. Using a combinatorial strategy, many more targets can be discriminated than the number of spectrally resolvable fluorophores. Combinatorial labeling provides the simplest way to label probes in a multiplex fashion since a probe fluor is either completely absent (−) or present in unit amounts (+); image analysis is thus more amenable to automaton, and a number of experimental artifacts, such as differential photobleaching of the fluors and the effects of changing excitation source power spectrum, are avoided.

The combinations of labels establish a code for identifying different detection probes and, by extension, different target molecules to which those detection probes are associated with. This labeling scheme is referred to as Combinatorial Multicolor Coding (CMC). Such coding is described by Speicher et al., *Nature Genetics* 12:368–375 (1996). Any number of labels, which when combined can be separately detected, can be used for combinatorial multicolor coding. It is preferred that 2, 3, 4, 5, or 6 labels be used in combination. It is most preferred that 6 labels be used. The number of labels used establishes the number of unique label combinations that can be formed according to the formula $2^N-1$, where N is the number of labels. According to this formula, 2 labels forms three label combinations, 3 labels forms seven label combinations, 4 labels forms 15 label combinations, labels form 31 label combinations, and 6 labels forms 63 label combinations.

For combinatorial multicolor coding, a group of different detection probes are used as a set. Each type of detection probe in the set is labeled with a specific and unique combination of fluorescent labels. For those detection probes assigned multiple labels, the labeling can be accomplished by labeling each detection probe molecule with all of the required labels. Alternatively, pools of detection probes of a given type can each be labeled with one of the required labels. By combining the pools, the detection probes will, as a group, contain the combination of labels required for that type of detection probe. This can be illustrated with a simple example. Starting with seven different types of detection probe, each complementary to a different detection tag and designated 1 through 7, unique identification requires three different labels used in seven combinations. Assigning the combinations arbitrarily, one coding scheme is:

| Detection probe | 1 | 2 | 3 | 4 | 5 | 6 | 7 |
|---|---|---|---|---|---|---|---|
| label A | + | | | + | + | | + |
| label B | | + | | + | | + | + |
| label C | | | + | | + | + | + |

As can be seen, detection probe 7 must be labeled with three different labels, A, B, and C. This can be accomplished by labels A, B, and C to each individual detection probe 7 molecule. This is the first option described above. Alternatively, three pools of detection probe 7 can be separately labeled, one pool with label A, one pool with label B, and one pool with label C. In each pool, individual detection molecules are labeled with a single type of label. Mixing the pools results in a solution of detection probe 7 that collectively contains all three labels as required. Labeling of detection probes requiring different numbers of probes can be accomplished in a similar fashion.

Of course, the two types of labeling schemes described above can be combined, resulting in detection probe molecules with multiple labels combined with detection probe molecules of the same type multiply labeled with different labels. This can be illustrated using the example above. Two pools of detection probe type 7 can be separately labeled, one pool with both labels A and B, and one pool with only label C. Mixing the pools results in a solution of detection probe 7 that collectively contains all three labels as required. Combinatorial multicolor coding is further illustrated in Examples 7 and 8.

Where each detection probe is labeled with a single label, label combinations can also be generated by using OCPs or ATCs with coded combinations of detection tags complementary to the different detection probes. In this scheme, the OCPs or ATCs will contain a combination of detection tags representing the combination of labels required for a specific label code. Using the example above, a set of seven OCPs or ATCs, designated 1 though 7, would contain one, two, or three detection tags, chosen from a set of three detection tag sequences designated dtA, dtB, and dtC. Each detection tag sequence corresponds to one of the labels, A, B, or C, with each label coupled to one of three detection probes, designated dpA, dpB, or dpC, respectively. An example of the resulting coding scheme would be:

| OCP or ATC | 1 | 2 | 3 | 4 | 5 | 6 | 7 |
|---|---|---|---|---|---|---|---|
| dtA | + | | | + | + | | + |
| dtB | | + | | + | | + | + |
| dtC | | | + | | + | + | + |

Hybridization could be performed with a pool of all the different labeled detection probes, dpA, dpB, and dpC. The result would be that TS-DNA generated from OCP 7 would hybridize to all three detection probes, thus labeling the TS-DNA with all three labels. In contrast, TS-DNA generated from OCP 4, for example, would hybridize only to detection probes dpA and dpB, thus labeling the OCP 4-derived TS-DNA with only labels A and B. This method of coding and detection is preferred. Use of this coding scheme is illustrated in Examples 7 and 8.

As described above, rolling circle amplification can be engineered to produce TS-DNA of different lengths in an assay involving multiple ligated OCPs or ATCs. The resulting TS-DNA of different length can be distinguished simply on the basis of the size of the detection signal they generate. Thus, the same set of detection probes could be used to distinguish two different sets of generated TS-DNA. In this scheme, two different TS-DNAs, each of a different size but assigned the same color code, would be distinguished by the size of the signal produced by the hybridized detection probes. In this way, a total of 126 different targets can be distinguished on a single solid-state sample using a code with 63 combinations, since the signals will come in two flavors, low amplitude and high amplitude. Thus one could, for example, use the low amplitude signal set of 63 probes for detection of an oncogene mutations, and the high amplitude signal set of 63 probes for the detection of a tumor suppressor p53 mutations.

Speicher et al. describes a set of fluors and corresponding optical filters spaced across the spectral interval 350–770 nm that give a high degree of discrimination between all possible fluor pairs. This fluor set, which is preferred for combinatorial multicolor coding, consists of 4'-6-diamidino-2-phenylinodole (DAPI), fluorescein (FITC), and the cyanine dyes Cy3, Cy3.5, Cy5, Cy5.5 and Cy7. Any subset of this preferred set can also be used where fewer combinations are required. The absorption and emission maxima, respectively, for these fluors are: DAPI (350 nm; 456 nm), FITC (490 nm; 520 nm), Cy3 (554 nm; 568 nm), Cy3.5 (581 nm; 588 nm), Cy5 (652 nm; 672 nm), Cy5.5 (682 nm; 703 nm) and Cy7 (755 nm; 778 nm). The excitation and emission spectra, extinction coefficients and quantum yield of these fluors are described by Ernst et al., *Cytometry* 10:3–10 (1989), Mujumdar et al., *Cytometry* 10:11–19 (1989), Yu, *Nucleic Acids Res.* 22:3226–3232 (1994), and Waggoner, *Meth. Enzymology* 246:362–373 (1995). These fluors can all be excited with a 75W Xenon arc.

To attain selectivity, filters with bandwidths in the range of 5 to 16 nm are preferred. To increase signal discrimination, the fluors can be both excited and detected at wavelengths far from their spectral maxima. Emission bandwidths can be made as wide as possible. For low-noise detectors, such as cooled CCD cameras, restricting the excitation bandwidth has little effect on attainable signal to noise ratios. A list of preferred filters for use with the preferred fluor set is listed in Table 1 of Speicher et al. It is important to prevent infra-red light emitted by the arc lamp from reaching the detector; CCD chips are extremely sensitive in this region. For this purpose, appropriate IR blocking filters can be inserted in the image path immediately in front of the CCD window to minimize loss of image quality. Image analysis software can then be used to count and analyze the spectral signatures of fluorescent dots.

Discrimination of individual signals in combinatorial multicolor coding can be enhanced by collapsing TS-DNA generated during amplification. As described above, this is preferably accomplished using collapsing detection probes, biotin-antibody conjugates, or a combination of both. A collapsed TS-DNA can occupy a space of no more than 0.3 microns in diameter. Based on this, it is expected that up to a million discrete signals can be detected in a 2.5 mm sample dot. Such discrimination also results in a large dynamic range for quantitative signal detection. For example, where two separate signals are detected in the same sample dot, a ratio of the two signals up to 1:500,000 can be detected. Thus, the relative numbers of different types of signals (such as multicolor codes) can be determined over a wide range. This is expected to allow determination of, for example, whether a particular target sequence is homozygous or heterozygous in a genomic DNA sample, whether a target sequence was inherited or represents a somatic mutation, and the genetic heterogeneity of a genomic DNA sample, such as a tumor sample. In the first case, a homozygous target sequence would produce twice the number of signals of a heterozygous target sequence. In the second case, an inherited target sequence would produce a number of signals equivalent to a homozygous or heterozygous signal (that is, a large number of signals), while a somatic mutation would produce a smaller number of signals depending on the source of the sample. In the third case, the relative number of cells, from which a sample is derived, that have particular target sequences can be determined. The more cells in the sample with a particular target sequence, the larger the signal.

(e) Detecting Groups of Target Sequences

Multiplex RCA assays are particularly useful for detecting mutations in genes where numerous distinct mutations are associated with certain diseases or where mutations in multiple genes are involved. For example, although the gene responsible for Huntington's chorea has been identified, a wide range of mutations in different parts of the gene occur among affected individuals. The result is that no single test has been devised to detect whether an individual has one or more of the many Huntington's mutations. A single LM-RCA assay can be used to detect the presence of one or more members of a group of any number of target sequences. This can be accomplished, for example, by designing an open circle probe (and associated gap oligonucleotides, if desired) for each target sequence in the group, where the target probe portions of each open circle probe are different but the sequence of the primer portions and the sequence of the detection tag portions of all the open circle probes are the same. All of the open circle probes are placed in the same OCP-target sample mixture, and the same primer and detection probe are used to amplify and detect TS-DNA. If any of the target sequences are present in the target sample, the OCP for that target will be ligated into a circle and the circle will be amplified to form TS-DNA. Since the detection tags on TS-DNA resulting from amplification of any of the OCPs are the same, TS-DNA resulting from ligation of any of the OCPs will be detected in that assay. Detection indicates that at least one member of the target sequence group is present in the target sample. This allows detection of a trait associated with multiple target sequences in a single tube or well.

If a positive result is found, the specific target sequence involved can be identified by using a multiplex assay. This can be facilitated by including an additional, different detection tag in each of the OCPs of the group. In this way, TS-DNA generated from each different OCP, representing each different target sequence, can be individually detected. It is convenient that such multiple assays need be performed only when an initial positive result is found.

The above scheme can also be used with arbitrarily chosen groups of target sequences in order to screen for a large number of target sequences without having to perform an equally large number of assays. Initial assays can be performed as described above, each using a different group of OCPs designed to hybridize to a different group of target sequences. Additional assays to determine which target sequence is present can then be performed on only those groups that produce TS-DNA. Such group assays can be further nested if desired.

(f) In Situ Detection Using RCA

In situ hybridization, and its most powerful implementation, known as fluorescent in situ hybridization (FISH), is of fundamental importance in cytogenetics. RCA can be adapted for use in FISH, as follows.

Open circle probes are ligated on targets on microscope slides, and incubated in situ with fluorescent precursors during rolling circle replication. The rolling circle DNA polymerase displaces the ligated open circle probe from the position where it was originally hybridized. However, the circle will remain topologically trapped on the chromosome unless the DNA is nicked (Nilsson et al. (1994)). The presence of residual chromatin may slow diffusion of the circle along the chromosome. Alternatively, fixation methods may be modified to minimize this diffusional effect. This diffusion has an equal probability of occurring in either of two directions along the chromosome, and hence net diffusional displacement may be relatively small during a 10 minute incubation. During this time rolling circle replication should generate a linear molecule of approximately 25,000 nucleotides containing approximately 2,500 bromodeoxyuridine moieties, which can be detected with a biotinylated anti-BUDR IgG (Zymed Labs, Inc.) and fluorescein-labeled avidin. This level of incorporation should facilitate recording of the image using a microscope-based CCD system. Diffusion may also be limited because the TS-DNA should be able to hybridize with the complement of the target strand.

A preferred method of in situ detection is Reporter Binding Agent Unimolecular Rolling Amplification (RBAURA), which is described below. In RBAURA, a reporter binding agent is used where the oligonucleotide portion serves as a rolling circle replication primer. Once the reporter binding agent is associated with a target molecule, an amplification target circle is hybridized to the rolling circle replication primer sequence of the reporter binding agent followed by amplification of the ATC by RCA. The resulting TS-DNA has the rolling circle replication primer sequence of the reporter binding agent at one end, thus anchoring the TS-DNA to the site of the target molecule. Peptide Nucleic Acid Probe Unimolecular Rolling Amplification (PNAPURA) and Locked Antibody Unimolecular Rolling Amplification (LAURA), described below, are preferred forms of RBAURA.

Localization of the TS-DNA for in situ detection can also be enhanced by collapsing the TS-DNA using collapsing detection probes, biotin-antibody conjugates, or both, as described above. Multiplexed in situ detection can be carried out as follows: Rolling circle replication is carried out using unlabeled nucleotides. The different TS-DNAs are then detected using standard multi-color FISH with detection probes specific for each unique target sequence or each unique detection tag in the TS-DNA. Alternatively, and preferably, combinatorial multicolor coding, as described above, can be used for multiplex in situ detection.

(g) Enzyme-Linked Detection

Amplified nucleic acid labeled by incorporation of labeled nucleotides can be detected with established enzyme-linked detection systems. For example, amplified nucleic acid labeled by incorporation of biotin-16-UTP (Boehringher Mannheim) can be detected as follows. The nucleic acid is immobilized on a solid glass surface by hybridization with a complementary DNA oligonucleotide (address probe) complementary to the target sequence (or its complement) present in the amplified nucleic acid. After hybridization, the glass slide is washed and contacted with alkaline phosphatase-streptavidin conjugate (Tropix, Inc., Bedford, Mass.). This enzyme-streptavidin conjugate binds to the biotin moieties on the amplified nucleic acid. The slide is again washed to remove excess enzyme conjugate and the chemiluminescent substrate CSPD (Tropix, Inc.) is added and covered with a glass cover slip. The slide can then be imaged in a Biorad Fluorimager.

(h) Collapse of Nucleic Acids

As described above, TS-DNA or TS-RNA, which are produced as extended nucleic acid molecules, can be collapsed into a compact structure. It should also be understood that the same collapsing procedure can be performed on any extended nucleic acid molecule. For example, genomic DNA, PCR products, viral RNA or DNA, and cDNA samples can all be collapsed into compact structures using the disclosed collapsing procedure. It is preferred that the nucleic acid to be collapsed is immobilized on a substrate. A preferred means of collapsing nucleic acids is by hybridizing one or more collapsing probes with the nucleic acid to be collapsed. Collapsing probes are oligonucleotides having a plurality of portions each complementary to sequences in the nucleic acid to be collapsed. These portions are referred to as complementary portions of the collapsing probe, where each complementary portion is complementary to a sequence in the nucleic acid to be collapsed. The sequences in the nucleic acid to be collapsed are referred to as collapsing target sequences. The complementary portion of a collapsing probe can be any length that supports specific and stable hybridization between the collapsing probe and the collapsing target sequence. For this purpose, a length of 10 to 35 nucleotides is preferred, with a complementary portion of a collapsing probe 16 to 20 nucleotides long being most preferred. It is preferred that at least two of the complementary portions of a collapsing probe be complementary to collapsing target sequences which are separated on the nucleic acid to be collapsed or to collapsing target sequences present in separate nucleic acid molecules. This allows each detection probe to hybridize to at least two separate collapsing target sequences in the nucleic acid sample. In this way, the collapsing probe forms a bridge between different parts of the nucleic acid to be collapsed. The combined action of numerous collapsing probes hybridizing to the nucleic acid will be to form a collapsed network of cross-linked nucleic acid. Collapsed nucleic acid occupies a much smaller volume than free, extended nucleic acid, and includes whatever detection probe or detection label hybridized to the nucleic acid. This result is a compact and discrete nucleic acid structure which can be more easily detected than extended nucleic acid. Collapsing nucleic acids is useful both for in situ hybridization applications and for multiplex detection because it allows detectable signals to be spatially separate even when closely packed. Collapsing nucleic acids is especially preferred for use with combinatorial multicolor coding.

Collapsing probes can also contain any of the detection labels described above. This allows detection of the collapsed nucleic acid in cases where separate detection probes or other means of detecting the nucleic acid are not employed. Preferred labels are biotin and fluorescent molecules. A particularly preferred detection probe is a molecular beacon. Molecular beacons are detection probes labeled with fluorescent moieties where the fluorescent moieties fluoresce only when the detection probe is hybridized. The use of such probes eliminates the need for removal of unhybridized probes prior to label detection because the unhybridized detection probes will not produce a signal. This is especially useful in multiplex assays.

TS-DNA collapse can also be accomplished through the use of ligand/ligand binding pairs (such as biotin and avidin) or hapten/antibody pairs. As described in Example 6, a nucleotide analog, BUDR, can be incorporated into TS-DNA during rolling circle replication. When biotinylated antibodies specific for BUDR and avidin are added, a cross-linked network of TS-DNA forms, bridged by avidin-biotin-antibody conjugates, and the TS-DNA collapses into a compact structure. Biotin-derivatized nucleic acid can be formed in many of the common nucleic acid replication operations such as cDNA synthesis, PCR, and other nucleic acid amplification techniques. In most cases, biotin can be incorporated into the synthesized nucleic acid by either incorporation of biotin-derivatized nucleotides or through the use of biotin-derivatized primers. Collapsing probes and biotin-mediated collapse can also be used together to collapse nucleic acids.

2. Nested LM-RCA

After RCA, a round of LM-RCA can be performed on the TS-DNA produced in the first RCA. This new round of LM-RCA is performed with a new open circle probe, referred to as a secondary open circle probe, having target probe portions complementary to a target sequence in the TS-DNA produced in the first round. When such new rounds of LM-RCA are performed, the amplification is referred to herein as nested LM-RCA. Nested LM-RCA is particularly useful for in situ hybridization applications of LM-RCA. Preferably, the target probe portions of the secondary OCP are complementary to a secondary target sequence in the spacer sequences of the TS-DNA produced in the first RCA. The complement of this secondary target sequence is present in the spacer portion of the OCP or ATC used in the first RCA. After mixing the secondary OCP with the TS-DNA, ligation and rolling circle amplification proceed as in LM-RCA. Each ligated secondary OCP generates a new TS-DNA. By having, for example, two secondary target sequence portions in the first round OCP, the new round of LM-RCA will yield two secondary TS-DNA molecules for every OCP or ATC repeat in the TS-DNA produced in the first RCA. Thus, the amplification yield of nested LM-RCA is about 2000-fold. The overall amplification using two cycles of RCA is thus 1000×2000=2,000,000. Nested LM-RCA can follow any DNA replication or transcription operation described herein, such as RCA, LM-RCA, secondary DNA strand displacement, strand displacement cascade amplification, or transcription.

Generally, nested LM-RCA involves, following a first RCA, (a) mixing a secondary open circle probe with the polymerase mixture, resulting in an OCP-TS mixture, and incubating the OCP-TS mixture under conditions promoting hybridization between the secondary open circle probe and the tandem sequence DNA, (b) mixing ligase with the OCP-TS mixture, resulting in a secondary ligation mixture, and incubating the secondary ligation mixture under conditions promoting ligation of the secondary open circle probe to form a secondary amplification target circle, (c) mixing a rolling circle replication primer with the secondary ligation mixture, resulting in a secondary primer-ATC mixture, and incubating the secondary primer-ATC mixture under conditions that promote hybridization between the secondary amplification target circle and rolling circle replication primer, (d) mixing DNA polymerase with the secondary primer-ATC mixture, resulting in a secondary polymerase-ATC mixture, and incubating the secondary polymerase-ATC mixture under conditions promoting replication of the secondary amplification target circle, where replication of the secondary amplification target circle results in formation of nested tandem sequence DNA.

An exonuclease digestion step can be added prior to performing the nested LM-RCA. This is especially useful when the target probe portions of the secondary open circle probe are the same as those in the first open circle probe. Any OCP which has been ligated will not be digested since ligated OCPs have no free end. A preferred way to digest OCPs that have hybridized to TS-DNA during the first round of LM-RCA is to use a special rolling circle replication primer containing at least about four phosphorothioate linkages between the nucleotides at the 5' end. Then, following rolling circle replication, the reaction mixture is subjected to exonuclease digestion. By using a 5' exonuclease unable to cleave these phosphorothioate linkages, only the OCPs hybridized to TS-DNA will be digested, not the TS-DNA. The TS-DNA generated during the first cycle of amplification will not be digested by the exonuclease because it is protected by the phosphorothioate linkages at the 5' end. A preferred exonuclease for this purpose is the T7 gene 6 exonuclease. The T7 gene 6 exonuclease can be inactivated prior to adding the secondary open circle probe by heating to 90° C. for 10 minutes.

By using an exonuclease digestion, nested LM-RCA can be performed using the same target sequence used in a first round of LM-RCA. This can be done, for example, generally as follows. After the first round of LM-RCA, the unligated open circle probes and gap oligonucleotides hybridized to TS-DNA are digested with T7 gene 6 exonuclease. The exonuclease is inactivated by heating for 10 minutes at 90° C. Then a second open circle probe is added. In this scheme, the second open circle probe has target probe portions complementary to the same original target sequence, but which contain a different (arbitrary) spacer region sequence. A second round of LM-RCA is then performed. In this second round, the target of the second open circle probes comprises the repeated target sequences contained in the TS-DNA generated by the first cycle. This procedure has the advantage of preserving the original target sequence in the amplified DNA obtained after nested LM-RCA.

Nested LM-RCA can also be performed on ligated OCPs or ATCs that have not been amplified. In this case, LM-RCA can be carried out using either ATCs or target-dependent ligated OCPs. This is especially useful for in situ detection. For in situ detection, the first, unamplified OCP, which is topologically locked to its target sequence, can be subjected to nested LM-RCA. By not amplifying the first OCP, it can remain hybridized to the target sequence while LM-RCA amplifies a secondary OCP topologically locked to the first OCP. This is illustrated in FIG. 12.

Figure 11A:
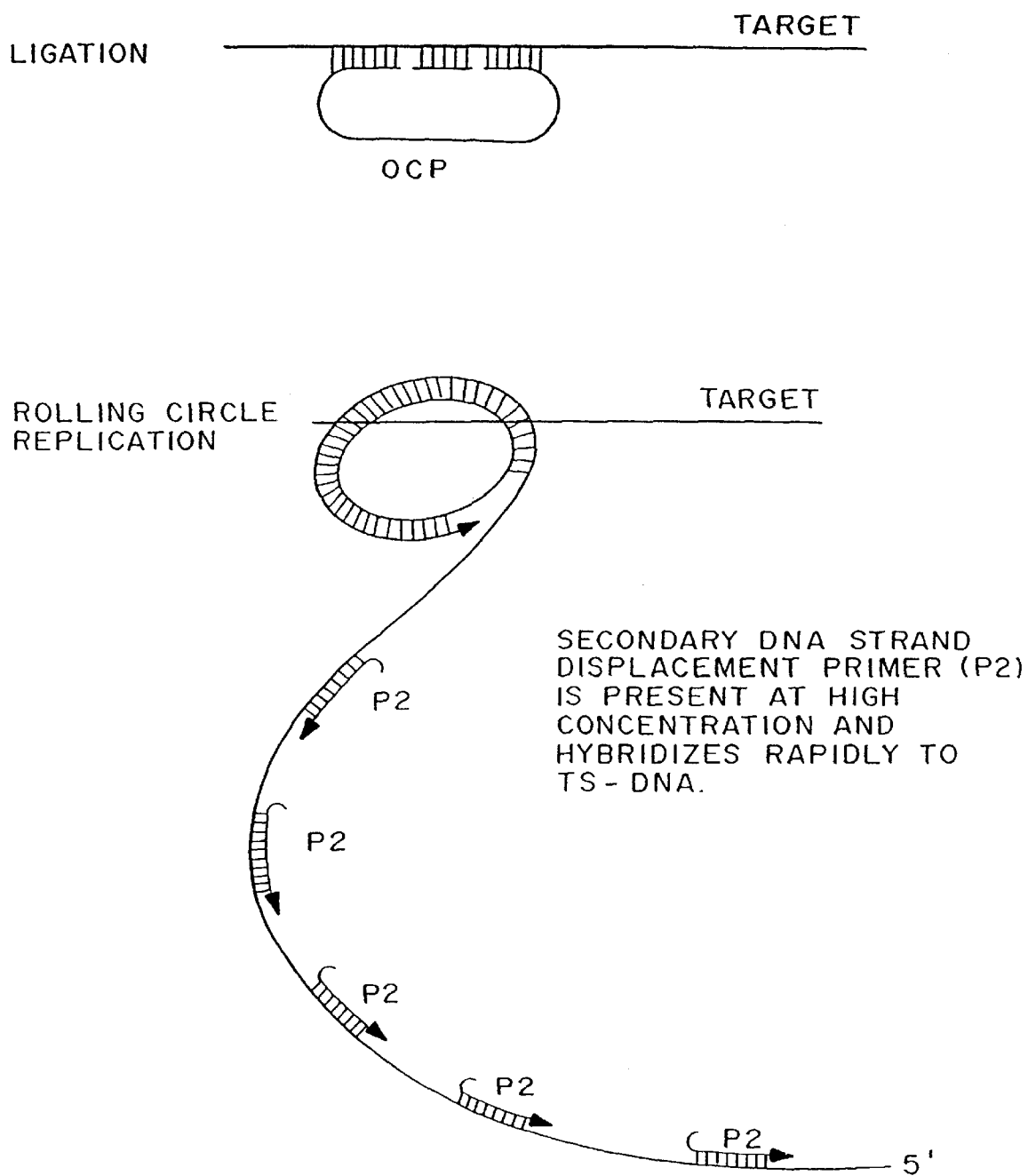
FIGS. 11A and 11B are diagrams of an example of secondary DNA strand displacement. Diagramed at the top of FIG. 11A is a gap oligonucleotide and an open circle probe hybridized to a target sequence. Diagramed at the bottom of FIG. 11A is the rolling circle replication product hybridized to secondary DNA strand displacement primers. Diagramed in FIG. 1B is secondary DNA strand displacement initiated from multiple primers.

3. Secondary DNA Strand Displacement and Strand Displacement Cascade Amplification Secondary DNA strand displacement is another way to amplify TS-DNA. Secondary DNA strand displacement is accomplished by hybridizing secondary DNA strand displacement primers to TS-DNA and allowing a DNA polymerase to synthesize DNA from these primed sites (FIG. 11). Since a complement of the secondary DNA strand displacement primer occurs in each repeat of the TS-DNA, secondary DNA strand displacement can result in a level of amplification similar to or larger than that obtained in RCT. The product of secondary DNA strand displacement is referred to as secondary tandem sequence DNA or TS-DNA-2.

Secondary DNA strand displacement can be accomplished by performing RCA to produce TS-DNA in a polymerase-ATC mixture, and then mixing secondary DNA strand displacement primer with the polymerase-ATC mixture, resulting in a secondary DNA strand displacement mixture, and incubating the secondary DNA strand displacement mixture under conditions promoting replication of the tandem sequence DNA. The secondary DNA strand displacement primer is complementary to a part of the OCP or ATC used to generated TS-DNA as described earlier. It is preferred that the secondary DNA strand displacement primer is not complementary to the rolling circle replication primer, or to a tertiary DNA strand displacement primer, if used.

Figure 11B:
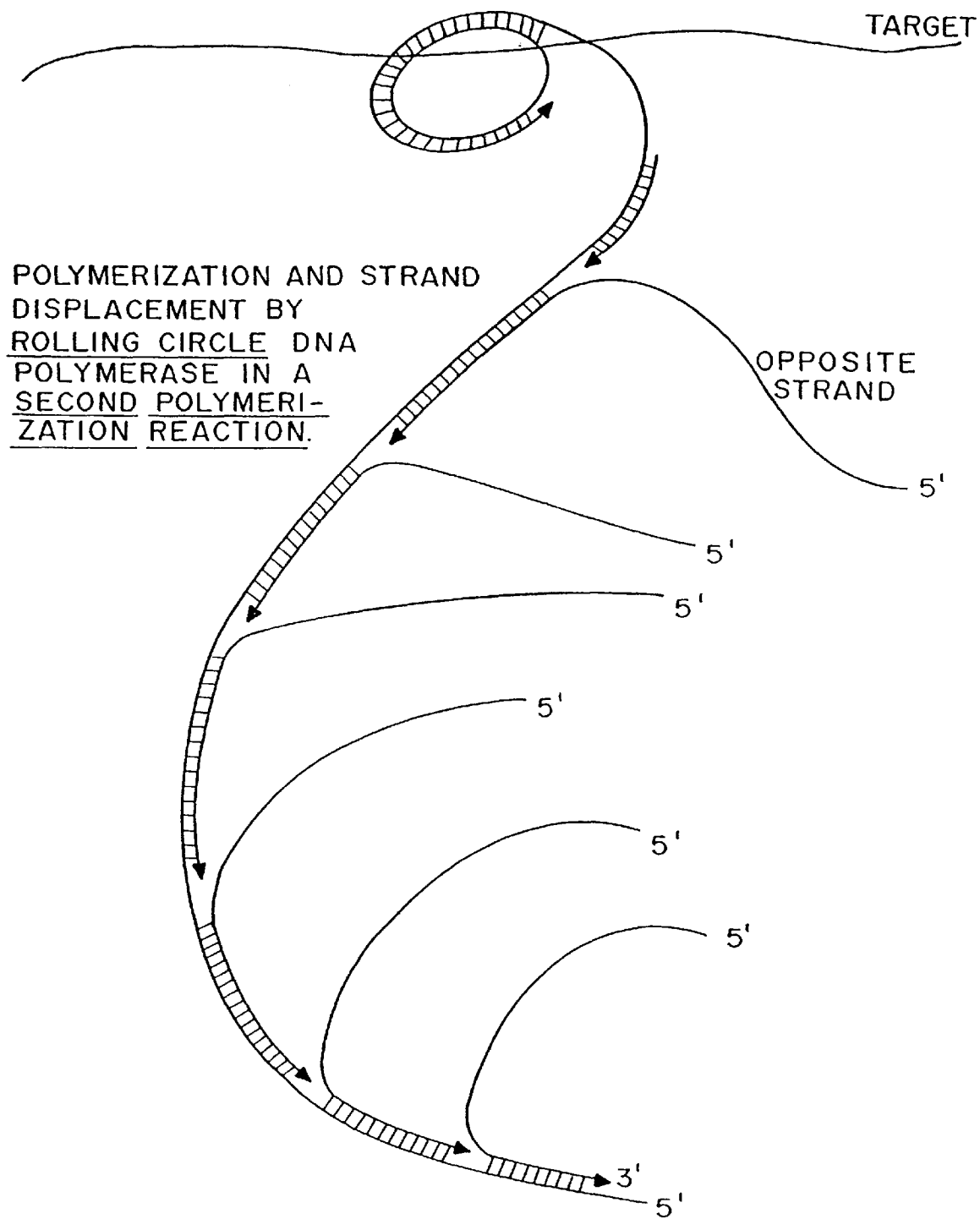

Secondary DNA strand displacement can also be carried out simultaneously with rolling circle replication. This is accomplished by mixing secondary DNA strand displacement primer with the polymerase-ATC mixture prior to incubating the mixture for rolling circle replication. For simultaneous rolling circle replication and secondary DNA strand displacement, it is preferred that the rolling circle DNA polymerase be used for both replications. This allows optimum conditions to be used and results in displacement of other strands being synthesized downstream as shown in FIG. 11B. Secondary DNA strand displacement can follow any DNA replication operation disclosed herein, such as RCA, LM-RCA or nested LM-RCA.

To optimize the efficiency of secondary DNA strand displacement, it is preferred that a sufficient concentration of secondary DNA strand displacement primer be used to obtain sufficiently rapid priming of the growing TS-DNA strand to outcompete any remaining unligated OCPs and gap oligonucleotides that might be present for binding to TS-DNA. In general, this is accomplished when the secondary DNA strand displacement primer is in very large excess compared to the concentration of single-stranded sites for hybridization of the secondary DNA strand displacement primer on TS-DNA. Optimization of the concentration of secondary DNA strand displacement primer can be aided by analysis of hybridization kinetics using methods such as those described by Young and Anderson, "Quantitative analysis of solution hybridization" in *Nucleic Acid Hybridization: A Practical Approach* (IRL Press, 1985) pages 47–71. For example, assuming that Φ29 DNA polymerase is used as the rolling circle DNA polymerase, TS-DNA is generated at a rate of about 53 nucleotides per second, and the rolling circle DNA polymerase generates approximately 10 copies of the amplification target circle in 19 seconds. Analysis of the theoretical solution hybridization kinetics for an OCP driver DNA (unligated OCP) present at a concentration of 80 nM (a typical concentration used for a LM-RCA ligation operation), and the theoretical solution hybridization kinetics for a secondary DNA strand displacement primer driver DNA present at a concentration of 800 nM, indicates that the secondary DNA strand displacement primer will bind to those 10 copies within 30 seconds, while unligated OCP will hybridize to less than one site in 30 seconds (8% of sites filled). If the concentration of DNA polymerase is relatively high (for this example, in the range of 100 to 1000 nM), the polymerase will initiate DNA synthesis at each available 3' terminus on the hybridized secondary DNA strand displacement primers, and these elongating TS-DNA-2 molecules will block any hybridization by the unligated OCP molecules. Alternatively, the efficiency of secondary DNA strand displacement can be improved by the removal of unligated open circle probes and gap oligonucleotides prior to amplification of the TS-DNA. In secondary DNA strand displacement, it is preferred that the concentration of secondary DNA strand displacement primer generally be from 500 nM to 5000 nM, and most preferably from 700 nM to 1000 nM.

As a secondary DNA strand displacement primer is elongated, the DNA polymerase will run into the 5' end of the next hybridized secondary DNA strand displacement molecule and will displace its 5' end. In this fashion a tandem queue of elongating DNA polymerases is formed on the TS-DNA template. As long as the rolling circle reaction continues, new secondary DNA strand displacement primers and new DNA polymerases are added to TS-DNA at the growing end of the rolling circle. The generation of TS-DNA-2 and its release into solution by strand displacement is shown diagrammatically in FIG. 11.

Generally, secondary DNA strand displacement can be performed by, simultaneous with or following RCA, mixing a secondary DNA strand displacement primer with the polymerase-ATC mixture, and incubating the polymerase-ATC mixture under conditions that promote both hybridization between the tandem sequence DNA and the secondary DNA strand displacement primer, and replication of the tandem sequence DNA, where replication of the tandem sequence DNA results in the formation of secondary tandem sequence DNA.

Figure 13:
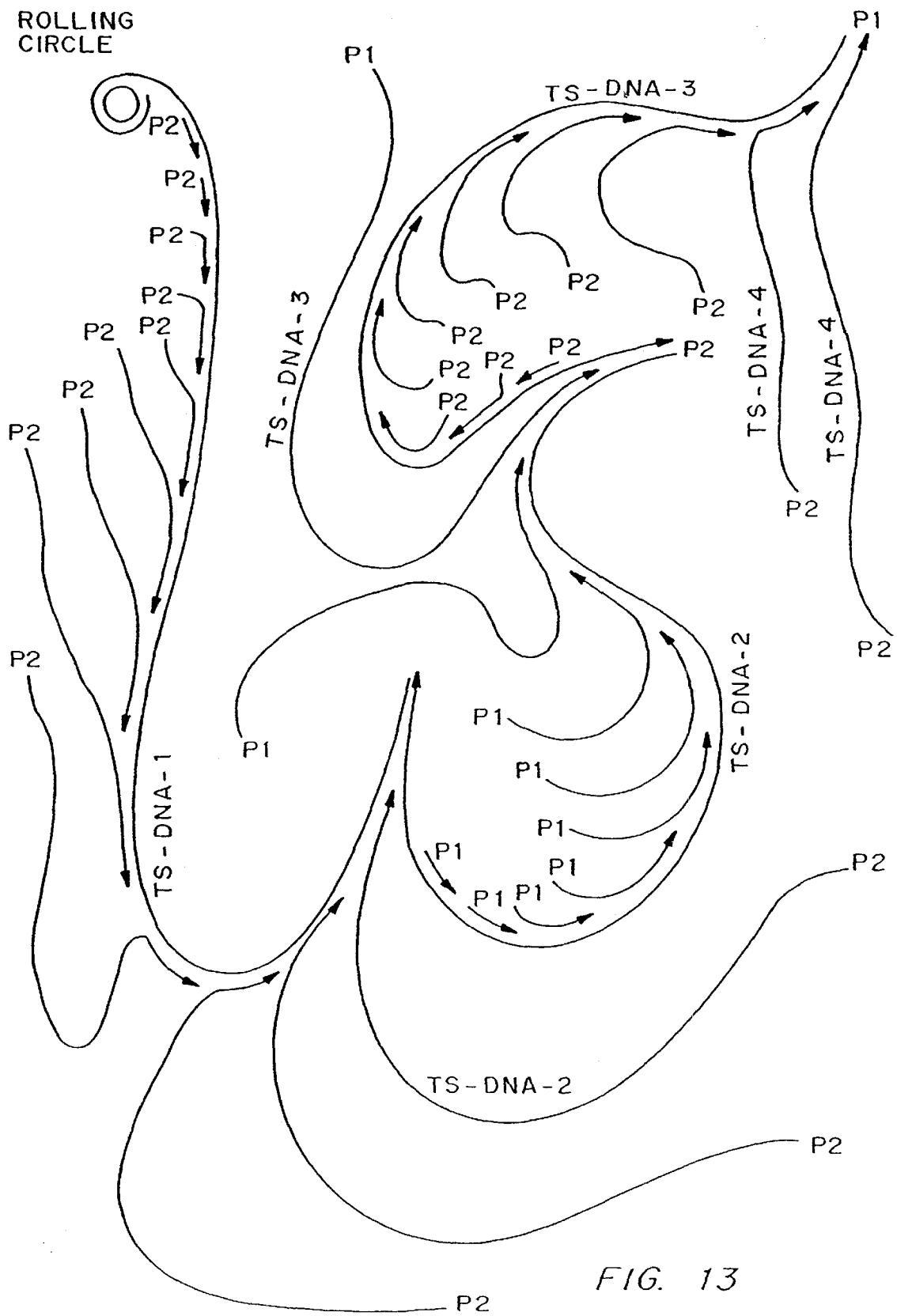
FIG. 13 is a diagram of an example of strand displacement cascade amplification. Diagramed is the synthesis and template relationships of four generations of TS-DNA. TS-DNA-1 is generated by rolling circle replication primed by the rolling circle replication primer. TS-DNA-2 and TS-DNA-4 are generated by secondary DNA strand displacement primed by a secondary DNA strand displacement primer (P2). TS-DNA-3 is generated by strand-displacing secondary DNA strand displacement primed by a tertiary DNA strand displacement primer (P1).
Figure 14:
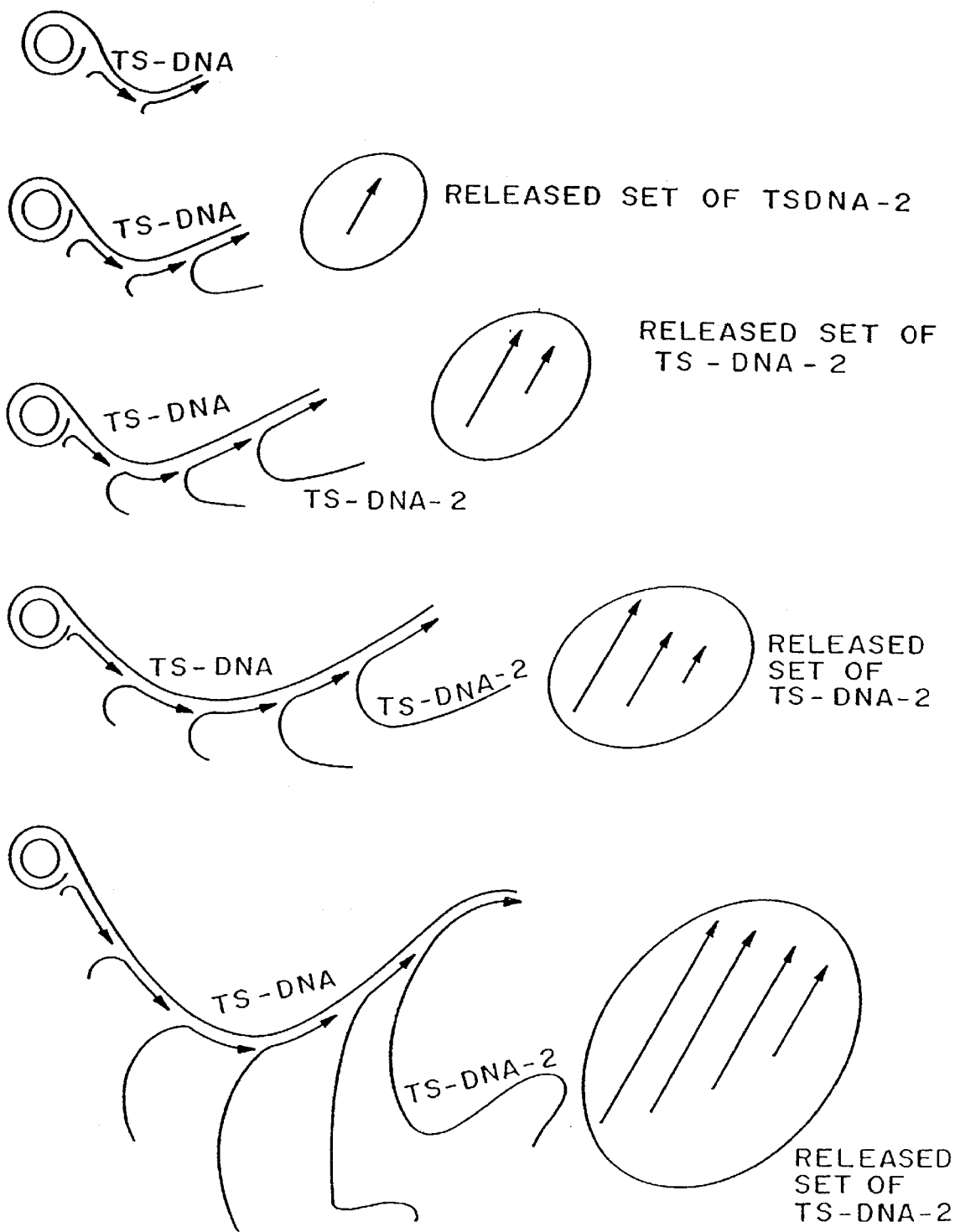
FIG. 14 is a diagram of an example of opposite strand amplification. Diagramed are five different stages of the reaction as DNA synthesis proceeds. TS-DNA-2 is generated by secondary DNA strand displacement of TS-DNA primed by the secondary DNA strand displacement primer. As rolling circle replication creates new TS-DNA sequence, the secondary DNA strand displacement primer hybridizes to the newly synthesized DNA and primes synthesis of another copy of TS-DNA-2.

When secondary DNA strand displacement is carried out in the presence of a tertiary DNA strand displacement primer, an exponential amplification of TS-DNA sequences takes place. This special and preferred mode of secondary DNA strand displacement is referred to as strand displacement cascade amplification (SDCA). In SDCA, illustrated in FIG. 13, a secondary DNA strand displacement primer primes replication of TS-DNA to form TS-DNA-2, as described above. The tertiary DNA strand displacement primer strand can then hybridize to, and prime replication of, TS-DNA-2 to form TS-DNA-3. Strand displacement of TS-DNA-3 by the adjacent, growing TS-DNA-3 strands makes TS-DNA-3 available for hybridization with secondary DNA strand displacement primer. This results in another round of replication resulting in TS-DNA-4 (which is equivalent to TS-DNA-2). TS-DNA-4, in turn, becomes a template for DNA replication primed by tertiary DNA strand displacement primer. The cascade continues this manner until the reaction stops or reagents become limiting. This reaction amplifies DNA at an almost exponential rate, although kinetics are not truly exponential because there are stochastically distributed priming failures, as well as steric hindrance events related to the large size of the DNA network produced during the reaction. In a preferred mode of SDCA, the rolling circle replication primer serves as the tertiary DNA strand displacement primer, thus eliminating the need for a separate primer. For this mode, the rolling circle replication primer should be used at a concentration sufficiently high to obtain rapid priming on the growing TS-DNA-2 strands. To optimize the efficiency of SDCA, it is preferred that a sufficient concentration of secondary DNA strand displacement primer and tertiary DNA strand displacement primer be used to obtain sufficiently rapid priming of the growing TS-DNA strand to outcompete TS-DNA for binding to its complementary TS-DNA, and, in the case of secondary DNA strand displacement primer, to outcompete any remaining unligated OCPs and gap oligonucleotides that might be present for binding to TS-DNA. In general, this is accomplished when the secondary DNA strand displacement primer and tertiary DNA strand displacement primer are both in very large excess compared to the concentration of single-stranded sites for hybridization of the DNA strand displacement primers on TS-DNA. For example, it is preferred that the secondary DNA strand displacement primer is in excess compared to the concentration of single-stranded secondary DNA strand displacement primer complement sites on TS-DNA, TS-DNA-3, TS-DNA-5, and so on. In the case of tertiary DNA strand displacement primer, it is preferred that the tertiary DNA strand displacement primer is in excess compared to the concentration of single-stranded tertiary DNA strand displacement primer complement sites on TS-DNA-2, TS-DNA-4, TS-DNA-6, and so on. Such an excess generally results in a primer hybridizing to its complement in TS-DNA before amplified complementary TS-DNA can hybridize. Optimization of primer concentrations can be aided by analysis of hybridization kinetics (Young and Anderson). In a strand displacement cascade amplification, it is preferred that the concentration of both secondary and tertiary DNA strand displacement primers generally be from 500 nM to 5000 nM, and most preferably from 700 nM to 1000 nM.

As in the case of secondary DNA strand displacement primers, if the concentration of DNA polymerase is sufficiently high, the polymerase will initiate DNA synthesis at each available 3' terminus on the hybridized tertiary DNA strand displacement primers, and these elongating TS-DNA-3 molecules will block any hybridization by TS-DNA-2. As a tertiary DNA strand displacement primer is elongated to form TS-DNA-3, the DNA polymerase will run into the 5' end of the next hybridized tertiary DNA strand displacement primer molecule and will displace its 5' end. In this fashion a tandem queue of elongating DNA polymerases is formed on the TS-DNA-2 template. As long as the reaction continues, new rolling circle replication primers and new DNA polymerases are added to TS-DNA-2 at the growing ends of TS-DNA-2. This hybridization/replication/strand displacement cycle is repeated with hybridization of secondary DNA strand displacement primers on the growing TS-DNA-3. The cascade of TS-DNA generation, and their release into solution by strand displacement is shown diagrammatically in FIG. 13.

Generally, strand displacement cascade amplification can be performed by, simultaneous with, or following, RCA, mixing a secondary DNA strand displacement primer and a tertiary DNA strand displacement primer with the polymerase-ATC mixture, and incubating the polymerase-ATC mixture under conditions that promote hybridization between the tandem sequence DNA and the secondary DNA strand displacement primer, replication of the tandem sequence DNA—where replication of the tandem sequence DNA results in the formation of secondary tandem sequence DNA—hybridization between the secondary tandem sequence DNA and the tertiary DNA strand displacement primer, and replication of secondary tandem sequence DNA—where replication of the secondary tandem sequence DNA results in formation of tertiary tandem sequence DNA (TS-DNA-3).

An example of the amplification yield generated by a strand displacement cascade amplification can be roughly estimated as follows. A rolling circle reaction that proceeds for 35 minutes at 53 nucleotides per second will generate 1236 copies of a 90 nucleotide amplification target circle. Thus, TS-DNA-1 contains 1236 tandem repeats. As these 1236 tandem repeats grow, priming and synthesis with secondary DNA strand displacement primers can generate at least 800 TS-DNA-2 molecules, taking into account delays and missed priming events. These new molecules will have lengths linearly distributed in the range of 1 to 799 repeats. Next, priming events on TS-DNA-2 by tertiary DNA strand displacement primers can generate at least 500 TS-DNA-3 molecules, taking into account delays and missed priming events, and these new molecules will have lengths linearly distributed in the range of 1 to 499 repeats. Then, priming events on TS-DNA-3 by secondary DNA strand displacement primers can generate at least 300 TS-DNA-4 molecules, taking into account delays and missed priming events, and these new molecules will have lengths linearly distributed in the range of 1 to 299 repeats. A conservative overall amplification yield, calculated as the product of only these four amplification levels, is estimated to be $1.86 \times 10^{10}$ repeats of the original OCP or ATC. Thus, SDCA is capable of extremely high amplification yields in an isothermal 35-minute reaction.

Secondary DNA strand displacement can also be carried out sequentially. Following a first round of secondary DNA strand displacement, a tertiary DNA strand displacement primer can be mixed with the polymerase-ATC mixture, and the polymerase-ATC mixture can be incubated under conditions that promote hybridization between the secondary tandem sequence DNA and the tertiary DNA strand displacement primer, and replication of secondary tandem sequence DNA, where replication of the secondary tandem sequence DNA results in formation of tertiary tandem sequence DNA (TS-DNA-3). This round of strand displacement replication can be referred to as tertiary DNA strand displacement. However, all rounds of strand displacement replication following rolling circle replication can also be referred to collectively as secondary DNA strand displacement.

A modified form of secondary DNA strand displacement results in amplification of TS-DNA and is referred to as opposite strand amplification (OSA). OSA is the same as secondary DNA strand displacement except that a special form of rolling circle replication primer is used that prevents it from hybridizing to TS-DNA-2. This can be accomplished in a number of ways. For example, the rolling circle replication primer can have an affinity tag coupled to its non-complementary portion allowing the rolling circle replication primer to be removed prior to secondary DNA strand displacement. Alternatively, remaining rolling circle replication primer can be crippled following initiation of rolling circle replication. One preferred form of rolling circle replication primer for use in OSA is designed to form a hairpin that contains a stem of perfectly base-paired nucleotides. The stem can contain 5 to 12 base pairs, most preferably 6 to 9 base pairs. Such a hairpin-forming rolling circle replication primer is a poor primer at lower temperature (less than 40° C.) because the hairpin structure prevents it from hybridizing to complementary sequences. The stem should involve a sufficient number of nucleotides in the complementary portion of the rolling circle replication primer to interfere with hybridization of the primer to the OCP or ATC. Generally, it is preferred that a stem involve 5 to 24 nucleotides, and most preferably 6 to 18 nucleotides, of the complementary portion of a rolling circle replication primer. A rolling circle replication primer where half of the stem involves nucleotides in the complementary portion of the rolling circle replication primer and the other half of the stem involves nucleotides in the non-complementary portion of the rolling circle replication primer is most preferred.

Such an arrangement eliminates the need for self-complementary regions in the OCP or ATC when using a hairpin-forming rolling circle replication primer.

When starting the rolling circle replication reaction, secondary DNA strand displacement primer and rolling circle replication primer are added to the reaction mixture, and the solution is incubated briefly at a temperature sufficient to disrupt the hairpin structure of the rolling circle replication primer but to still allow hybridization to the primer complement portion of the amplification target circle (typically greater than 50° C.). This incubation permits the rolling circle replication primer to hybridize to the primer complement portion of the amplification target circle. The solution is then brought to the proper temperature for rolling circle replication, and the rolling circle DNA polymerase is added. As the rolling circle reaction proceeds, TS-DNA is generated, and as the TS-DNA grows in length, the secondary DNA strand displacement primer rapidly initiates DNA synthesis with multiple strand displacement reactions on TS-DNA. These reactions generate TS-DNA-2, which is complementary to the TS-DNA. While TS-DNA-2 contains sequences complementary to the rolling circle replication primer, the primer is not able to hybridize nor prime efficiently at the reaction temperature due to its hairpin structure at this temperature. Thus, there is no further priming by the rolling circle replication primer and the only products generated are TS-DNA and TS-DNA-2. The reaction comes to a halt as rolling circle amplification stops and TS-DNA becomes completely double-stranded. In the course of the reaction, an excess of single-stranded TS-DNA-2 is generated.

Another form of rolling circle replication primer useful in OSA is a chimera of DNA and RNA. In this embodiment, the rolling circle primer has deoxyribonucleotides at its 3' end and ribonucleotides in the remainder of the primer. It is preferred that the rolling circle replication primer have five or six deoxyribonucleotides at its 3' end. By making part of the rolling circle replication primer with ribonucleotide, the primer can be selectively degraded by RNAse H when it is hybridized to DNA. Such hybrids form during OSA as TS-DNA-2 is synthesized. The deoxyribonucleotides at the 3' end allow the rolling circle DNA polymerase to initiate rolling circle replication. RNAse H can then be added to the OSA reaction to prevent priming of TS-DNA-2 replication.

An example of the amplification yield generated by OSA can be roughly estimated as follows. A rolling circle reaction that proceeds for 45 minutes at 53 nucleotides per second will generate tandem 1590 copies of a 90 nucleotide amplification target circle. Thus, TS-DNA-1 contains 1590 tandem repeats. As these 1590 tandem repeats grow, priming and displacement reactions with secondary DNA strand displacement primers will generate and release up to 1400 TS-DNA-2 molecules, and those new molecules will have lengths linearly distributed in the range of 1 to 1399 repeats. Calculations indicate that after 45 minutes, single-stranded TS-DNA-2 exceeds the amount of TS-DNA by a factor of about 700. OSA is useful for generating single-stranded DNA that contains the reverse complement of the target sequence. Overall amplification can be of the order of one million fold.

If secondary DNA strand displacement is used with a ligated OCP, unligated OCPs and gap oligonucleotides may be removed prior to rolling circle replication to eliminate competition between unligated OCPs and gap oligonucleotides and the secondary DNA strand displacement primer for hybridization to TS-DNA. An exception would be when secondary DNA strand displacement is used in conjunction with gap-filling LM-RCA, as described below. Alternatively, the concentration of the secondary DNA strand displacement primer can be made sufficiently high so that it outcompetes unligated OCP for hybridization to TS-DNA. This allows secondary DNA strand displacement to be performed without removal of unligated OCPs.

The DNA generated by secondary DNA strand displacement can be labeled and/or detected using the same labels, labeling methods, and detection methods described for use with TS-DNA. Most of these labels and methods are adaptable for use with nucleic acids in general. A preferred method of labeling the DNA is by incorporation of labeled nucleotides during synthesis.

4. Multiple Ligation Cycles

Using a thermostable DNA ligase, such as AMPLI-GASE® (Epicentre Technologies, Inc.), the open circle probe ligation reaction may be cycled a number of times between a annealing temperature (55° C.) and a melting temperature (96° C.). This cycling will produce multiple ligations for every target sequence present in the sample. For example, 8 cycles of ligation would provide and approximate 6-fold increase in the number of ligated circles. A preferred cycling protocol is 96° C. for 2 seconds, 55° C. for 2 seconds, and 60° C. for 70 seconds in a Perkin Elmer 9600 thermal cycler. If the number of cycles is kept small, the linearity of the amplification response should not be compromised.

The expected net amplification yield using eight ligation cycles, secondary fluorescent tags, and array hybridization can be calculated as shown below.

| | |
|---|---|
| Ligation cycling yield: | 6 |
| OSA yield | 1,000,000 |
| number of fluorescent tags/circle | 5 |
| 20% array hybridization yield | 0.2 |
| Net yield = 6 × 1,000,000 × 5 × 0.2 = 6,000,000 | |
| 100 target molecules × 6,000,000 = 6 × $10^8$ fluors bound on the surface | |

5. Transcription Following RCA (RCT)

Once TS-DNA is generated using RCA, further amplification can be accomplished by transcribing the TS-DNA from promoters embedded in the TS-DNA. This combined process, referred to as rolling circle replication with transcription (RCT), or ligation mediated rolling circle replication with transcription (LM-RCT), requires that the OCP or ATC from which the TS-DNA is made have a promoter portion in its spacer region. The promoter portion is then amplified along with the rest of the OCP or ATC resulting in a promoter embedded in each tandem repeat of the TS-DNA (FIG. 8). Since transcription, like rolling circle amplification, is a process that can go on continuously (with re-initiation), multiple transcripts can be produced from each of the multiple promoters present in the TS-DNA. RCT effectively adds another level of amplification of ligated OCP sequences.

Generally, RCT can be accomplished by performing RCA to produce TS-DNA in a polymerase-OCP mixture or polymerase-ATC mixture, and then mixing RNA polymerase with the polymerase-OCP mixture or polymerase-ATC mixture, resulting in a transcription mixture, and incubating the transcription mixture under conditions promoting transcription of the tandem sequence DNA. The OCP or ATC must include the sequence of a promoter for the RNA polymerase (a promoter portion) in its spacer region for RCT to work. The transcription step in RCT generally can be performed using established conditions for in vitro transcription of the particular RNA polymerase used. Preferred conditions are described in the Examples. Alternatively, transcription can be carried out simultaneously with rolling circle replication. This is accomplished by mixing RNA polymerase with the polymerase-OCP mixture or polymerase-ATC mixture prior to incubating the mixture for rolling circle replication. For simultaneous rolling circle replication and transcription the rolling circle DNA polymerase and RNA polymerase must be active in the same conditions. Such conditions can be optimized in order to balance and/or maximize the activity of both polymerases. It is not necessary that the polymerase achieve their maximum activity, a balance between the activities is preferred. Transcription can follow any DNA replication operation described herein, such as RCA, LM-RCA, nested LM-RCA, secondary DNA strand displacement, or strand displacement cascade amplification.

The transcripts generated in RCT can be labeled and/or detected using the same labels, labeling methods, and detection methods described for use with TS-DNA. Most of these labels and methods are adaptable for use with nucleic acids in general. A preferred method of labeling RCT transcripts is by direct labeling of the transcripts by incorporation of labeled nucleotides, most preferably biotinylated nucleotides, during transcription.

6. Gap-Filling Ligation

The gap space formed by an OCP hybridized to a target sequence is normally occupied by one or more gap oligonucleotides as described above. Such a gap space may also be filled in by a gap-filling DNA polymerase during the ligation operation. As an alternative, the gap space can be partially bridged by one or more gap oligonucleotides, with the remainder of the gap filled using DNA polymerase. This modified ligation operation is referred to herein as gap-filling ligation and is the preferred form of the ligation operation. The principles and procedure for gap-filling ligation are generally analogous to the filling and ligation performed in gap LCR (Wiedmann et al., *PCR Methods and Applications* (Cold Spring Harbor Laboratory Press, Cold Spring Harbor Laboratory, N.Y., 1994) pages S51–S64; Abravaya et al., *Nucleic Acids Res.,* 23(4):675–682 (1995); European Patent Application EP0439182 (1991)). In the case of LM-RCA, the gap-filling ligation operation is substituted for the normal ligation operation. Gap-filling ligation provides a means for discriminating between closely related target sequences. An example of this is described in Example 3. Gap-filling ligation can be accomplished by using a different DNA polymerase, referred to herein as a gap-filling DNA polymerase. Suitable gap-filling DNA polymerases are described above. Alternatively, DNA polymerases in general can be used to fill the gap when a stop base is used. The use of stop bases in the gap-filling operation of LCR is described in European Patent Application EP0439182. The principles of the design of gaps and the ends of flanking probes to be joined, as described in EP0439182, is generally applicable to the design of the gap spaces and the ends of target probe portions described herein.

To prevent interference of the gap-filling DNA polymerase with rolling circle replication, the gap-filling DNA polymerase can be removed by extraction or inactivated with a neutralizing antibody prior to performing rolling circle replication. Such inactivation is analogous to the use of antibodies for blocking Taq DNA polymerase prior to PCR (Kellogg et al., *Biotechniques* 16(6):1134–1137 (1994)).

Gap-filling ligation is also preferred because it is highly compatible with exponential amplification of OCP sequences similar to the strand displacement cascade amplification (SDCA) as described above. As TS-DNA is formed during rolling circle replication, unligated OCP molecules present in the reaction hybridize to TS-DNA, leaving gap spaces between every OCP repeat. The hybridized OCP molecules serve as primers for secondary DNA synthesis.

Generally, gap-filling LM-RCA can be performed by, in an LM-RCA reaction, (1) using a target sequence with a central region located between a 5' region and a 3' region, and an OCP where neither the left target probe portion of the open circle probe nor the right target probe portion of the open circle probe is complementary to the central region of the target sequence, and (2) mixing gap-filling DNA polymerase with the OCP-target sample mixture.

7. Ligation Mediated Rolling Circle Amplification With Combinatorial Multicolor Coding A preferred form of rolling circle amplification involving multiplex detection is Ligation Mediated Rolling Circle Amplification with Combinatorial Multicolor Coding (LM-RCA-CMC), which is a combination of LM-RCA and CMC, both as described above. In LM-RCA-CMC, open circle probes and corresponding gap oligonucleotides are designed for the detection of a number of distinct target sequences. DNA samples to be tested are incorporated into a solid-state sample, as described above. The solid-state substrate is preferably a glass slide and the solid-state sample preferably incorporates up to 256 individual target or assay samples arranged in dots. Multiple solid-state samples can be used to either test more individual samples, or to increase the number of distinct target sequences to be detected. In the later case, each solid-state sample has an identical set of sample dots, and LM-RCA will be carried out using a different set of open circle probes and gap oligonucleotides, collectively referred to as a probe set, for each solid-state sample. This allows a large number of individuals and target sequences to be assayed in a single assay. By using up to six different labels, combinatorial multicolor coding allows up to 63 distinct targets to be detected on a single solid-state sample. When using multiple solid-state substrates and performing LM-RCA with a different set of OCPs and gap oligonucleotides for each solid-state substrate, the same labels can be used with each solid-state sample (although differences between OCPs in each set may require the use of different detection probes). For example, 10 replica slides, each with 256 target sample dots, can be subjected to LM-RCA using different sets of OCPs and gap oligonucleotides, where each set is designed for combinatorial multicolor coding of 63 targets. This result in an assay for detection of 630 different target sequences. Where two or more different target sequences are closely spaced in the DNA of the target or assay sample (for example, when multiple closely spaced mutations of the same gene are targets), it is preferred that the OCPs and gap oligonucleotides for each of the closely spaced target sequences be placed in a different probe set. For this purpose, it is considered that target sequences within 20 nucleotides of each other on a DNA molecule in a target or assay sample are closely spaced. It is not required that multiple targets within the same gene be detected with a different probe set. It is merely preferred that closely spaced target sequences, as defined above, be separately probed.

After rolling circle amplification, a cocktail of detection probes is added, where the cocktail contains color combinations that are specific for each OCP. The design and combination of such detection probes for use in combinatorial multicolor coding is described above. It is preferred that the OCPs be designed with combinatorially coded detection tags to allow use of a single set of singly labeled detection probes. It is also preferred that collapsing detection probes be used. As described above, collapsing probes contain two complementary portions. This allows each detection probe to hybridize to two detection tags in TS-DNA. In this way, the detection probe forms a bridge between different parts of the TS-DNA. The combined action of numerous collapsing detection probes hybridizing to TS-DNA will be to form a collapsed network of cross-linked TS-DNA. Collapsed TS-DNA occupies a much smaller volume than free, extended TS-DNA, and includes whatever detection label present on the detection probe. This result is a compact and discrete detectable signal for each TS-DNA. Probe binding will, upon collapse, trap a unique combination of colors that was designed a priory on the basis of each probe sequence.

As discussed above, rolling circle amplification can be engineered to produce TS-DNA of different lengths for different OCPs. Such products can be distinguish simply on the basis of the size of the detection signal they generate. Thus, the same set of detection probes could be used to distinguish two different sets of generated TS-DNA. In this scheme, two different TS-DNAs, each of a different size class but assigned the same color code, would be distinguished by the size of the signal produced by the hybridized detection probes. In this way, a total of 126 different targets can be distinguished on a single solid-state sample using a code with 63 combinations, since the signals will come in two flavors, low amplitude and high amplitude. Thus one could, for example, use the low amplitude signal set of 63 probes for detection of an oncogene mutations, and the high amplitude signal set of 63 probes for the detection of a tumor suppressor p53 mutations.

8. Reporter Binding Agent Unimolecular Rolling Amplification

Reporter Binding Agent Unimolecular Rolling Amplification (RBAURA) is a form of RCA where a reporter binding agent provides the rolling circle replication primer for amplification of an amplification target circle. In RBAURA, the oligonucleotide portion of the reporter binding agent serves as a rolling circle replication primer. RBAURA allows RCA to produce an amplified signal (that is, TS-DNA) based on association of the reporter binding agent to a target molecule. The specific primer sequence that is a part of the reporter binding agent provides the link between the specific interaction of the reporter binding agent to a target molecule (via the affinity portion of the reporter binding agent) and RCA. In RBAURA, once the reporter binding agent is associated with a target molecule, an amplification target circle is hybridized to the rolling circle replication primer sequence of the reporter binding agent, followed by amplification of the ATC by RCA. The resulting TS-DNA incorporates the rolling circle replication primer sequence of the reporter binding agent at one end, thus anchoring the TS-DNA to the site of the target molecule. RBAURA is a preferred RCA method for in situ detections. For this purpose, it is preferred that the TS-DNA is collapsed using collapsing detection probes, biotin-antibody conjugates, or both, as described above. RBAURA can be performed using any target molecule. Preferred target molecules are nucleic acids, including amplified nucleic acids such as TS-DNA and amplification target circles, antigens and ligands. Examples of the use of such target molecules are illustrated in FIGS. 25A to 29B. Peptide Nucleic Acid Probe Unimolecular Rolling Amplification (PNAPURA) and Locked Antibody Unimolecular Rolling Amplification (LAURA), described below, are preferred forms of RBAURA.

(a) Peptide Nucleic Acid Probe Unimolecular Rolling Amplification

In PNAPURA, chimeric PNA:DNA molecules are used as reporter binding probes, referred to as PNA reporter binding probes. The oligonucleotide portion of the PNA reporter binding agent serves as a rolling circle replication primer. The affinity portion of the PNA reporter binding probe is a peptide nucleic acid, preferably 12 to 20 nucleotide bases in length and more preferably 15 to 18 bases in length, designed to hybridize to a target nucleic acid sequence of interest. In PNAPURA, the PNA reporter binding probe is first allowed to hybridize to a target sequence (illustrated in FIG. 25A). Once the PNA reporter binding probe is hybridized to a target sequence, an amplification target circle is hybridized to the rolling circle replication primer sequence of the PNA reporter binding probe (illustrated in FIG. 25B), followed by amplification of the ATC by RCA. The resulting TS-DNA incorporates the rolling circle replication primer sequence of the PNA reporter binding probe at one end, thus anchoring the TS-DNA to the site of the target molecule. Reporter binding agents having any form of affinity portion can be used in a similar manner.

PNAPURA is preferably performed with a solid-state substrate and in combination with CMC. For this purpose, DNA samples to be tested are incorporated into a solid-state sample, as described above. The solid-state substrate is preferably a glass slide and the solid-state sample preferably incorporates up to 256 individual target or assay samples arranged in dots. Multiple solid-state samples can be used to either test more individual samples, or to increase the number of distinct target sequences to be detected. In the later case, each solid-state sample has an identical set of samples dots, and PNAPURA will be carried out using a different set of PNA reporter binding probes and amplification target circles, collectively referred to as a probe set, for each solid-state sample. This allows a large number of individuals and target sequences to be assayed in a single assay. By using up to six different labels, combinatorial multicolor coding allows up to 63 distinct targets to be detected on a single solid-state sample. When using multiple solid-state substrates and performing PNAPURA with a different set of PNA reporter binding probes and amplification target circles for each solid-state substrate, the same labels can be used with each solid-state sample (although differences between ATCs in each set may require the use of different detection probes). For example, 10 replica slides, each with 256 target sample dots, can be subjected to PNAPURA using 10 different sets of PNA reporter binding probes and amplification target circles, where each set is designed for combinatorial multicolor coding of 63 targets. This results in an assay for detection of 630 different target sequences. Where two or more different target sequences are closely spaced in the DNA of the target or assay sample (for example, when multiple closely spaced mutations of the same gene are targets), it is preferred that the PNA reporter binding probe for each of the closely spaced target sequences be placed in a different probe set. For this purpose, it is considered that target sequences within 20 nucleotides of each other on a DNA molecule in a target or assay sample are closely spaced. It is not required that multiple targets within the same gene be detected with a different probe set. It is merely preferred that closely spaced target sequences, as defined above, be separately probed.

After rolling circle amplification, a cocktail of detection probes is added, where the cocktail contains color combinations that are specific for each ATC. The design and combination of such detection probes for use in combinatorial multicolor coding is described above. It is preferred that the ATCs be designed with combinatorially coded detection tags to allow use of a single set of singly labeled detection probes. It is also preferred that collapsing detection probes be used. As described above, collapsing probes contain two complementary portions. This allows each detection probe to hybridize to two detection tags in TS-DNA. In this way, the detection probe forms a bridge between different parts of the TS-DNA. The combined action of numerous collapsing detection probes hybridizing to TS-DNA will be to form a collapsed network of cross-linked TS-DNA. Collapsed TS-DNA occupies a much smaller volume than free, extended TS-DNA, and includes whatever detection label present on the detection probe. This result is a compact and discrete detectable signal for each TS-DNA. Probe binding will, upon collapse, trap a unique combination of colors that was designed a priory on the basis of each probe sequence.

(b) Locked Antibody Unimolecular Rolling Amplification

In LAURA, a covalently coupled antibody and oligonucleotide is used as a reporter binding agent. The oligonucleotide portion of the reporter binding agent serves as a rolling circle replication primer. The affinity portion of the reporter binding agent is an antibody specific for a target molecule of interest. The reporter binding agent is conjugated to the target molecule as in a conventional immunoassay (illustrated in FIG. 29A). Unlike conventional immunoassays, detection of this interaction is mediated by rolling circle amplification. After conjugation and washing, the immune complexes are fixed in place with a suitable fixation reaction (for example, methanol-acetic acid) to immobilize the antibody. As in conventional immunoassays, unconjugated antibodies (in this case, in the form of reporter binding agents) are removed by washing. Once the reporter binding agent is conjugated to a target molecule, an amplification target circle is hybridized to the rolling circle replication primer sequence of the reporter binding agent (illustrated in FIG. 29B), followed by amplification of the ATC by RCA. The resulting TS-DNA incorporates the rolling circle replication primer sequence of the reporter binding agent at one end, thus anchoring the TS-DNA to the site of the target molecule.

In a variant of this method, the oligonucleotide portion of the reporter binding agent can be a peptide nucleic acid, instead of DNA. After fixation of the reporter binding agent to the target molecule, the PNA can be hybridized an oligonucleotide that contains a portion complementary to the PNA, referred to as the complementary portion, and a portion that remains single stranded, referred to as the primer portion. The primer portion can then be used as a rolling circle primer in LAURA as described above.

LAURA is preferably performed with a solid-state substrate and in combination with CMC. For this purpose, DNA samples to be tested are incorporated into a solid-state sample, as described above. The solid-state substrate is preferably a glass slide and the solid-state sample preferably incorporates up to 256 individual target or assay samples arranged in dots. Multiple solid-state samples can be used to either test more individual samples, or to increase the number of distinct target sequences to be detected. In the later case, each solid-state sample has an identical set of samples dots, and LAURA will be carried out using a different set of reporter binding agents and amplification target circles, collectively referred to as a probe set, for each solid-state sample. This allows a large number of individuals and target sequences to be assayed in a single assay. By using up to six different labels, combinatorial multicolor coding allows up to 63 distinct targets to be detected on a single solid-state sample. When using multiple solid-state substrates and performing LAURA with a different set of reporter binding agents and amplification target circles for each solid-state substrate, the same labels can be used with each solid-state sample (although differences between ATCs in each set may require the use of different detection probes). For example, 10 replica slides, each with 256 target sample dots, can be subjected to LAURA using 10 different sets of reporter binding agents and amplification target circles, where each set is designed for combinatorial multicolor coding of 63 targets. This results in an assay for detection of 630 different target sequences. Where two or more different target sequences are closely spaced in the DNA of the target or assay sample, it is preferred that the PNA reporter binding probe for each of the closely spaced target sequences be placed in a different probe set, as discussed above.

After rolling circle amplification, a cocktail of detection probes is added, where the cocktail contains color combinations that are specific for each ATC. The design and combination of such detection probes for use in combinatorial multicolor coding is described above. It is preferred that the ATCs be designed with combinatorially coded detection tags to allow use of a single set of singly labeled detection probes. It is also preferred that collapsing detection probes be used. As described above, collapsing probes contain two complementary portions. This allows each detection probe to hybridize to two detection tags in TS-DNA. In this way, the detection probe forms a bridge between different parts of the TS-DNA. The combined action of numerous collapsing detection probes hybridizing to TS-DNA will be to form a collapsed network of cross-linked TS-DNA. Collapsed TS-DNA occupies a much smaller volume than free, extended TS-DNA, and includes whatever detection label present on the detection probe. This result is a compact and discrete detectable signal for each TS-DNA. Probe binding will, upon collapse, trap a unique combination of colors that was designed a priory on the basis of each probe sequence.

9. Primer Extension Sequencing

Following amplification, the nucleotide sequence of the amplified sequences can be determined either by conventional means or by primer extension sequencing of amplified target sequence. Primer extension sequencing is also referred herein as chain terminating primer extension sequencing. A preferred form of chain terminating primer extension sequencing, referred to herein as single nucleotide primer extension sequencing, involves the addition of a single chain-terminating nucleotide to a primer (no other nucleotides are added). This form of primer extension sequencing allows interrogation (and identification) of the nucleotide immediately adjacent to the region to which the primer is hybridized. Two preferred modes of single nucleotide primer extension sequencing are disclosed.

(a) Unimolecular Segment Amplification and Sequencing

Unimolecular Segment Amplification and Sequencing (USA-SEQ) involves interrogation of a single nucleotide in an amplified target sequence by incorporation of a specific and identifiable nucleotide based on the identity of the interrogated nucleotide. In Unimolecular Segment Amplification and Sequencing (USA-SEQ) individual target molecules are amplified by rolling circle amplification. Following amplification, an interrogation primer is hybridized immediately 5' of the base in the target sequence to be interrogated, and a single chain-terminating nucleotide is added to the end of the primer. The identity of the interrogated base determines which nucleotide is added. By using nucleotides with unique detection signatures (e.g. different fluorescent labels), the identity of the interrogated base can be determined. The interrogation primer can be a pre-formed single molecule or it can be formed by hybridizing one or more interrogation probes to the amplified target sequences and ligating them together to form an interrogation primer.

USA-SEQ is useful for identifying the presence of multiple distinct sequences in a mixture of target sequences. In particular, if the sample from which the target sequences are amplified contains different forms of the target sequence (that is, different alleles of the target sequence), then USA-SEQ can identify not only their presence but also provide information on the relative abundance of the different forms. This is possible because each TS-DNA molecule is amplified from a single target sequence molecule and each TS-DNA molecule can be individually detected.

Primer extension sequencing can be performed generally as follows. After amplification of a target nucleic acid sequence using any of the rolling circle amplification techniques disclosed herein, an interrogation primer is hybridized to the amplified nucleic acid (for example, to TS-DNA). The mixture of amplified nucleic acid and interrogation primer is referred to as an interrogation mixture. The interrogation primer is designed to hybridize adjacent to (that is 3' of) the nucleotide in the TS-DNA that is to be interrogated (that is, sequenced). Of course, since the target sequence is repeated numerous times in a TS-DNA molecule, numerous interrogation probes will hybridize to a single TS-DNA molecule. Next, at least two differently labeled chain terminating nucleotides and DNA polymerase are added to the interrogation mixture. This results in addition of a single nucleotide to the end of the interrogation primer, the identity of which is based on the identity of the interrogated nucleotide (that is, the first template nucleotide after the end of the interrogation primer). Finally, the identity of the nucleotide incorporated for each TS-DNA molecule is determined by fluorescence microscopy. For this purpose, it is preferred that the TS-DNA be collapsed prior to detection of the incorporated nucleotide. Example 9 describes an example of the use of USA-SEQ to detect of homo- or heterozygosity at a particular nucleotide in a genetic sample. It is specifically contemplated that primer extension sequencing can be used to determine the identity of one or more specific nucleotides in any amplified nucleic acid, including nucleotides derived from a target nucleic acid, and nucleotides present as arbitrarily chosen sequences in the spacer region of an OCP or ATC. In the later case, primer extension sequencing can be used to distinguish or identify a specific OCP or ATC which has been amplified. As described elsewhere, the detection of specific OCPs and ATCs, from among an original pool of OCPs or ATCs, amplified based on the presence of a specific target molecule or nucleic acid is a preferred use for the disclosed amplification and detection methods.

Preferred chain terminating nucleotides are dideoxynucleotides. Other known chain terminating nucleotides (for example, nucleotides having substituents at the 3' position) can also be used. Fluorescent forms of dideoxynucleotides are known for use in conventional chain terminating sequencing, any of which are suitable for the disclosed primer extension sequencing. Preferred forms of fluorescent or haptenated chain-terminating nucleotides include fluorescein-N6-ddATP, biotin-N6-ddATP, fluorescein-12-ddATP, fluorescein-12-ddCTP, fluorescein-12-ddGTP, fluorescein-12-ddUTP, lissamine-5-ddGTP, eosin-6-ddCTP, coumarin-ddUTP, tetramethylmodamine-6-ddUTP, Texas Red-5-ddATP (all available from NEN Life Sciences).

(b) Degenerate Probe Primer Extension Sequencing

Degenerate probe primer extension sequencing involves sequential addition of degenerate probes to an interrogation primer hybridized to amplified target sequences. Addition of multiple probes is prevented by the presence of a removable blocking group at the 3' end. After addition of the degenerate probes, the blocking group is removed and further degenerate probes can be added or, as the final operation, the nucleotide next to the end of the interrogation probe, or the last added degenerate probe, is interrogated as described for single nucleotide primer extension sequencing to determine its identity. It is contemplated that degenerate probes having any form of removable 3' end block can be used in a primer extension sequencing procedure. A preferred form of removable blocking group is the cage structure, as described herein. In each case, conditions specific for removal of the particular blocking structure are used as appropriate. A preferred form of amplification and degenerate probe primer extension sequencing is Unimolecular Segment Amplification and CAGE Sequencing (USA-CAGESEQ).

Primer extension sequencing using blocked degenerate probes (that is, degenerate probe primer extension sequencing, of which CAGESEQ is a preferred form) can be performed generally as follows. One or more interrogation probes and a plurality of degenerate probes are mixed with an DNA sample to be sequenced to form an interrogation mixture. It is preferred that the nucleic acid to be sequenced is a nucleic acid amplified using any of the rolling circle amplification techniques disclosed herein. In this case it is further preferred that the nucleic acid to be sequenced is amplified form an amplification target circle formed by gap-filling ligation of an open circle probe. For degenerate probe primer extension sequencing it is also preferred that a full set of degenerate probes, as described above, be used. The interrogation probes are designed to hybridize to the target nucleic acid such that the region of the target nucleic acid to be sequenced lies past the 3' end of the interrogation probe. The interrogation mixture is incubated under conditions that promotes hybridization of the interrogation probe and the degenerate primers to the nucleic acid to be sequenced. Only one of the degenerate probes will form a perfect hybrid with the nucleic acid sequence adjacent to the interrogation probe. It is preferred that incubation conditions be chosen which will favor the formation of perfect hybrids. Once the interrogation and degenerate probes are hybridized, the interrogation mixture is subjected to ligation. This joins the interrogation probe and the degenerate primer. Finally, the blocking group present at the 3' end of the ligated degenerate probe is removed. When using photolabile caged oligonucleotides, the cage structure is removed by exposure to appropriate light. This makes the end of the ligated degenerate probe available for either ligation of another degenerate probe or primer extension. These hybridization, ligation, and block removal steps are referred to herein as a round of degenerate probe ligation. Additional rounds of degenerate probe ligation can be performed following removal of the blocking structure. It is preferred that a set of primer extension sequencing assays be performed, using identical samples, in which a different number of rounds of degenerate probe ligation are performed prior to primer extension. It is also preferred that a nested set of interrogation probes be used in a set of such a set of primer extension sequencing assays. The use of such a set of assays is illustrated in Example 10. Once all the rounds of degenerate probe ligation are performed (thus forming an interrogation primer), the interrogation mixture is subjected to primer extension. For this, at least two differently labeled chain terminating nucleotides and DNA polymerase are added to the interrogation mixture. This results in addition of a single nucleotide to the end of the interrogation primers, the identity of which is based on the identity of the interrogated nucleotide (that is, the first template nucleotide after the end of the interrogation primer). Finally, the identity of the nucleotide incorporated for each interrogation primer for each target nucleic acid is determined by fluorescence microscopy. For this purpose, it is preferred that the nucleic acid be collapsed prior to detection of the incorporated nucleotide.

Example 10 describes an example of USA-CAGESEQ where a nested set of interrogation primers are extended by sequential addition of degenerate primers in an array of amplified nucleic acids. The principles of the primer extension sequencing operation illustrated in this example can be analogously applied to the use of different numbers of sample and interrogation probes, different arrangements of samples and different forms of blocking structures. It is contemplated that sets of assays can be performed on arrays of sample dots (as shown in Example 10), in arrays of samples (such as in microtiter dishes), or in individual reaction vessels. In particular, the use of a multiwell dish, such as a microtiter dish, allows multiple separate reactions on the same dish to be easily automated. The use of multiple wells also allows complete freedom in the selection of the sample and interrogation probe in each well. For example, rather than performing primer extension sequencing using five separately treated slides (as in example 10), primer extension sequencing samples and components could be arranged in any convenient order in the wells. Using the components of Example 10, for example, a five well by five well array of identical nucleic acid samples could be used where each of the wells in a given column has the same interrogation probe. The first column of wells would have the first interrogation probe, the second column of wells would have the second interrogation probe, and so on. As in example 10, the mask would be moved down to cover one additional row prior to each cage removal step. The resulting sequence obtained using this arrangement would be read across and then down.

As described above, specific portions of TS-DNA or TS-RNA can be sequenced using a primer extension sequencing operation. It should also be understood that the same primer extension sequencing procedure can be performed on any nucleic acid molecule. For example, genomic DNA, PCR products, viral RNA or DNA, and cDNA samples can all be sequenced using the disclosed primer extension sequencing procedure. A preferred primer extension sequencing procedure for this purpose is CAGE sequencing. For this purpose, interrogation probes and degenerate probes are hybridized to a nucleic acid sample of interest (rather than TS-DNA or TS-RNA), ligated, and subjected to chain-terminating primer extension, all as described above in connection with USA-CAGESEQ.

D. Discrimination Between Closely Related Target Sequences

Open circle probes, gap oligonucleotides, and gap spaces can be designed to discriminate closely related target sequences, such as genetic alleles. Where closely related target sequences differ at a single nucleotide, it is preferred that open circle probes be designed with the complement of this nucleotide occurring at one end of the open circle probe, or at one of the ends of the gap oligonucleotide(s). Where gap-filling ligation is used, it is preferred that the distinguishing nucleotide appear opposite the gap space. This allows incorporation of alternative (that is, allelic) sequence into the ligated OCP without the need for alternative gap oligonucleotides. Where gap-filling ligation is used with a gap oligonucleotide(s) that partially fills the gap, it is preferred that the distinguishing nucleotide appear opposite the portion of gap space not filled by a gap oligonucleotide. Ligation of gap oligonucleotides with a mismatch at either terminus is extremely unlikely because of the combined effects of hybrid instability and enzyme discrimination. When the TS-DNA is generated, it will carry a copy of the gap oligonucleotide sequence that led to a correct ligation. Gap oligonucleotides may give even greater discrimination between related target sequences in certain circumstances, such as those involving wobble base pairing of alleles. Features of open circle probes and gap oligonucleotides that increase the target-dependency of the ligation operation are generally analogous to such features developed for use with the ligation chain reaction. These features can be incorporated into open circle probes and gap oligonucleotides for use in LM-RCA. In particular, European Patent Application EP0439182 describes several features for enhancing target-dependency in LCR that can be adapted for use in LM-RCA. The use of stop bases in the gap space, as described in European Patent Application EP0439182, is a preferred mode of enhancing the target discrimination of a gap-filling ligation operation.

A preferred form of target sequence discrimination can be accomplished by employing two types of open circle probes. These two OCPs would be designed essentially as shown in FIG. 2, with small modifications. In one embodiment, a single gap oligonucleotide is used which is the same for both target sequences, that is, the gap oligonucleotide is complementary to both target sequences. In a preferred embodiment, a gap-filling ligation operation can be used (Example 3). Target sequence discrimination would occur by virtue of mutually exclusive ligation events, or extension-ligation events, for which only one of the two open-circle probes is competent. Preferably, the discriminator nucleotide would be located at the penultimate nucleotide from the 3' end of each of the open circle probes. The two open circle probes would also contain two different detection tags designed to bind alternative detection probes and/or address probes. Each of the two detection probes would have a different detection label. Both open circle probes would have the same primer complement portion. Thus, both ligated open circle probes can be amplified using a single primer. Upon array hybridization, each detection probe would produce a unique signal, for example, two alternative fluorescence colors, corresponding to the alternative target sequences.

E. Optimization of RCA

1. Assay Background

A potential source of background signals is the formation of circular molecules by non-target-directed ligation events. The contribution of such events to background signals can be minimized using five strategies, alone or in combination, as follows:

(a) The use of a thermostable DNA ligase such as AMP-LIGASE® (Kalin et al. (1992)) or the *T. thermophilus* DNA ligase (Barany (1991)) will minimize the frequency of non-target-directed ligation events because ligation takes place at high temperature (50 to 75° C.).

(b) In the case of in situ hybridization, ligation of the open circle probe to the target sequence permits extensive washing. This washing will remove any circles that may have been formed by non-target-directed ligation, while circles ligated on-target are impossible to remove because they are topologically trapped (Nilsson et al. (1994)).

(c) The use of one or more gap oligonucleotides, or a combination of gap oligonucleotides and gap-filling DNA synthesis, provides additional specificity in the ligation event. Using a gap oligonucleotide greatly reduces the probability of non-target-directed ligation. Particularly favored is the use of a gap oligonucleotide, or a gap-filling ligation operation, coupled to a capture hybridization step where the complementary portion of an address probe spans the ligation junction in a highly discriminatory fashion, as shown below and in FIG. 6.

complement of gap oligonucleotide (11 nucleotides)

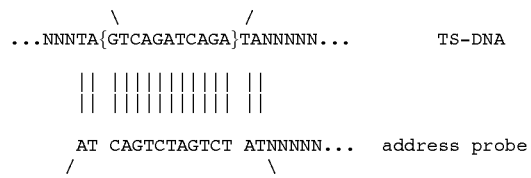

```
              \                    /
    ...NNNTA{GTCAGATCAGA}TANNNNN...        TS-DNA
           ||  |||||||||||  ||
           ||  |||||||||||  ||
            AT CAGTCAGATCAGA ATNNNNN...   address probe
           /                    \
``` complementary portion of address probe (15 nucleotides hybridized) Brackets ({ }) mark sequence complementary to the gap oligonucleotide (or the gap space when filled in). The TS-DNA shown is SEQ ID NO: 10 and the address probe sequence shown is SEQ ID NO:4. This system can be used with gap oligonucleotides of any length. Where the gap between the ends of an open circle probe hybridized to a target sequence is larger than the desired address probe length, an address probe can be designed to overlap just one of the junctions between the gap sequence and the open circle probe sequence. By designing open circle probes to place discriminating nucleotides opposite the gap space, a single OCP can be used in gap-filling LM-RCA to generate ligated open circle probes having different sequences, which depend on the target sequence.

The capture step involves hybridization of the amplified DNA to an address probe via a specific sequence interaction at the ligation junction, involving the complement of the gap oligonucleotide, as shown above. Guo et al. (1994), have shown that 15-mer oligonucleotides bound covalently on glass slides using suitable spacers, can be used to capture amplified DNA with reasonably high efficiency. This system can be adapted to detection of amplified nucleic acid (TS-DNA or TS-RNA) by using address probes to capture the amplified nucleic acid. In the example shown above, only LM-RCA amplified DNA generated from correct ligation events will be captured on the solid-state detector.

Optionally one may use additional immobilizing reagents, known in the art as capture probes (Syvanen et al., *Nucleic Acids Res.,* 14:5037 (1986)) in order to bind nucleic acids containing the target sequence to a solid surface. Suitable capture probes contain biotinylated oligonucleotides (Langer et al. (1981)) or terminal biotin groups. Immobilization may take place before or after the ligation reaction. Immobilization serves to allow removal of unligated open circle probes as well as non-specifically ligated circles.

(d) Using ligation conditions that favor intramolecular ligation. Conditions are easily found where circular ligation of OCPs occurs much more frequently than tandem linear ligation of two OCPs. For example, circular ligation is favored when the temperature at which the ligation operation is performed is near the melting temperature (Tm) of the least stable of the left target probe portion and the right target probe portion when hybridized to the target sequence. When ligation is carried out near the Tm of the target probe portion with the lowest Tm, the target probe portion is at association/dissociation equilibrium. At equilibrium, the probability of association in cis (that is, with the other target probe portion of the same OCP) is much higher than the probability of association in trans (that is, with a different OCP). When possible, it is preferred that the target probe portions be designed with melting temperatures near suitable temperatures for the ligation operation. The use of a thermostable ligase, however, allows a wide range of ligation temperatures to be used, allowing greater freedom in the selection of target sequences.

(e) Peptide nucleic acids form extremely stable hybrids with DNA, and have been used as specific blockers of PCR reactions (Orum et al., *Nucleic Acids Res.*, 21:5332–5336 (1993)). A special PNA probe, referred to herein as a PNA clamp, can be used to block rolling circle amplification of OCPs that have been ligated illegitimately (that is, ligated in the absence of target). By using one or more gap oligonucleotides during ligation, by using gap-filling ligation, or by using a combination of gap oligonucleotides and gap-filling ligation, illegitimately ligated circles will lack the gap sequence and they can be blocked with a PNA clamp that is complementary to the sequence resulting from the illegitimate ligation of the 3' end and the 5' end of the OCP. This is illustrated in the diagram below, where the PNA clamp llllrrrr is positioned exactly over the junction:

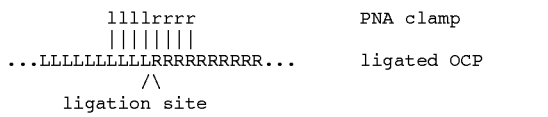

In this diagram, "L" and "l" represent a nucleotide in the left target probe portion of the OCP and its complement in the PNA clamp, and "R" and "r" represent a nucleotide in the right target probe portion of the OCP and its complement in the PNA clamp. The most preferred length for a PNA clamp is 8 to 10 nucleotides. The PNA clamp is incapable of hybridizing to unligated OCP because it can only form four to five base pairs with either target probe portion, and it is also incapable of hybridizing with correctly ligated OCP because a gap sequence is present. However, the PNA clamp will hybridize strongly with illegitimately ligated OCP, and it will block the progress of the rolling circle reaction because the DNA polymerase is incapable of displacing a hybridized PNA molecule. This prevents amplification of illegitimately ligated OCPs.

2. Removing Excess Unligated OCPs

The gene 6 exonuclease of phage T7 provides a useful tool for the elimination of excess open circle probes and excess gap oligonucleotides that will bind to the TS-DNA or LM-RCT transcripts and interfere with its hybridization to detection probes. This exonuclease digests DNA starting from the 5'-end of a double-stranded structure. It has been used successfully for the generation of single-stranded DNA after PCR amplification (Holloway et al., *Nucleic Acids Res.* 21:3905–3906 (1993); Nikiforov et al., *PCR Methods and Applications* 3:285–291(1994)). In an LM-RCA assay this enzyme can be added after ligation, together with the rolling circle DNA polymerase. To protect TS-DNA from degradation, the rolling circle replication primer can contain 3 or 4 phosphorothioate linkages at the 5' end, to make this molecule resistant to the exonuclease (Nikiforov et al. (1994)). The exonuclease will degrade excess open circle probe molecules as they become associated with the rolling circle DNA product. The use of this nuclease eliminates the need for capture probes as well as the need for washing to remove excess probes. In general, such a nuclease digestion should not be used when performing LM-RCT, since unligated OCPs and gap oligonucleotides are needed to form a double-stranded transcription template with the TS-DNA. This nuclease digestion is a preferred method of eliminating unligated OCPs and gap oligonucleotides when nested LM-RCA is to be performed.

EXAMPLES

Example 1

Target-mediated Ligation of Open Circle Probes and Rolling Circle Replication of Ligated Open Circle Probes 1. Ligation of Open Circle Probes Linear oligonucleotides with 5'-phosphates are efficiently ligated by ligase in the presence of a complementary target sequence. In particular, open circle probes hybridized to a target sequence as shown in FIG. 1, and open circle probes with gap oligonucleotides hybridized to a target sequence as shown in as shown in FIG. 2, are readily ligated. The efficiency of such ligation can be measured by LM-RCA.

The following is an example of target-dependent ligation of an open circle probe:

A DNA sample (target sample) is heat-denatured for 3 minutes at 95° C., and incubated under ligation conditions (45 minutes at 60° C.) in a buffer consisting of 20 mM Tris-HCl (pH 8.2), 25 mM KCl, 10 mM $MgCl_2$, 0.5 mM NAD, 0.05% Triton X-100, in the presence of (a) DNA ligase (AMPLIGASE®, Epicentre Technologies) at a concentration of 1 unit per 50 μl, and (b) the following 5'-phosphorylated oligonucleotides:

Open circle probe (111 nucleotides):

(SEQ ID NO:1)
5'-GCCTGTCCAGGGATCTGCTCAAGACTCGTCATGTCTCAGTAGCTT

CTAACGGTCACAAGCTTCTAACGGTCACAAGCTTCTAACGGTCACAT

GTCTGCTGCCCTCTGTATT-3'

Gap oligonucleotide: 5'-CCTT-3'

This results in hybridization of the open circle probe and gap oligonucleotide to the target sequence, if present in the target sample, and ligation of the hybridized open circle probe and gap oligonucleotide.

2. Measuring the Rate of Rolling Circle Replication (a) On Large Template: 7 kb Single-stranded Phage M13 Circle The rate of oligonucleotide-primed rolling circle replication on single-stranded M13 circles mediated by any DNA polymerase can be measured by using the assay described by Blanco et al., *J. Biol. Chem.* 264:8935–8940 (1989). The efficiency of primed synthesis by the Φ29 DNA polymerase is stimulated about 3-fold in the presence of Gene-32 protein, a single-stranded DNA binding protein.

(b) On Small Templates: 110-nucleotide Ligated Open Circle Probes

The rate of oligonucleotide-primed rolling circle replication on single-stranded small circles of 110 bases was measured using the Φ29 DNA polymerase generally as described in Example 2. After five minutes of incubation, the size of the DNA product is approximately 16 kilobases. This size corresponds to a polymerization rate of 53 nucleotides per second. The rate of synthesis with other DNA polymerases can be measured and optimized using a similar assay, as described by Fire and Xu, *Proc. Natl. Acad. Sci. USA* 92:4641–4645 (1995). It is preferred that single-stranded circles of 110 nucleotides be substituted for the 34 nucleotide circles of Fire and Xu.

The Φ29 DNA polymerase provides a rapid rate of polymerization of the Φ29 rolling circle reaction on 110 nucleotide circular templates. At the observed rate of 50 nucleotides per second, a 35 minute polymerization reaction will produce a DNA product of approximately 105,000 bases. This would yield an amplification of 954-fold over the original 110-base template. Fire and Xu (1995) shows that rolling circle reactions catalyzed by bacterial DNA polymerases may take place on very small circular templates of only 34 nucleotides. On the basis of the results of Fire and Yu, rolling circle replication can be carried out using circles of less than 90 nucleotides.

Example 2

Detection of a Mutant Ornithine Transcarbamylase (OTC) Gene Using LM-RCA Followed by Transcription (LM-RCT)

This example describes detection of human DNA containing a mutant form (G to C) at position 114 of exon 9 of the ornithine transcarbamylase gene (Hata et al., *J. Biochem.* 103:302–308 (1988)). Human DNA for the assay is prepared by extraction from buffy coat using a standard phenol procedure.
1. Two DNA samples (400 ng each) are heat-denatured for 4 minutes at 97° C., and incubated under ligation conditions in the presence of two 5'-phosphorylated oligonucleotides, an open circle probe and one gap oligonucleotide:

Open circle probe (95 nucleotides):

(SEQ ID NO:5)
5'-GAGGAGAATAAAAGTTTCTCATAAGACTCGTCATGTCTCAGCAGC

TTCTAACGGTCACTAATACGACTCACTATAGGTTCTGCCTCTGGGAA

CAC-3'

Gap oligonucleotide for mutant gene (8 nucleotides) 5'-TAGTGATG-3'

Gap oligonucleotide for wild type gene (8 nucleotides) 5'-TAGTGATC-3'

T4 DNA ligase (New England Biolabs) is present at a concentration of 5 units per μl, in a buffer consisting of 10 mM Tris-HCl (pH 7.5), 0.20 M NaCl, 10 mM MgCl$_2$, 2 mM ATP. The concentration of open circle probe is 80 nM, and the concentration of gap oligonucleotide is 100 nM. The total volume is 40 μl. Ligation is carried out for 25 minutes at 37° C.
2. 25 μl are taken from each of the above reactions and mixed with an equal volume of a buffer consisting of 50 mM Tris-HCl (pH 7.5), 10 mM MgCl$_2$, 1 mM DTT, 400 μM each of dTTP, dATP, dGTP, dCTP, which contains an 18-base rolling circle replication primer 5'-GCTGAGACATGACGAGTC-3' (SEQ ID NO:6), at a concentration of 0.2 μM. The Φ29 DNA polymerase (160 ng per 50 μl) is added and the reaction mixture is incubated for 30 minutes at 30° C.
3. To the above solutions a compensating buffer is added to achieve the following concentrations of reagents: 35 mM Tris-HCl (pH 8.2), 2 mM spermidine, 18 mM MgCl$_2$, 5 mM GMP, 1 mM of ATP, CTP, GTP, 333 μM UTP, 667 μM Biotin-16-UTP (Boehringher-Mannheim), 0.03% Tween-20, 2 Units per μl of T7 RNA polymerase. The reaction is incubated for 90 minutes at 37° C.
4. One-tenth volume of 5 M NaCl is added to the above reactions, and the resulting solution is mixed with an equal volume of ExpressHyb reagent (Clontech Laboratories, Palo Alto, Calif.). Hybridization is performed by contacting the amplified RNA solution, under a cover slip, with the surface of a glass slide (Guo et al. (1994)) containing a 2.5 mm dot with $2 \times 10^{11}$ molecules of a covalently bound 29-mer oligonucleotide with the sequence 5'-TTTTTTTTTTTCCAACCTCCATCACTAGT-3' (SEQ ID NO:7). The last 14 nucleotides of this sequence are complementary to the amplified mutant gene RNA, and hence the mutant RNA binds specifically. Another 2.5 mm dot on the slide surface contains $2 \times 10^{11}$ molecules of a covalently bound 29-mer oligonucleotide with the sequence 5'-TTTTTTTTTTTCCAACCTCGATCACTAGT-3' (SEQ ID NO:8). The last 14 nucleotides of this sequence are complementary to the amplified wild type gene RNA, and hence the wild type RNA binds specifically. The glass slide is washed once with 2× SSPE as described (Guo et al. (1994)), then washed twice with 2× SSC (0.36 M sodium saline citrate), and then incubated with fluoresceinated avidin (5 μg/ml) in 2× SSC for 20 minutes at 30° C. The slide is washed 3 times with 2× SSC and the slide-bound fluorescence is imaged at 530 nm using a Molecular Dynamics Fluorimager.

Example 3

Detection of a Mutant Ornithine Transcarbamylase (OTC) Gene Using Gap-Filling LM-RCT This example describes detection of human DNA containing a mutant form (G to C) at position 114 of exon 9 of the ornithine transcarbamylase gene (Hata et al. (1988)) using gap-filling LM-RCT. Human DNA for the assay is prepared by extraction from buffy coat using a standard phenol procedure. In this example, two different open circle probes are used to detect the mutant and wild type forms of the gene. No gap oligonucleotide is used.
1. Two DNA samples (400 ng each) are heat-denatured for 4 minutes at 97° C., and incubated in the presence of one of the following 5'-phosphorylated open circle probes.

Open circle probe for mutant gene (96 nucleotides):

(SEQ ID NO:11)
5'-TAAAAGACTTCATCATCCATCTCATAAGACTCGTCATGTCTCAGC

AGCTTCTAACGGTCACTAATACGACTCACTATAGGGGAACACTAGT

GATGG-3'.

When this probe hybridizes to the target sequence, there is a gap space of seven nucleotides between the ends of the open circle probe.

Open circle probe for wild type gene (96 nucleotides):

(SEQ ID NO:12)
5'-TAAAAGACTTCATCATCCATCTCATAAGACTCGTCATGTCTCAGC

AGCTTCTAACGGTCACTAATACGACTCACTATAGGGGAACACTAGT

GATCG-3'.

When this probe hybridizes to the target sequence, there is a gap space of seven nucleotides between the ends of the open circle probe. Each of the OCP-target sample mixtures are incubated in an extension-ligation mixture as described by Abravaya et al. (1995). The reaction, in a volume of 40 µl, contains 50 mM Tris-HCl (pH 7.8), 25 mM MgCl$_2$, 20 mM potassium acetate, 10 µM NAD, 80 µM open circle probe, 40 µM dATP, 40 µM dGTP, 1 Unit *Thermus flavus* DNA polymerase (lacking 3'-5' exonuclease activity; MBR, Milwaukee, Wis.), and 4000 Units *Thermus thermophilus* DNA ligase (Abbott laboratories). The reaction is incubated for 60 seconds at 85° C., and 50 seconds at 60° C. in a thermal cycler. No thermal cycling is performed. This results in hybridization of the open circle probe to the target sequence, if present, filling in of the gap space by the *T. flavus* DNA polymerase, and ligation by the *T. thermophilus* ligase. The discriminating nucleotide in the open circle probes above is the penultimate nucleotide. *T. flavus* DNA polymerase is used in the reaction to match the thermal stability of the *T. thermophilus* ligase.

2. 25 µl are taken from each of the above reactions and mixed with an equal volume of a buffer consisting of 50 mM Tris-HCl (pH 7.5), 10 mM MgCl$_2$, 1 mM DTT, 400 µM each of dTTP, dATP, dGTP, dCTP; and containing the 18-base oligonucleotide primer 5'-GCTGAGACATGACGAGTC-3' (SEQ ID NO:6), at a concentration of 0.2 µM. The Φ29 DNA polymerase (160 ng per 50 µl) is added and the reaction mixture is incubated for 30 minutes at 30° C. to perform rolling circle amplification catalyzed by Φ29 DNA polymerase. The *Thermus flavus* DNA polymerase does not significantly interfere with rolling circle replication because it has little activity at 30° C. If desired, the *Thermus flavus* DNA polymerase can be inactivated, prior to rolling circle replication, by adding a neutralizing antibody analogous to antibodies for blocking Taq DNA polymerase prior to PCR (Kellogg et al., *Biotechniques* 16(6):1134–1137 (1994)).

3. To each of the above solutions are added compensating buffer to achieve the following concentrations of reagents: 35 mM Tris-HCl (pH 8.2), 2 mM spermidine, 18 mM MgCl$_2$, 5 mM GMP, 1 mM of ATP, CTP, GTP, 333 µM UTP, 667 µM Biotin-16-UTP (Boehringher-Mannheim), 0.03% Tween-20, 2 Units per µl of T7 RNA polymerase. The reactions are incubated for 90 minutes at 37° C.

4. One-tenth volume of 5 M NaCl is added to the each solution containing the biotinylated RNA generated by T7 RNA polymerase, and the resulting solution is mixed with an equal volume of ExpressHyb reagent (Clontech laboratories, Palo Alto, Calif.). Hybridization is performed by contacting the amplified RNA solution, under a cover slip, with the surface of a glass slide (Guo et al. (1994)) containing a 2.5 mm dot with 2×10$^{11}$ molecules of a covalently bound 29-mer address probe with the sequence 5'-TTTTTTTTTTTCCAAATTCTCCTCCATCA-3' (SEQ ID NO: 13). The last 14 nucleotides of this sequence are complementary to the amplified mutant gene RNA, and hence the mutant RNA binds specifically. Another 2.5 mm dot on the slide surface contains 2×10$^{11}$ molecules of a covalently bound 29-mer address probe with the sequence 5'-TTTTTTTTTTTCCAAATTCTCCTCGATCA-3' (SEQ ID NO:14). The last 14 nucleotides of this sequence are complementary to the amplified wild type gene RNA, and hence the wild type RNA binds specifically. The glass slide is washed once with 2x SSPE as described (Guo et al. (1994)), then washed twice with 2x SSC (0.36 M sodium saline citrate), and then incubated with fluoresceinated avidin (5 µg/ml) in 2x SSC for 20 minutes at 30° C. The slide is washed 3 times with 2x SSC and the slide-bound fluorescence is imaged at 530 nm using a Molecular Dynamics Fluorimager.

Example 4

Reverse Transcription of Ornithine Transcarbamylase (OTC) mRNA Followed by Mutant cDNA Detection Using Gap-Filling LM-RCT This example describes detection of human mRNA containing a mutant form (G to C) at position 114 of exon 9 of the ornithine transcarbamylase gene (Hata et al. (1988)) using cDNA generated by reverse transcription. RNA for the assay is prepared by TRIzol (Life Technologies, Inc., Gaithersburg, Md.) extraction from liver biopsy.

1. OTC exon 9 cDNA is generated as follows:

A liver biopsy sample is stored at −80° C. in a 0.5 ml. reaction tube containing 40 Units of RNase inhibitor (Boehringher Mannheim). Total RNA is extracted from the frozen sample using TRIzol reagent (Life Technologies, Inc., Gaithersburg, Md.), and dissolved in 10 µl water. A 19 µl reaction mixture is prepared containing 4 µl of 25 mM MgCl$_2$, 2 µl of 400 mM KCl, 100 mM Tris-HCl (pH 8.3), 8 µl of a 2.5 mM mixture of dNTP's (dATP, dGTP, dTTP, dCTP), 1 µl of MuLV reverse transcriptase (50 U, Life Technologies, Inc., Gaithersburg, Md.), 1 µl of MuLV reverse transcriptase primer (5'-TGTCCACTTTCTGTTTTCTGCCTC-3'; SEQ ID NO:15), 2 µl of water, and 1 µl of RNase inhibitor (20 U). The reaction mixture is added to 1 µl of the Trizol-purified RNA solution, and incubated at 42° C. for 20 minutes to generate cDNA.

2. Two 20 µl cDNA samples from step 1 are heat-denatured for 4 minutes at 98° C., and incubated under ligation conditions in the presence of two 5'-phosphorylated probes:

Open circle probe (95 nucleotides):

(SEQ ID NO:16)
5'-ATCACTAGTGTTCCTTCTCATAAGACTCGTCATGTCTCAGCAGCTT

CTAACGGTCACTAATACGACTCACTATAGGGGATGATGAAGTCTTTT

AT-3'.

Gap probe for mutant gene (8 nucleotides): 5'-TAGTGATG-3'

Gap probe for wild type gene (8 nucleotides): 5'-TAGTGATC-3'

T4 DNA ligase (New England Biolabs) is added at a concentration of 5 units per µl, in a buffer consisting of 10 mM Tris-HCl (pH 7.5), 0.20 M NaCl, 10 mM MgCl$_2$, 2 mM ATP. The concentration of open circle probe is 80 nM, and the concentration of gap oligonucleotide is 100 nM. The total volume is 40 µliters. Ligation is carried out for 25 minutes at 37° C.

3. 25 µl are taken from each of the above reactions and mixed with an equal volume of a buffer consisting of 50 mM Tris-HCl (pH 7.5), 10 mM MgCl$_2$, 1 mM DTT, 200 µM each of dTTP, dATP, dGTP, dCTP; and containing the 18-base rolling circle replication primer 5'-GCTGAGACATGACGAGTC-3' (SEQ ID NO:6), at a concentration of 0.2 µM. The Φ29 DNA polymerase (160 ng per 50 µl) is added and the reaction mixtures are incubated for 30 minutes at 30° C.

4. To the above solutions are added compensating buffer to achieve the following concentrations of reagents: 35 mM Tris-HCl (pH 8.2), 2 mM spermidine, 18 mM MgCl$_2$, 5 mM GMP, 1 mM of ATP, CTP, GTP, 333 µM UTP, 667 µM Biotin-16-UTP (Boehringher-Mannheim), 0.03% Tween-20, 2 Units per µl of T7 RNA polymerase. The reaction is incubated for 90 minutes at 37° C.

5. One-tenth volume of 5 M NaCl is added to the each solution containing the biotinylated RNA generated by T7 RNA polymerase, and the resulting solution is mixed with an equal volume of ExpressHyb reagent (Clontech laboratories, Palo Alto, Calif.). Hybridization is performed by contacting the amplified RNA solution, under a cover slip, with the surface of a glass slide (Guo et al. (1994)) containing a 2.5 mm dot with 2×10¹¹ molecules of a covalently bound 29-mer address probe with the sequence 5'-TTTTTTTTTTTTTTTTGATGGAGGAGAAT-3' (SEQ ID NO: 17). The last 14 nucleotides of this sequence are complementary to the amplified mutant gene RNA, and hence the mutant RNA binds specifically. Another 2.5 mm dot on the slide surface contains 2×10¹¹ molecules of a covalently bound 29-mer address probe with the sequence 5'-TTTTTTTTTTTTTTTTGATCGAGGAGAAT-3' (SEQ ID NO:9). The last 14 nucleotides of this sequence are complementary to the amplified wild type gene RNA, and hence the wild type RNA binds specifically. The glass slide is washed once with 2× SSPE as described (Guo et al. (1994)), then washed twice with 2× SSC (0.36 M sodium saline citrate), and then incubated with fluoresceinated avidin (5 µg/ml) in 2× SSC for 20 minutes at 30° C. The slide is washed 3 times with 2× SSC and the slide-bound fluorescence is imaged at 530 nm using a Molecular Dynamics Fluorimager.

Example 5

Multiplex Immunoassay Coupled to Rolling Circle Amplification

This example describes an example of multiplex detection of different target molecules using reporter antibodies. The signal that is detected is produced by rolling circle amplification of the target sequence portion of the reporter antibodies.

1. Three different monoclonal antibodies, each specific for a different target molecule, are coupled to three different arbitrary DNA sequences (A, B, C) that serve as unique identification tags (target sequences). In this example, the three antibodies are maleimide-modified and are specific for β-galactosidase, hTSH, and human chorionic gonadotropin (hCG). The antibodies are coupled to aminated DNA oligonucleotides, each oligonucleotide being 50 nucleotides long, using SATA chemistry as described by Hendrickson et al. (1995). The resulting reporter antibodies are called reporter antibody A, B, and C, respectively.

2. Antibodies specific for the target molecules (not the reporter antibodies) are immobilized on microtiter dishes as follows: A 50 µl mixture containing 6 µg/ml of each of the three antibodies in sodium bicarbonate (pH 9) is applied to the wells of a microtiter dish, incubated overnight, and washed with PBS-BLA (10 mM sodium phosphate (pH 7.4), 150 mM sodium chloride, 2% BSA, 10% β-lactose, 0.02% sodium azide) to block non-adsorbed sites.

3. Serial dilutions of solutions containing one or a combination of the three target molecules (hTSH, hCG, and β-galactosidase) are added to the wells. Some wells are exposed to one target molecule, a mixture of two target molecules, or a mixture of all three target molecules. After 1 hour of incubation, the wells are washed three times with TBS/Tween wash buffer as described by Hendrickson et al. (1995).

4. Fifty microliters of an appropriately diluted mixture of the three reporter antibodies (A+B+C) are added to each well of the microtiter dish. The plate is incubated at 37° C. for 1 hour, and then washed four times with TBS/Tween buffer.

5. To each well is added a mixture of three pairs of open circle probes and gap oligonucleotides, each pair specific for one of the three target sequence portions of the reporter antibodies. In this example, the open circle probes have the same spacer region of 49 bases including a universal primer complement portion, and different 18 nucleotide target probe portions at each end. Each cognate pair of open circle probe and gap oligonucleotide is designed to hybridize to a specific target sequence (A, B, or C) in the target sequence portion of the reporter antibodies. Specifically, Open circle probe A' has left and right target probe portions complementary to two 18-base sequences in tag sequence A separated by 8 bases that are complementary to the 8-nucleotide gap oligonucleotide A'. The same is the case for open circle probe and gap oligonucleotide pairs B' and C'. The concentration of each open circle probe is 80 nM, and the concentration of each gap oligonucleotide is 120 nM.

6. T4 DNA ligase (New England Biolabs) is added to each microtiter well at a concentration of 5 units per µl, in a reaction buffer consisting (10 mM Tris-HCl (pH 7.5), 40 mM potassium acetate, 10 mM MgCl₂, 2 mM ATP). The total volume in each well is 40 µliters. Ligation is carried out for 45 minutes at 37° C.

7. To each microtiter well is added 20 µl of a compensating solution containing dTTP, dATP, dGTP, dCTP (400 µM each), the universal 18-base oligonucleotide primer 5'-GCTGAGACATGACGAGTC-3' (SEQ ID NO:6) (at a final concentration of 0.2 µM), and Φ29 DNA polymerase (at 160 ng per 50 µl). The reaction for 30 minutes at 30° C.

8. After incubation, a compensating buffer is added to each well to achieve the following concentrations of reagents: 35 mM Tris-HCl (pH 8.2), 2 mM spermidine, 18 mM MgCl₂, 5 mM GMP, 1 mM of ATP, CTP, GTP, 333 µM UTP, 667 µM Biotin-16-UTP (Boehringher-Mannheim), 0.03% Tween-20, 2 Units per µl of T7 RNA polymerase. The reaction is incubated for 90 minutes at 37° C., generating biotinylated RNA.

9. One-tenth volume of 5 M NaCl is added to each well, and the resulting solution is mixed with and equal volume of ExpressHyb reagent (Clontech laboratories, Palo Alto, Calif.). Hybridization is performed by contacting the mixture of amplified RNAs, under a cover slip, with the surface of a glass slide containing three separate dots of 2×10¹¹ molecules of three different covalently bound 31-mer oligonucleotides (A, B, C) (Guo et al. (1994)). The last 16 bases of each oligonucleotide are complementary to a specific segment (4 bases+8 bases+4 bases), centered on the 8-base gap sequence, of each of the possible amplified RNAs generated from tag sequences A, B, or C. Hybridization is carried out for 90 minutes at 37° C. The glass slide is washed once with 2× SSPE as described (Guo et al. (1994)), then washed twice with 2× SSC (0.36 M sodium saline citrate), and then incubated with fluoresceinated avidin (5 µg/ml) in 2× SSC for 20 minutes at 30° C. The slide is washed 3 times with 2× SSC and the surface-bound fluorescence is imaged at 530 nm using a Molecular Dynamics Fluorimager to determine if any of tag sequences A or B or C was amplified.

Example 6

In situ Detection of Ornithine Transcarbamylase (OTC) and Cystic Fibrosis (CF) Target Sequences Using LM-RCA 1. DNA samples were prepared as follows:
A sample of lymphocytes was washed twice in PBS, with the cells collected by centrifugation for 5 minutes at 1500 RPM. The cells were resuspended in 10 mM PIPES, pH 7.6, 100 mM NaCl, 0.3 M sucrose, 3 mM MgCl₂, and 0.5% Triton X-100. The cells were then incubated on ice for 15 minutes, centrifuged for 5 minutes at 1700 RPM, and resuspend at 2×10⁵ nuclei/ml. Samples of 1.0×10⁵ nuclei (0.5 ml) were centrifuged onto slides (5 minutes at 500 g, setting #85) in Cytospin centrifuge. The slides were then rinsed twice for 3 minutes with PBS, rinsed once for 6 minutes with agitation in 2 M NaCl, 10 mM PIPES, pH 6.8, 10 mM EDTA, 0.5% Triton X-100, 0.05 mM Spermine, and 0.125 mM Spermidine. The slides were then rinsed for one minute in 10× PBS, for one minute in 5× PBS, for one minute in 2× PBS, for 2 minutes in 1× PBS, for one minute in 10% ethanol, for one minute in 30% ethanol, for one minute in 70% ethanol, and for one minute in 95% ethanol. Finally, the slides were air dried and then fixed by baking at 70° C. for 2 hours.

2. The following DNA molecules were used:

OTC Open Circle Probe (OTC OCP, for OTC target sequence):

5'-GAGGAGAATAAAAGTTTCTCATAAGACTCGTCATGTCTCAG

CAGCTTCTAACGGTCACTAATACGACTCACTATAGGTTCTGCCT

CTGGGAACAC-3'

OTC Gap oligonucleotide: 5'-TAGTGATC-3'

Cystic fibrosis Open Circle Probe (CF OCP, for CF target sequence):

5'-TATTTTCTTTAATGGTTTCTCTGACTCGTCATGTCTCAGC

TTTAGTTTAATACGACTCACTATAGGATCTATATTCATCAT

AGGAAACAC-3'

Cystic fibrosis Gap oligonucleotide 5'-CAAAGATGA-3'

3. DNA on the sample slides was denatured by washing the slides for 5 minutes in 2× SSC, incubating in denaturation buffer (2× SSC, 70% formamide, pH 7.2) for 1 minute and 45 seconds in a pre-heated large Coplin jar at 71° C. Heating was stopped immediately by washing the slides for three minutes in ice-cold 70% ethanol, for two minutes in 90% ethanol, and for three minutes in 100% ethanol.

4. LM-RCA was performed as follows:

In three separate reactions, the OCPs and gap oligonucleotides were hybridized and ligated to target sequences on the sample slides.

a. OTC and CF ligation operation: 42 μl of the mixture below was placed on each of two slides.

| 9 μl | 10X ligation buffer (Ampligase) | |
|---|---|---|
| 5 μl | BSA, 2 mg/ml stock | |
| 9 μl | OTC Gap oligo (15 μM) | [final 1500 nM] |
| 9 μl | CF Gap oligo (10 μM) | [final 1000 nM] |
| 3 μl | OTC OCP, (6 μM stock) | [final = 200 nMolar] |
| 3 μl | CF OCP, (6 μM stock) | [final = 200 nMolar] |
| 15 μl | Ampligase (5 U/μl) | [final = 0.833 U/μl] |
| 38 μl | H₂O | |

The reaction was incubated for 120 minutes at 50° C.

b. OTC ligation operation: 42 μl of the mixture below was placed on a slide.

| 6 μl | 10X ligation buffer (Ampligase) | |
|---|---|---|
| 3.5 μl | BSA, 2 mg/ml stock | |
| 6 μl | OTC Gap oligo (15 μM) | [final 1500 nM] |
| 2 μl | OTC OCP, (6 μM stock) | [final = 200 nMolar] |
| 10 μl | Ampligase (5 U/μl) | [final = 0.833 U/μl] |
| 33 μl | H₂O | |

The reaction was incubated for 120 minutes at 50° C.

c. CF ligation operation: 42 μl of the mixture below was placed on a slide.

| 6 μl | 10X ligation buffer (Ampligase) | |
|---|---|---|
| 3.5 μl | BSA, 2 mg/ml stock | |
| 6 μl | CF Gap oligo (10 μM) | [final 1000 nM] |
| 2 μl | CF OCP, (6 μM stock) | [final = 200 nMolar] |
| 10 μl | Ampligase (5 U/μl) | [final = 0.833 U/μl] |
| 33 μl | H₂O | |

The reaction was incubated for 120 minutes at 50° C.

All of the slides were washed twice for 5 minutes with 2× SSC with 20% formamide at 42° C., washed for two minutes with 20 mM Tris, pH 7.5, 0.075 M NaCl to remove the formamide, and washed for three minutes with 50 mM Tris, pH 7.5, 40 mM KOAc, 10 mM MgCl₂, 10 mM DTT, 100 μg/ml BSA.

The amplification operation was performed by placing 24 μl of the following mixture on each slide.

| 18.0 μl | H₂O [total volume = 100 μl for 4 slides] |
|---|---|
| 20.0 μl | 5X φ29 buffer with BSA BSA is 200 μg/ml |
| 16.0 μl | dNTPs (A, G, and C, each 2.5 mM) |
| 5.0 μl | dTTP (2.5 mM) |
| 15.0 μl | BUdR (2.5 mM) |
| 7.0 μl | rolling circle replication primer (10 μM) |
| 3.0 μl | Gene32 Protein (1.37 μg/μl) (final 41 μg/ml) |
| 16.0 μl | φ29 DNA polymerase (1:6 dilution, 16 μl = 768 ng) |

The reaction was incubated 20 minutes in 37° C. oven.

All slides were then washed twice for four minutes with 2× SSC with 20% formamide at 25° C., and then washed twice for four minutes with 2× SSC, 3% BSA, 0.1% Tween-20 at 37° C.

5. The TS-DNA generated in the amplification operation was collapsed and detected as follows:

50 μl of a solution of AntiBUDR-Mouse.IgG (7 μg/ml) in 2× SSC, 3% BSA, 0.1% Tween-20 was placed on each slide, and the slides were incubated for 30 minutes at 37° C. Then the slides were washed three times for five minutes with 2× SSC, 3% BSA, 0.1% Tween-20 at 37° C. Next, 50 μl of a solution of FITC-Avidin (6 μg/ml) was placed on each slide, and the slides were incubated for 30 minutes at 37° C. Then the slides were washed three times for five minutes with 2× SSC, 3% BSA, 0.1% Tween-20 at 37° C., and then incubated for 2.6 minutes with 2× SSC, 0.1 μg/ml DAPI (26 μl in 50 ml) at room temp. Next, the slides were washed 10 minutes with 1× SSC, 0.01% Tween at room temperature and then covered with 24 μl antifade. Finally, the slides were examined in a microscope with CCD camera for DAPI nuclear fluorescence and discrete fluorescein signals.

Example 7

Multiplex Detection of Multiple Target Sequences Using LM-RCA-CMC

This example illustrates multiplex detection using 31 different OCPs and gap oligonucleotide pairs, each designed to generate 31 different color combinations using 5 basic colors.

1. Slides containing samples are prepared as follows:

Poly-L-Lysine coated microscope slides are prepared, and DNA is spotted using an arraying machine as described above using the method described by Schena et al. The size of each spot of sample DNA is 2.5 mm. DNA is denatured as described above using the method described by Schena et al.

2. A mixture of gap oligonucleotides and open circle probes is designed and prepared, containing 31 different OCPs and 31 different gap oligonucleotides. The OCPs and gap oligonucleotides are designed as pairs with each OCP and gap probe pair containing sequences complementary to a specific target sequence of interest. The spacer regions of each of the 31 OCPs contain unique, alternative combinations of five possible detection tags, designated 1t, 2t, 3t, 4t, and 5t. The combinations are coded according to the scheme shown below. The set of pairs is designated as follows:

| Gap oligo | OCP | 1t | 2t | 3t | 4t | 5t |
|---|---|---|---|---|---|---|
| g1 | ocp1 | + | | | | |
| g2 | ocp2 | | + | | | |
| g3 | ocp3 | | | + | | |
| g4 | ocp4 | | | | + | |
| g5 | ocp5 | | | | | + |
| g6 | ocp6 | + | + | | | |
| ... | | | | | | |
| ... and so on | | | | | | |
| ... | | | | | | |
| g25 | ocp25 | | | + | + | + |
| g26 | ocp26 | + | + | + | + | |
| g27 | ocp27 | + | + | + | | + |
| g28 | ocp28 | + | + | | + | + |
| g29 | ocp29 | + | | + | + | + |
| g30 | ocp30 | | + | + | + | + |
| g31 | ocp31 | + | + | + | + | + |

3. LM-RCA is performed as follows:

The OCPs and gap oligonucleotides are hybridized and ligated to target sequences on the sample slides with 50 µl of the following mixture.

| | |
|---|---|
| 1.5 µl | 10X ligation buffer (Ampligase) |
| 8.8 µl | BSA, 2 mg/ml stock |
| 15 µl | Mixture of 31 Gap oligonucleotides [final 400 nM for each] |
| 5 µl | Mixture of 31 OCPs [final = 100 nMolar for each] |
| 25 µl | Ampligase (5 U/µl) |
| 82 µl | H₂O |

The reaction is incubated for 60 minutes at 52° C.

The slides are washed twice for 5 minutes with 2× SSC with 20% formamide at 42° C., washed for two minutes with 20 mM Tris, pH 7.5, 0.075 M NaCl to remove the formamide, and washed for three minutes with 50 mM Tris, pH 7.5, 40 mM KOAc, 10 mM MgCl₂, 10 mM DTT, 100 µg/ml BSA.

The amplification operation is performed by placing 24 µl of the following mixture on each slide.

| | |
|---|---|
| 18.0 µl | H₂O [total volume =[100 µl for 4 slides] |
| 20.0 µl | 5X φ29 buffer with BSA BSA is 200 µg/ml |
| 16.0 µl | dNTPs (A, G, and C, each 2.5 mM) |
| 5.0 µl | dTTP (2.5 mM) |
| 15.0 µl | BUdR (2.5 mM) |
| 7.0 µl | rolling circle replication primer (10 µM) |
| 3.0 µl | Gene32 Protein (1.37 µg/µl) (final 41 µg/ml) |
| 16.0 µl | φ29 DNA polymerase (1:6 dilution, 16 µl = 768 ng) |

The reaction is incubated 15 minutes in 37° C. oven.

All slides were then washed twice for four minutes with 2× SSC with 20% formamide at 25° C.

4. The 5 collapsing detection probes, each with a different label and each complementary to one of the 5 detection tags, are hybridized to the TS-DNA on the slides in a solution of 4× SSC. The detection probes correspond to the detection tags as follows:

| Detection probe | Label | Detection tag |
|---|---|---|
| dp1 | fluorescein | 1t |
| dp2 | Cy3 | 2t |
| dp3 | Cy3.5 | 3t |
| dp4 | Cy5 | 4t |
| dp5 | Cy7 | 5t |

All slides were then washed twice for four minutes with 2× SSC with 20% formamide at 25° C., and then washed twice for four minutes with 2× SSC, 3% BSA, 0.1% Tween-20 at 37° C.

5. The TS-DNA generated in the amplification operation is further collapsed and detected as follows:

50 µl of a solution of AntiBUDR-Mouse.IgG (7 µg/ml) in 2× SSC, 3% BSA, 0.1% Tween-20 is placed on each slide, and the slides are incubated for 30 minutes at 37° C. Then the slides are washed three times for five minutes with 2× SSC, 3% BSA, 0.1% Tween-20 at 37° C. Next, 50 µl of a solution of Avidin DN (6 µg/ml) in 2× SSC, 3% BSA, 0.1% Tween-20 is placed on each slide, and the slides are incubated for 30 minutes at 37° C. Then the slides are washed three times for five minutes with 2× SSC, 3% BSA, 0.1% Tween-20 at 37° C., washed 5 minutes with 2× SSC, 0.01% Tween at room temperature, and then covered with 24 µl antifade. Finally, the slides are scanned in a fluorescence scanning device with appropriate filters (for example, those described by Schena et al.). Image analysis software is used to count and analyze the spectral signatures of the fluorescent dots.

Example 8

Multiplex Detection of Multiple Target Sequences Using LM-RCA-CMC

This example illustrates multiplex detection using 15 different OCPs and 30 different gap oligonucleotides, where pairs of gap oligonucleotides are associated with each OCP. The OCPs and gap oligonucleotides are designed to generate 30 different color combinations using 6 basic label colors.

1. Slides containing samples are prepared as follows:

Poly-L-Lysine coated microscope slides are prepared, and DNA is spotted using an arraying machine as described above using the method described by Schena et al. The size of each spot of sample DNA is 2.5 mm. DNA is denatured as described above using the method described by Schena et al.

2. A mixture of gap oligonucleotides and open circle probes is designed and prepared, containing 15 different OCPs and 30 different gap oligonucleotides. The OCPs and gap oligonucleotides are designed as pairs with each OCP and gap probe pair containing sequences complementary to a specific target sequence of interest. The spacer regions of each of the 15 OCPs contain unique, alternative combinations of four possible detection tags, designated 1t, 2t, 3t, and 4t. Additional detection tags are generated by ligation of an OCP to a gap oligonucleotide. These form two different detection tags depending on which of the pair of gap oligonucleotides is ligated to a given OCP. The combinations are coded according to the scheme shown below. The set of pairs is designated as follows:

| Gap oligo | OCP | 1t | 2t | 3t | 4t |
|---|---|---|---|---|---|
| g1 | ocp 1 | + | | | |
| g2 | ocp 1 | + | | | |
| g3 | ocp 2 | | + | | |
| g4 | ocp 2 | | + | | |
| g5 | ocp 3 | | | + | |
| g6 | ocp 3 | | | + | |
| ... and so on ... | | | | | |
| g25 | ocp 13 | + | | + | + |
| g26 | ocp 13 | + | | + | + |
| g27 | ocp 14 | | + | + | + |
| g28 | ocp 14 | | + | + | + |
| g29 | ocp 15 | + | + | + | + |
| g30 | ocp 15 | + | + | + | + |

3. LM-RCA is performed as follows:

The OCPs and gap oligonucleotides are hybridized and ligated to target sequences on the sample slides with 50 µl of the following mixture.

| | |
|---|---|
| 1.5 µl | 10X ligation buffer (Ampligase) |
| 8.8 µl | BSA, 2 mg/ml stock |
| 15 µl | Mixture of 30 Gap oligonuckotides [final 400 nM for each] |
| 5 µl | Mixture of 15 OCPs [final = 100 nMolar for each] |
| 25 µl | Ampligase (5 U/µl) |
| 82 µl | H$_2$O |

The reaction is incubated for 60 minutes at 52° C.

The slides are washed twice for 5 minutes with 2× SSC with 20% formamide at 42° C., washed for two minutes with 20 mM Tris, pH 7.5, 0.075 M NaCl to remove the formamide, and washed for three minutes with 50 mM Tris, pH 7.5, 40 mM KOAc, 10 mM MgCl$_2$, 10 mM DTT, 100 µg/ml BSA.

The amplification operation is performed by placing 24 µl of the following mixture on each slide.

| | |
|---|---|
| 18.0 µl | H$_2$O [total volume = 100 µl for 4 slides] |
| 20.0 µl | 5X φ29 buffer with BSA BSA is 200 µg/ml |
| 16.0 µl | dNTPs (A, G, and C, each 2.5 mM) |
| 5.0 µl | dTTP (2.5 mM) |
| 15.0 µl | BUdR (2.5 mM) |
| 7.0 µl | rolling circle replication primer (10 µM) |
| 3.0 µl | Gene32 Protein (1.37 µg/µl) (final 41 µg/ml) |
| 16.0 µl | φ29 DNA polymerase (1:6 dilution, 16 µl = 768 ng) |

The reaction is incubated 15 minutes in 37° C. oven.

All slides were then washed twice for four minutes with 2× SSC with 20% formamide at 25° C.

4. Four collapsing detection probes, each with a different label and each complementary to one of the 4 detection tags, 1t, 2t, 3t, and 4t, along with collapsing detection probes, each with one of two labels and each complementary to one of the detection tags formed by the ligation of an OCP and gap oligonucleotide, are hybridized to the TS-DNA on the slides in a solution of 4× SSC. The detection probes correspond to the detection tags as follows:

| Detection probe | Label | Detection tag |
|---|---|---|
| dp1 | fluorescein | 1t |
| dp2 | Cy3 | 2t |
| dp3 | Cy3.5 | 3t |
| dp4 | Cy5.5 | 4t |
| dp5 | Cy5 | g1 |
| dp6 | Cy7 | g2 |
| dp7 | Cy5 | g3 |
| dp8 | Cy7 | g4 |
| dp9 | Cy5 | g5 |
| dp10 | Cy7 | g6 |
| dp11 | Cy5 | g7 |
| dp12 | Cy7 | g8 |
| dp13 | Cy5 | g9 |
| dp14 | Cy7 | g10 |
| dp15 | Cy5 | g11 |
| dp16 | Cy7 | g12 |
| dp17 | Cy5 | g13 |
| dp18 | Cy7 | g14 |
| dp19 | Cy5 | g15 |
| dp20 | Cy7 | g16 |
| dp21 | Cy5 | g17 |
| dp22 | Cy7 | g18 |
| dp23 | Cy5 | g19 |
| dp24 | Cy7 | g20 |
| dp25 | Cy5 | g21 |
| dp26 | Cy7 | g22 |
| dp27 | Cy5 | g23 |
| dp28 | Cy7 | g24 |
| dp29 | Cy5 | g25 |
| dp30 | Cy7 | g26 |
| dp31 | Cy5 | g27 |
| dp32 | Cy7 | g28 |
| dp33 | Cy5 | g29 |
| dp34 | Cy7 | g30 |

All slides were then washed twice for four minutes with 2× SSC with 20% formamide at 25° C., and then washed twice for four minutes with 2× SSC, 3% BSA, 0.1% Tween-20 at 37° C.

5. The TS-DNA generated in the amplification operation is further collapsed and detected as follows:

50 µl of a solution of AntiBUDR-Mouse.IgG (7 µg/ml) in 2× SSC, 3% BSA, 0.1% Tween-20 is placed on each slide, and the slides are incubated for 30 minutes at 37° C. Then the slides are washed three times for five minutes with 2× SSC, 3% BSA, 0.1% Tween-20 at 37° C. Next, 50 µl of a solution of Avidin DN (6 µg/ml) in 2× SSC, 3% BSA, 0.1% Tween-20 is placed on each slide, and the slides are incubated for 30 minutes at 37° C. Then the slides are washed three times for five minutes with 2× SSC, 3% BSA, 0.1% Tween-20 at 37° C., washed 5 minutes with 2× SSC, 0.01% Tween at room temperature, and then covered with 24 µl antifade. Finally, the slides are scanned in a fluorescence scanning device with appropriate filters (for example, those described by Schena et al.). Image analysis software is used to count and analyze the spectral signatures of the fluorescent dots.

Example 9

Unimolecular Segment Amplification and Sequencing

This example illustrates unimolecular segment amplification (that is, rolling circle amplification) followed by single nucleotide primer extension sequencing. In this example, an OCP is hybridized to a target nucleic acid so as to leave a gap in a region of known sequence variation. After formation of an amplification target circle using gap-filling ligation, and rolling circle amplification of the amplification target circle, the amplified DNA is subjected to chain terminating primer extension sequencing using uniquely labeled chain-terminating nucleotides. Detection of the incorporated label identifies the nucleotide of interest.

An Open Circle Probe designed to hybridize with the Cystic Fibrosis Transmembrane Regulator G542X mutant locus is designed so as to leave a gap of four bases, encompassing the mutant base. The gap is to be filled by a DNA polymerase in a gap-filling ligation operation, thereby incorporating whatever sequence is present in the target Cystic Fibrosis Transmembrane Regulator G542X.

The sequence of the 5'-phosphorylated OCP (82 bases) is as follows:

```
                    (nucleotides 1 to 82 of SEQ ID NO:20)
GAACTATATTGTCTTTCTCTGTTTTCTTGCATGGTCACACGTCGTTCT

AGTACGCTTCTAACTTAGTGTGATTCCACCTTCT
```

The underlined ends of this probe hybridize with the target human DNA as indicated below (target sequence shown in reverse, 3' to 5'):

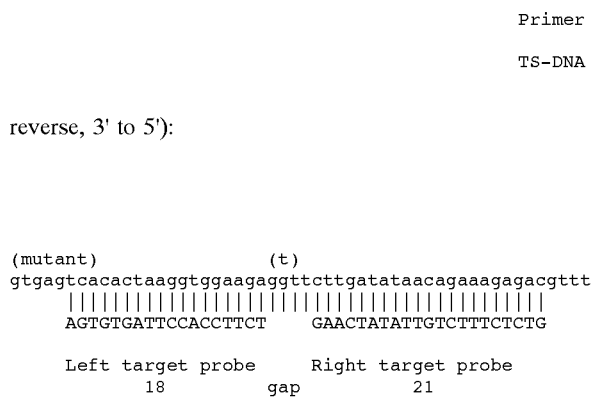

The target DNA is SEQ ID NO:21. The left target probe is nucleotides 65 to 82 of SEQ ID NO:20. The right target probe is nucleotides 1 to 21 of SEQ ID NO:20. The region in the target DNA opposite the gap encompasses a nucleotide which is either g (wild type) or t (mutant). It is this nucleotide position which is interrogated (that is, sequenced).

1. Microscope slides containing bound DNA samples are prepared as described by Schena et al.
2. Gap-filling ligation in the presence of 150 nMolar Open Circle Probe, Ampligase DNA ligase, and *Thermus flavus* DNA polymerase is carried out as described earlier (generally using the conditions described by Abravaya et al., *Nucleic Acids Research* 23:675–682 (1995)), in the presence of dATP and dCTP, so that the gap is filled and immediately ligated. The reaction is carried out with the slides covered with a 22 by 40 mm cover slip, in a volume of 28 μl, and is incubated for 1 hour at 58° C. The filling reaction adds the base sequence CCAA for the wild type, or the sequence CAAA for the mutant gene, respectively.
3. Wash slides twice in 2× SSC with 20% formamide for 5 minutes at 42° C.

4. Wash slides for 2 minutes with 20 mM Tris, pH 7.5, 0.075 M NaCl.
5. Rolling Circle Amplification is carried out in situ for 15 minutes at 30° C. in a buffer containing the following components: 50 mM Tris-HCl, pH 7.5, 10 mM MgCl$_2$, 1 mM DTT, 400 μM each of dCTP, dATP, and dGTP, 95 μM dTTP, 380 μM BUDR triphosphate (SIGMA), the 18 nucleotide rolling circle replication primer, ACGACGTGTGAC-CATGCA (SEQ ID NO:22), at a concentration of 0.7 μM, Phage T4 Gene-32 protein at a concentration of 1000 nMolar, and Φ29 DNA polymerase at 200 nM. This reaction generates approximately 400 copies of TS-DNA containing faithful copies of the gene sequence.
6. Wash twice in 2× SSC with 20% formamide for 5 minutes at 25° C.
7. Incubate the slides with the 20 nucleotide interrogation primer, TAGTGTGATTCCACCTTCTC (nucleotides 64 to 83 of SEQ ID NO:20), designed to hybridize with the TS-DNA adjacent to the nucleotide being interrogated, shown below as a boldface N:

```
Primer      TAGTGTGATTCCACCTTCTC
            ||||||||||||||||||||
TS-DNA   . . .gaagattgaatcacactaaggtggaagagNttcttgata. . .
```

The TS-DNA is SEQ ID NO:22. The slides are incubated 10 minutes at 37° C. in the following conditions:

Four Units Sequenase DNA polymerase (Amersham-USB), in 25 μl of 50 mM Tris-HCl, pH 7.5, 20 mM MgCl$_2$, 50 mM NaCl, 5 mM DTT, 50 μg/ml Bovine Serum Albumin (Molecular Biology grade from Life Sciences, Inc.), 50 μM fluorescent-ddATP, fluorescent-ddCTP, fluorescent-ddGTP, and fluorescent-ddTTP. The four fluorescent dideoxynucleoside triphosphates each have different emission spectra and can be obtained from a standard DNA sequencing kit (Applied Biosystems, Inc.).

Sequenase DNA polymerase incorporates only one ddNTP, where the incorporated ddNTP is complementary to the nucleotide being interrogated. This is illustrated below where when the interrogated nucleotide is a T (the mutant form), fluorescent ddATP is incorporated:

```
TS-DNA . . .gaagattgaatcacactaaggtggaagagTttcttgata. . .
```

The extended primer is nucleotides 64 to 84 of SEQ ID NO:20. If the interrogated nucleotide is G (the wild type), fluorescent ddCTP is incorporated.
8. Wash for 5 minutes in 2× SSC at 25° C.
9. Wash for 4 minutes in 2× SSC, 2.8% BSA, 0.12% Tween-20 at 37° C.
10. Incubate 30 minutes at 37° C. in 50 μl (under cover slip) using 5 μg/ml Biotinylated AntiBUDR-Mouse.IgG (Zymed Labs) in 2× SSC, 2.8% BSA, and 0.12% Tween-20.

11. Wash three times in 2× SSC, 2.8% BSA, and 0.12% Tween-20 for 5 minutes at 37° C.
12. Incubate 30 minutes at 37° C. in 50 μl (under cover slip) using FITC-Avidin, 5 μg/ml, in 2× SSC, 2.8% BSA, and 0.12% Tween-20.
13. Wash three times in 2× SSC, 2.8% BSA, and 0.12% Tween-20 for 5 minutes at 37° C.
14. Wash 5 minutes with 2× SSC, and 0.01% Tween-20 at room temperature.
15. An image of the slide is captured using a microscope-CCD camera system with appropriate filter sets. Each TS-DNA, each with multiple extended primers, occupy a small area on the slides. The incorporated fluorescent nucleotides produce individual fluorescent dots for each TS-DNA. The fluorescent emission color defines the nucleotide incorporated at the specific extension position in each fluorescent dot. Thus, in a sample containing a mixture of wild type and mutant sequences, the presence of each is indicated by the presence of fluorescent dots having the fluorescent emission color of the fluorescent ddATP (indicating the mutant form) and of fluorescent dots having the fluorescent emission color of the fluorescent ddCTP (indicating the wild type). The dots will be distinct and distinguishable due to the small area occupied by each TS-DNA due to its collapse.

Figure 16C:
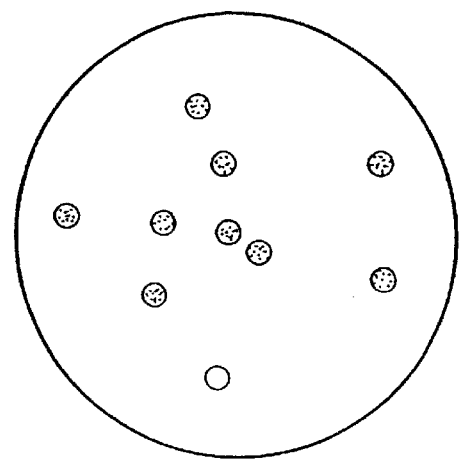
FIGS. 16A, 16B, and 16C are diagrams showing the results of unimolecular segment amplification and sequencing (USA-SEQ) performed on three different nucleic acid samples. The large circles represent a target sample dot on a solid-state support. The small circles represent individual TS-DNA molecules, amplified in situ at the location of target nucleic acids in the sample, which have been subjected to primer extension sequencing.
Figure 16A:
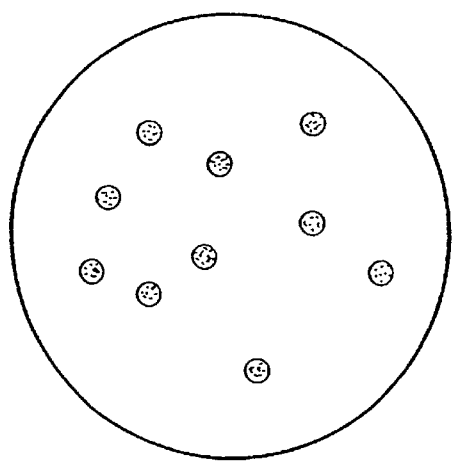
Figure 16B:
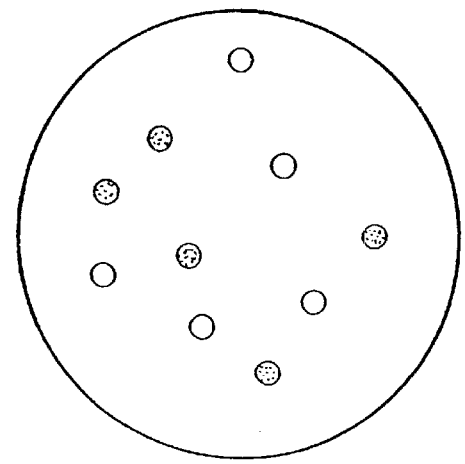

Expected results for heterozygous and homozygous samples are depicted in FIG. 16. The large circles represent a target sample dot on the slide. The small circles represent individual TS-DNA molecules, amplified in situ at the location of target nucleic acids in the sample, which have been subjected to primer extension sequencing. In an actual assay, hundreds or thousands of individually detectable TS-DNA molecules would be present in a sample dot, and the area occupied by the collapsed TS-DNA would be much smaller. Fewer and larger TS-DNA spots are depicted in FIG. 16 for clarity of illustration. The nucleotide incorporated is identified by its fluorescent spectrum and is based on the nucleotide present at the interrogated position in the TS-DNA. FIG. 16A is representative of a sample that is homozygous for the wild type sequence (indicated by incorporation of cystine). All of the cells in the sample (and thus, all of the target nucleic acids in the sample) have the same sequence resulting in the same incorporated nucleotide for all of the TS-DNA molecules in the sample. FIG. 16B is representative of a sample that is heterozygous for the wild type and a mutant (indicated by an equal number of TS-DNA molecules resulting in incorporation of cystine and adenine). All of the cells in the sample (and thus, all of the target nucleic acids in the sample) have one copy of both sequences (that is, wild type and mutant), resulting in the incorporation of two different nucleotides; each for half of the TS-DNA molecules in the sample. FIG. 16C is representative of a sample that is homozygous but includes a few cells with a somatic mutation. Most of the cells in the sample (and thus, most of the target nucleic acids in the sample) have the same sequence (that is, wild type), and only a few have the mutant sequence. This results in the incorporation of one nucleotide for most of the TS-DNA molecules, and incorporation of a different nucleotide for a few TS-DNA molecules. The ratio of the number of TS-DNA molecules for which a given nucleotide is incorporated is an accurate measure of the ratio of the corresponding target nucleic acid in the sample. Such sensitive detection of somatic mutations will be particularly useful for detecting, for example, a few cancer cells, or a few virally infected cells, in a sample containing mostly normal or uninfected cells.

Example 10

Unimolecular Segment Amplification and CAGE Sequencing

This example illustrates unimolecular segment amplification (that is, rolling circle amplification) followed by degenerate probe primer extension sequencing using caged oligonucleotides. In this example, an OCP is hybridized to a target nucleic acid so as to leave a gap in a region of known sequence variation. After formation of an amplification target circle using gap-filling ligation, and after rolling circle amplification of the amplification target circle, interrogation probes are hybridized to the amplified DNA. Interrogation primers are then formed by ligating degenerate probe to the interrogation probes. The interrogation primers are then extended in chain terminating primer extension sequencing using uniquely labeled chain-terminating nucleotides. This example illustrates the use of sequential addition of degenerate probes to hybridized interrogation probes in an arrayed solid-state sample. Detection of the incorporated label identifies the nucleotide sequence in the region of interest.

An Open Circle Probe (OCP.96) of 96 bases with a 5'-phosphate is designed to hybridize with a GT repeat polymorphic locus. The probe is designed to leave a gap in the GT repeat region when hybridized to the target DNA. The gap is to be filled by a DNA polymerase in a gap-filling ligation operation, thereby incorporating the entire GT repeat region into the ligated OCP.

The sequences of the OCP (96 bases) is as follows:

<u>ATCTAGCTATGTACGTACGTGAA</u>CTTTTCTTGCATGGTCACACGTCG

TTCTAGTACGCTTCTAACTTTTAACATAT<u>CTCGACATCTAACGATCG</u>

AT (nucleotides 1 to 96 of SEQ ID NO:25)

The underlined ends of this probe hybridize with the target DNA as indicated in FIG. 17. In FIG. 17, the gap space is indicated as "Fill sequence". FIG. 17A shows hybridization of the OCP to target DNA having 10 repeats of CA. FIG. 17B shows hybridization of the OCP to target DNA having 9 repeats of CA. As will be shown, USA-CAGESEQ is a useful and accurate method of determining the nucleotide sequence in a highly repetitive region of DNA.

Figure 18B:
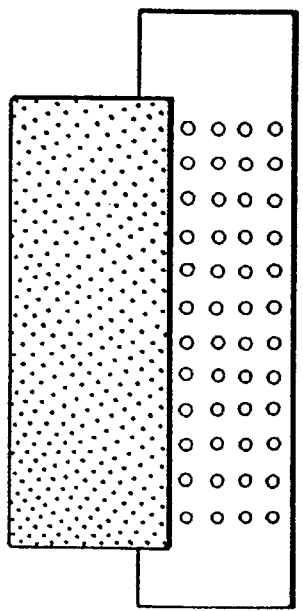
FIGS. 18A, 18B, 18C, 18D, and 18E are diagrams showing a slide containing an array of nucleic acid samples and coverage of rows of samples with a mask during unimolecular segment amplification and cage sequencing (USA-CAGESEQ).
Figure 18D:
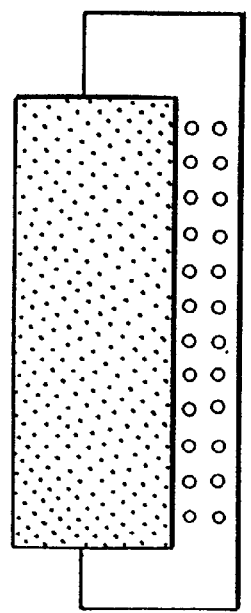
Figure 18E:
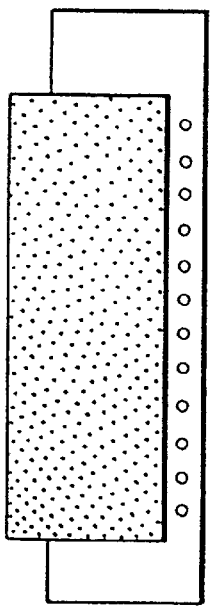
Figure 18A:
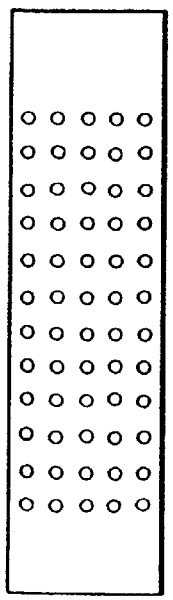

1. Five microscope slides, each containing at least one vertically aligned column of five identical bound denatured DNA samples are prepared as described by Schena et al. Each slide may contain from one to 100 regularly spaced columns of DNA samples, as long as the number of sample dots in each column is five. The slides should be identical (or at least have an identical set of DNA samples). An example of a slide with an array of bound DNA samples is shown in FIG. 18A. The five sample dots in each column are identical (that is, they are from the same DNA sample). Each column of sample dots is preferably made from different sample samples.

2a. The slides are incubated in 50 mM Tris-HCl, pH 7.5, 0.3 M NaCl, 0.5 mM EDTA, and 150 nM OCP.96 oligo, for 1 hour at 48° C. to achieve hybridization of the OCP. The slides are then washed for 2 minutes in 50 mM Tris-HCl, pH 7.5, 100 mM M KCl, and 0.05% Triton X-100.

2b. Gap-filling ligation is carried out in the presence of Ampligase DNA ligase and *Thermus flavus* DNA polymerase using the conditions described above (generally using conditions described by Abravaya et al.) in the presence of dATP, dCTP, dGTP, and dTTP, so that the gap is filled and immediately ligated. The incubation is carried out with the slides covered with a 22 by 40 mm cover slip, in a volume of 28 μl, for 45 minutes at 54° C.

3. Wash slides twice in 2× SSC with 20% formamide for 5 minutes at 42° C.

4. Wash slides for 2 minutes with 20 mM Tris, pH 7.5, and 0.075 M NaCl.

5. Rolling Circle Amplification is carried out in situ for 15 minutes at 30° C. in a buffer containing the following components: 50 mM Tris-HCl pH 7.5, 10 mM MgCl$_2$, 1 mM DTT, 400 µM each of dCTP, dATP, dGTP, 95 µM dTTP, 360 µM BUDR triphosphate (SIGMA), the 18 nucleotide rolling circle replication primer, ACGACGTGTGACCATGCA (SEQ ID NO:22), at a concentration of 700 nM, Phage T4 Gene-32 protein at a concentration of 1000 nMolar, and Φ29 DNA polymerase at 200 nM. This reaction generates approximately 400 copies of TS-DNA containing faithful copies of the target DNA.

6. Wash twice in 2× SSC with 20% formamide for 5 minutes at 25° C.

7a. Incubate one slide (slide number 1) in 2× SSC and 300 nMolar of a first 20 nucleotide interrogation probe (interrogation probe 1), TCTCGACATCTAACGATCGA (nucleotides 76 to 95 of SEQ ID NO:25), which hybridizes with the TS-DNA.

7b. Incubate another slide (slide number 2) in 2× SSC and 300 nMolar of a second 20 nucleotide interrogation probe (interrogation probe 2), CTCGACATCTAACGATCGAT (nucleotides 77 to 96 of SEQ ID NO:25), which hybridizes with the TS-DNA.

7c. Incubate another slide (slide number 3) in 2× SSC and 300 nMolar of a third 20 nucleotide interrogation probe (interrogation probe 3), TCGACATCTAACGATCGATC (nucleotides 78 to 97 of SEQ ID NO:25), which hybridizes with the TS-DNA.

7d. Incubate another slide (slide number 4) in 2× SSC and 300 nMolar of a fourth 20 nucleotide interrogation probe (interrogation probe 4), CGACATCTAACGATCGATCC (nucleotides 79 to 98 of SEQ ID NO:25), which hybridizes with the TS-DNA.

7e. Incubate another slide (slide number 5) in 2× SSC and 300 nMolar of a fifth 20 nucleotide interrogation probe (interrogation probe 5), GACATCTAACGATCGATCCT (nucleotides 80 to 99 of SEQ ID NO:25), which hybridizes with the TS-DNA.

The five interrogation probes constitute a nested set as described earlier. Their relationship to the amplified TS-DNA is shown below:

```
Probe 1    TCTCGACATCTAACGATCGA
Probe 2     CTCGACATCTAACGATCGAT
Probe 3      TCGACATCTAACGATCGATC
Probe 4       CGACATCTAACGATCGATCC
Probe 5        GACATCTAACGATCGATCCT
               ||||||||||||||||||||
TS-DNA     TAGAGCTGTAGATTGCTAGCTAGGATCACACACACACACA
```

Probe 1 is nucleotides 76 to 95 of SEQ ID NO:25, probe 2 is nucleotides 77 to 96 of SEQ ID NO:25, probe 3 is nucleotides 78 to 97 of SEQ ID NO:25, probe 4 is nucleotides 79 to 98 of SEQ ID NO:25, probe 5 is nucleotides 80 to 99 of SEQ ID NO:25, and the TS-DNA (shown 3' to 5') is nucleotides 19 to 60 of SEQ ID NO:19.

8. The slides are washed for 2 minutes in 50 mM Tris-Cl pH 7.5, 150 mM KCl, and 0.05% Triton X-100.

9. The slides are then subjected to five sequential rounds of degenerate probe ligation. Each round consists of the following steps:

(a) The 5 slides are incubated with a ligation reaction mixture that contains the following components:
(i) A full set of pentamer degenerate probes (that is, a mixture of oligonucleotides representing all 1,024 possible pentameric sequences), each degenerate probe at a concentration of 40 nMolar, where each degenerate probe has a 5' phosphate and a modified nucleotide at the 3' end (that is, a block at the 3' end). In this example, the modified nucleotides are caged nucleotides which are of the following form:

2'-Deoxy-3'-O-(2-nitrobenzyl)adenosine
2'-Deoxy-3'-O-(2-nitrobenzyl)guanosine
2'-Deoxy-3'-O-(2-nitrobenzyl)thymidine
2'-Deoxy-3 '-O-(2-nitrobenzyl)cytosine These nucleotides are described by Metzker et al., *Nucleic Acids Research* 22:4259–4267 (1994). The modified bases protect (that is, block) the 3'-hydroxyl and render the degenerate probes incapable of participating in DNA polymerase extension or DNA ligation.

(ii) A suitable DNA ligase, preferably Phage T4 DNA ligase.

Ligation is carried out with T4 DNA ligase (New England Biolabs) at a concentration of 8 units per µl, in a buffer consisting of 10 mM Tris-HCl, pH 7.5, 0.18 M NaCl, 12 mM MgCl$_2$, 2 mM ATP, and 10% polyethylene glycol. The total volume is 25 µl. Ligation is carried out for 40 minutes at 32° C.

(b) A primer extension reaction is carried out for 5 minutes at 37° C. in 25 µl, under a cover slip, in the presence of 5 Units Sequenase DNA polymerase (Amersham-USB), 50 mM Tris-HCl, pH 7.5, 20 mM MgCl$_2$, 50 mM NaCl, 5 mM DTT, 50 µg/ml Bovine Serum Albumin (Molecular Biology grade from Life Sciences, Inc.) 50 µM ddATP, ddCTP, ddGTP, ddTTP. This reaction blocks all the primer 3' ends that failed to participate in a ligation event. The slides are washed for 5 minutes in 2× SSC at 25° C. to remove any unligated degenerate probes.

After these steps, all of the interrogation probes are ligated to a degenerate probe. In the first round of degenerate probe ligation, an opaque "mask" is laid over the first row of DNA sample dots in all of the slides (see FIG. 18B). This mask thus covers the first sample dot of each column. The slides are exposed to UV light for 4 minutes to remove the cage structures from all the ligated degenerate probes in all the sample rows except row 1, which is not illuminated.

Figure 18C:
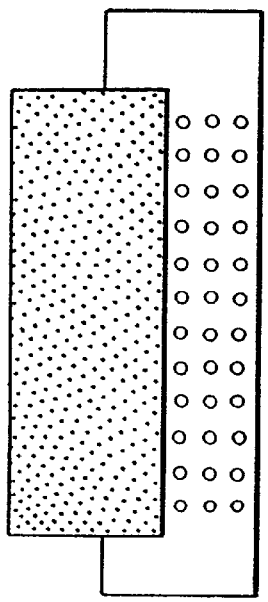

For the second round of degenerate probe ligation, steps (a) and (b) are repeated. Degenerate probes can only be ligated to DNA sample dots in rows 2 to 5 since the cage structure remains at the 3' end of the degenerate probes ligated to the DNA sample dots in the first row. After these steps, the interrogation probes in rows 2 to 5 are ligated to two degenerate probes. Then the opaque mask is laid over the first and second rows of DNA sample dots in all of the slides (see FIG. 18C). The mask thus covers the first and second sample dots of each column. The slides are exposed to UV light for 4 minutes to remove the cage structures from all the ligated degenerate probes in all the sample rows except rows 1 and 2, which are not illuminated.

For the third round of degenerate probe ligation, steps (a) and (b) are repeated. Degenerate probes can only be ligated to DNA sample dots in rows 3 to 5 since the cage structure remains at the 3' end of the degenerate probes ligated to the DNA sample dots in rows 1 and 2. After these steps, the interrogation probes in rows 3 to 5 are ligated to three degenerate probes. Then the opaque mask is laid over rows 1, 2 and 3 of DNA sample dots in all of the slides (see FIG. 18D). The mask thus covers the first, second and third sample dots of each column. The slides are exposed to UV light for 4 minutes to remove the cage structures from all the ligated degenerate probes in the fourth and fifth sample rows. The cage structures are not removed from the degenerate probes in sample rows 1, 2 and 3 since they are not illuminated.

For the fourth round of degenerate probe ligation, steps (a) and (b) are repeated. Degenerate probes can only be ligated to DNA sample dots in the fourth and fifth rows since the cage structure remains at the 3' end of the degenerate probes ligated to the DNA sample dots in rows 1, 2 and 3. After these steps, the interrogation probes in the fourth and fifth rows are ligated to four degenerate probes. Then the opaque mask is laid over rows 1, 2, 3 and 4 of DNA sample dots in all of the slides (see FIG. 18E). The mask thus covers the first, second, third and fourth sample dots of each column. The slides are exposed to UV light for 4 minutes to remove the cage structures from all the ligated degenerate probes in the fifth sample row. The cage structures are not removed from the degenerate probes in sample rows 1, 2, 3 and 4 since they are not illuminated.

For the fifth round of degenerate probe ligation, steps (a) and (b) are repeated. Degenerate probes can only be ligated to DNA sample dots in the fifth row since the cage structure remains at the 3' end of the degenerate probes ligated to the DNA sample dots in rows 1, 2, 3 and 4. After these steps, the interrogation probes in the fifth row are ligated to five degenerate probes. The slides are then exposed to UV light without the mask for 4 minutes to remove the cage structures from all the ligated degenerate probes in all the sample rows. This leaves all of the ligated probes (which can now be considered interrogation primers) ready for chain terminating primer extension.

FIGS. 21A, 21B, 21C, 21D, 21E, 23A, 23B, 23C, 23D, and 23E depict the results of the above degenerate probe ligation. The interrogation primers (the top, shorter sequences following the row labels) formed by ligation of degenerate probes to the interrogation probes are shown hybridized to TS-DNA (the longer sequences below each interrogation primer) for all of the five sample dots in one column of each of the five slides. In each slide, one additional degenerate probe has been added in each succeeding row, which is a consequence of successively covering one additional row of sample dots during each round of degenerate probe ligation. The non-underlined portions of the interrogation primers represent the interrogation probe. The underlined portions of the interrogation primers represent degenerate probes ligated to the end of the interrogation probe. Careful examination of all the interrogation primers in each set of five slides reveals that each ends adjacent to a different nucleotide in the TS-DNA. This allows an entire stretch of nucleotides to be separately interrogated (that is, sequenced). FIGS. 21A, 21B, 21C, 21D, and 21E depict the results with a normal target sequence (that is, having 10 repeats of CA). FIGS. 23A, 23B, 23C, 23D, and 23E depict the results with a mutant target sequence (that is, having only nine repeats of CA).

10. The slides are then subjected to chain terminating primer extension carried out for 5 minutes at 37° C. in a volume of 25 µl, under a cover slip, in the presence of 5 Units Sequenase DNA polymerase (Amersham-USB), 50 mM Tris-Cl, pH 7.5, 20 mM MgCl$_2$, 50 mM NaCl, 5 mM DTT, 50 µg/ml Bovine Serum Albumin (Molecular Biology grade from Life Sciences, Inc.) 50 µM fluorescent-ddATP, 50 µM fluorescent-ddCTP, 50 µM fluorescent-ddGTP, 50 µM fluorescent-ddTTP, each fluorescent dNTP being able to generate a signal with a different emission spectrum (Applied Biosystems, Inc. Sequencing kit). In this reaction, one fluorescent nucleotide is added to the end of each interrogation primer. The identity of the added nucleotide is based on the identity of the template nucleotide (the nucleotide adjacent to the interrogation primer).

11. Wash 5 minutes in 2× SSC at 25° C.

12. Wash 4 minutes in 2× SSC, 2.8% BSA, 0.12% Tween-20 at 37° C.

13. Incubate 30 minutes at 37° C. in 50 µl (under cover slip) using 5 µg/ml Biotinylated AntiBUDR-Mouse.IgG (Zymed Labs) in 2× SSC, 2.8% BSA, 0.12% Tween-20. This reaction collapses the TS-DNA molecules into a compact structures on the slides.

14. Wash three times for 5 minutes in 2× SSC, 2.8% BSA, 0.12% Tween-20 at 37° C.

15. Incubate 30 minutes at 37° C. in 50 µl (under cover slip) using FITC-Avidin, 5 µg/ml. in 2× SSC, 2.8% BSA, 0.12% Tween-20. This labels each TS-DNA molecule with fluorescein.

16. Wash three time for 5 minutes in 2× SSC, 2.8% BSA, 0.12% Tween-20 at 37° C.

17. Wash 5 minutes with 2× SSC, 0.01% Tween-20 at room temperature.

18. The image of each slide is captured using a microscope-CCD camera system with appropriate filter sets. The fluorescent emission color of each fluorescent nucleotide defines the nucleotide at the specific extension position in each fluorescent spot. Each spot corresponds to a single molecule of TS-DNA. FIGS. 22A, 22B, 22C, 22D, 22E, 24A, 24B, 24C, 24D, and 24E depict the results chain terminating primer extension. The interrogation primers, now with a fluorescent nucleotide (in boldface) added to the end, are shown hybridized to TS-DNA for all of the five sample dots in one column of each of the five slides. In each slide, a different nucleotide in a stretch of nucleotides in the TS-DNA has served as the template for the incorporation of a chain terminating fluorescent nucleotide. Thus, each of the nucleotides in this stretch has been separately interrogated (that is, sequenced). FIGS. 22A, 22B, 22C, 22D, and 22E depict the results with a normal target sequence (that is, having 10 repeats of CA). FIGS. 24A, 24B, 24C, 24D, and 24E depict the results with a mutant target sequence (that is, having only nine repeats of CA).

Figure 19:
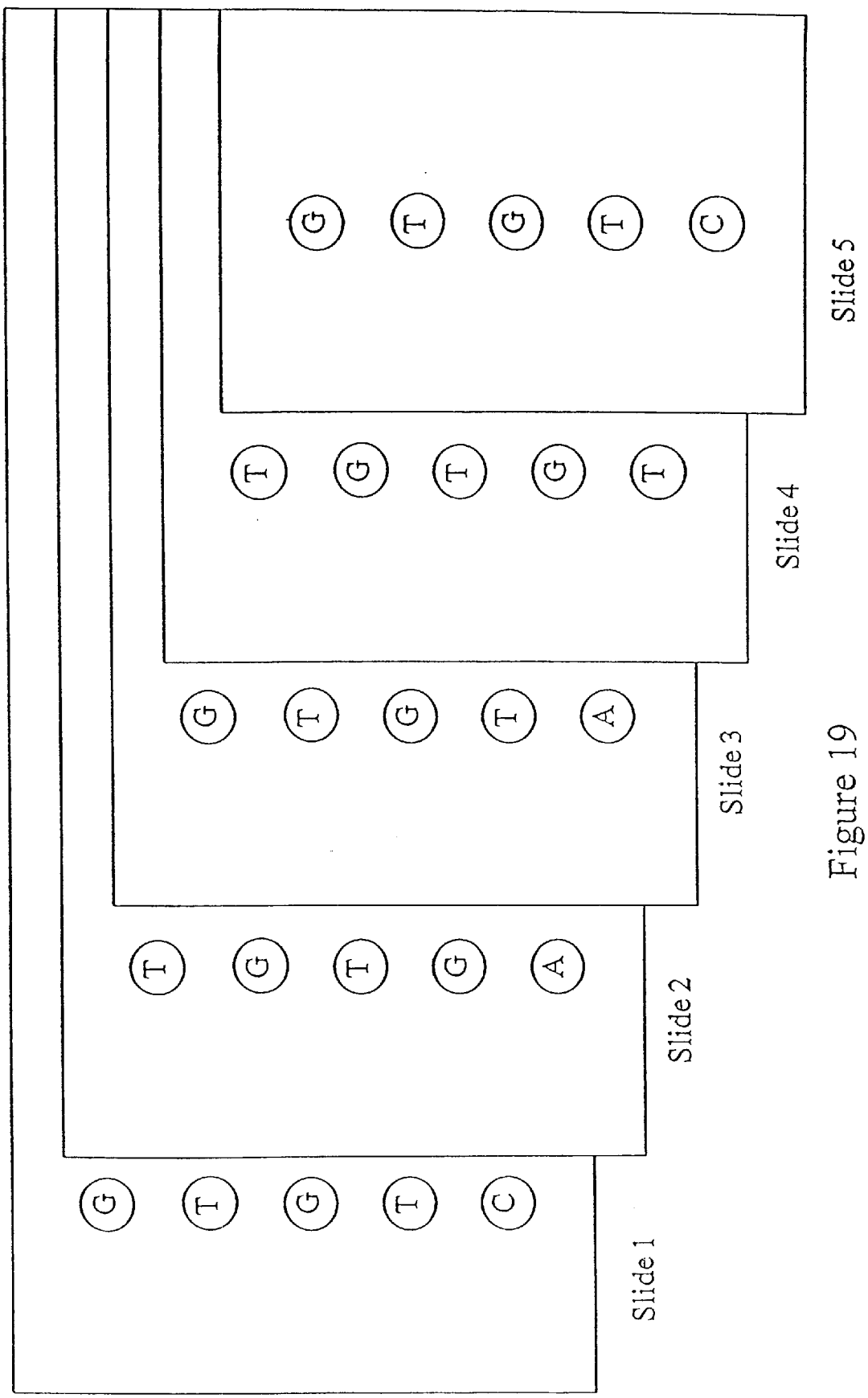
FIG. 19 is a diagram showing the nucleotide incorporated in the first column of samples on a slide subjected to USA-CAGESEQ. The samples correspond to the target sequence shown in FIG. 17A.
Figure 20:
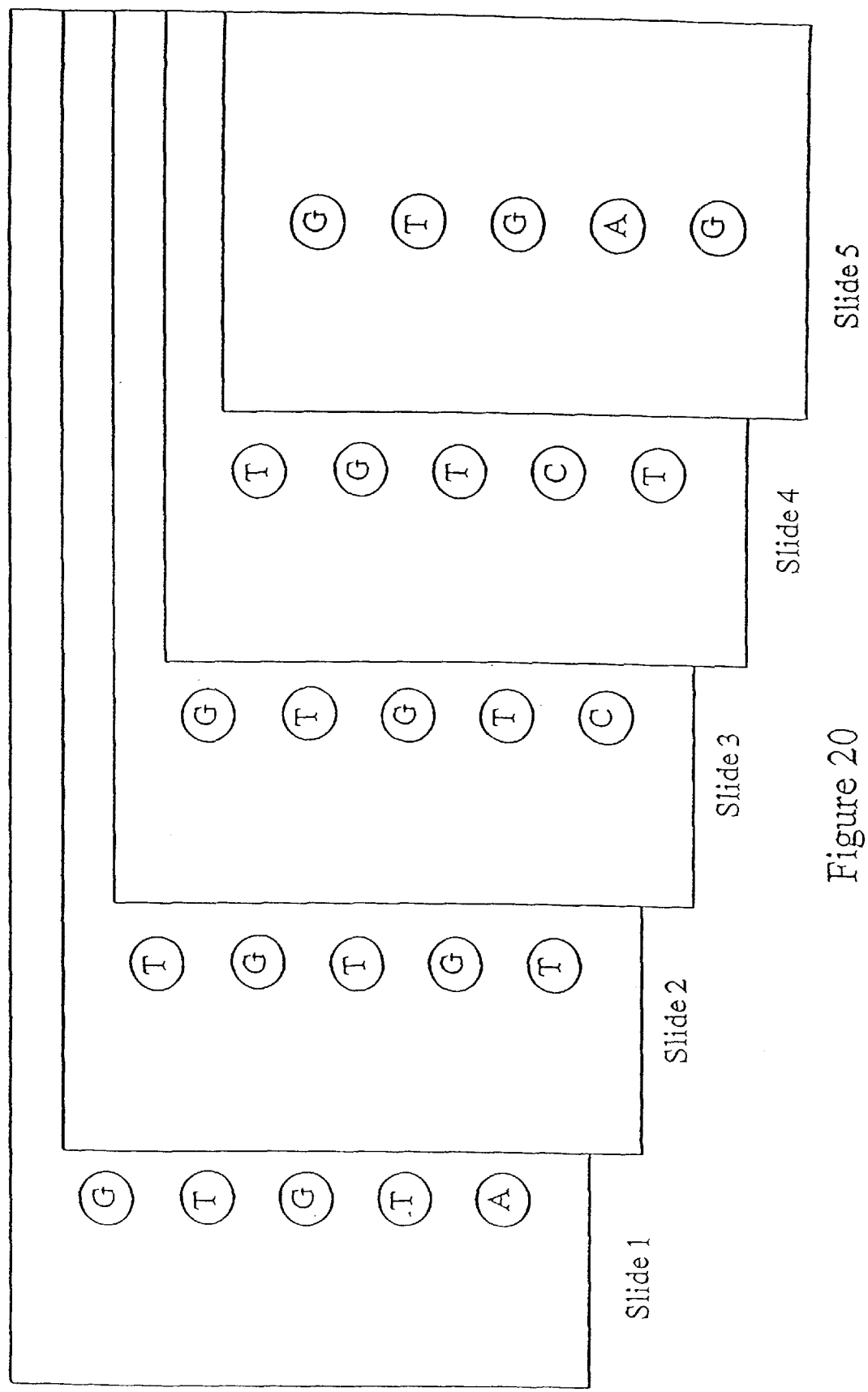
FIG. 20 is a diagram showing the nucleotide incorporated in the first column of samples on a slide subjected to USA-CAGESEQ. The samples correspond to the target sequence shown in FIG. 17B.
Figure 25A:
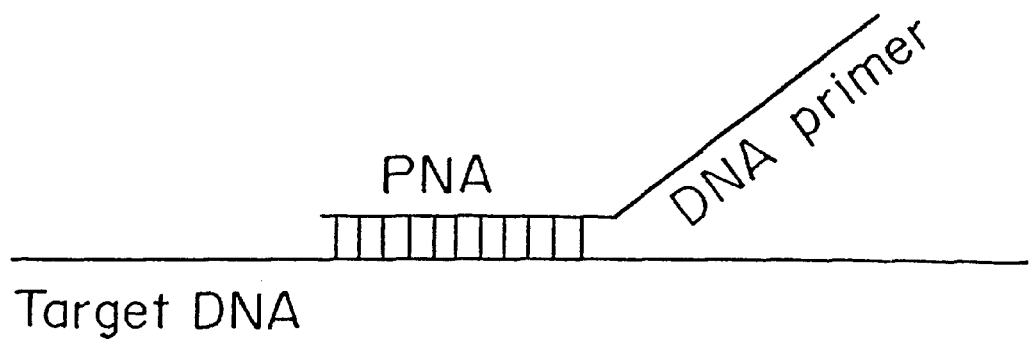
FIGS. 25A and 25B are diagrams of a reporter binding molecule made up of a peptide nucleic acid (as the affinity portion) and a rolling circle replication primer (as the oligonucleotide portion). The affinity portion is shown hybridized to a target DNA.
Figure 25B:
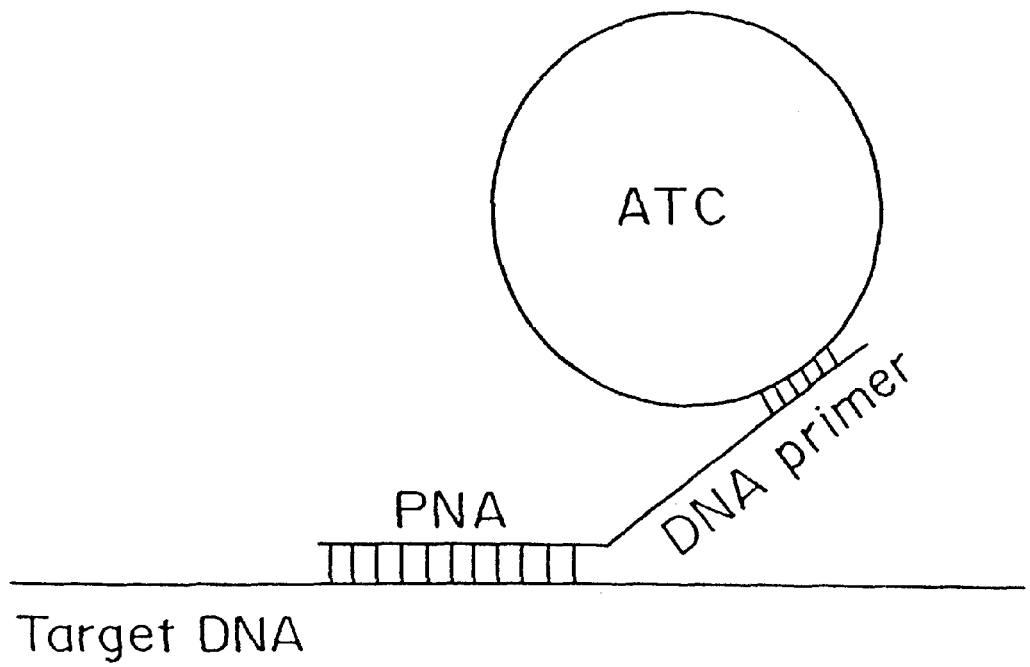
Figure 26A:
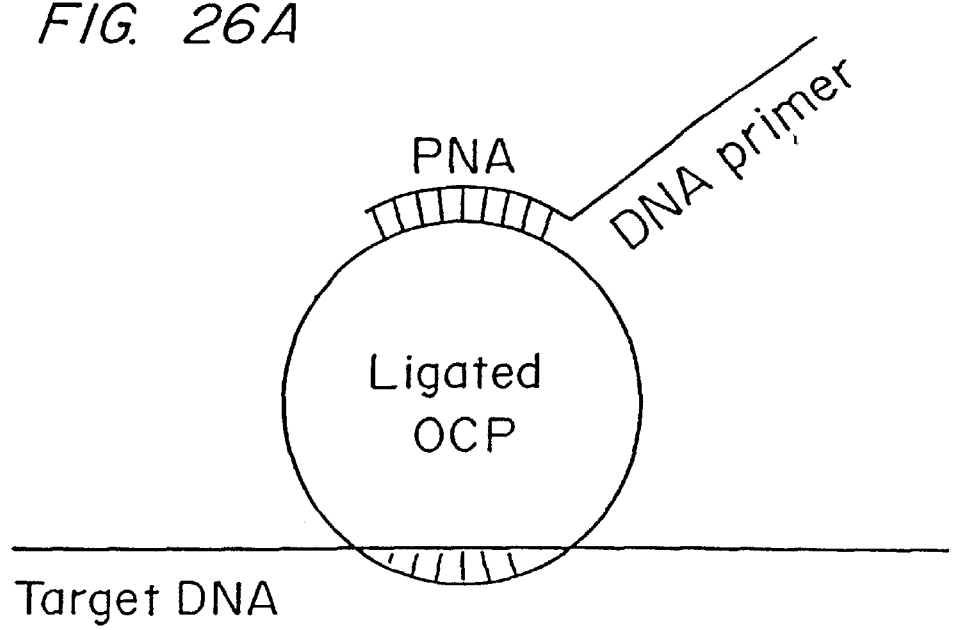
FIGS. 26A and 26B are diagrams of a reporter binding molecule hybridized to a ligated open circle probe that is topologically locked to target DNA. The reporter binding molecule made up of a peptide nucleic acid (as the affinity portion) and a rolling circle replication primer (as the oligonucleotide portion).
Figure 26B:
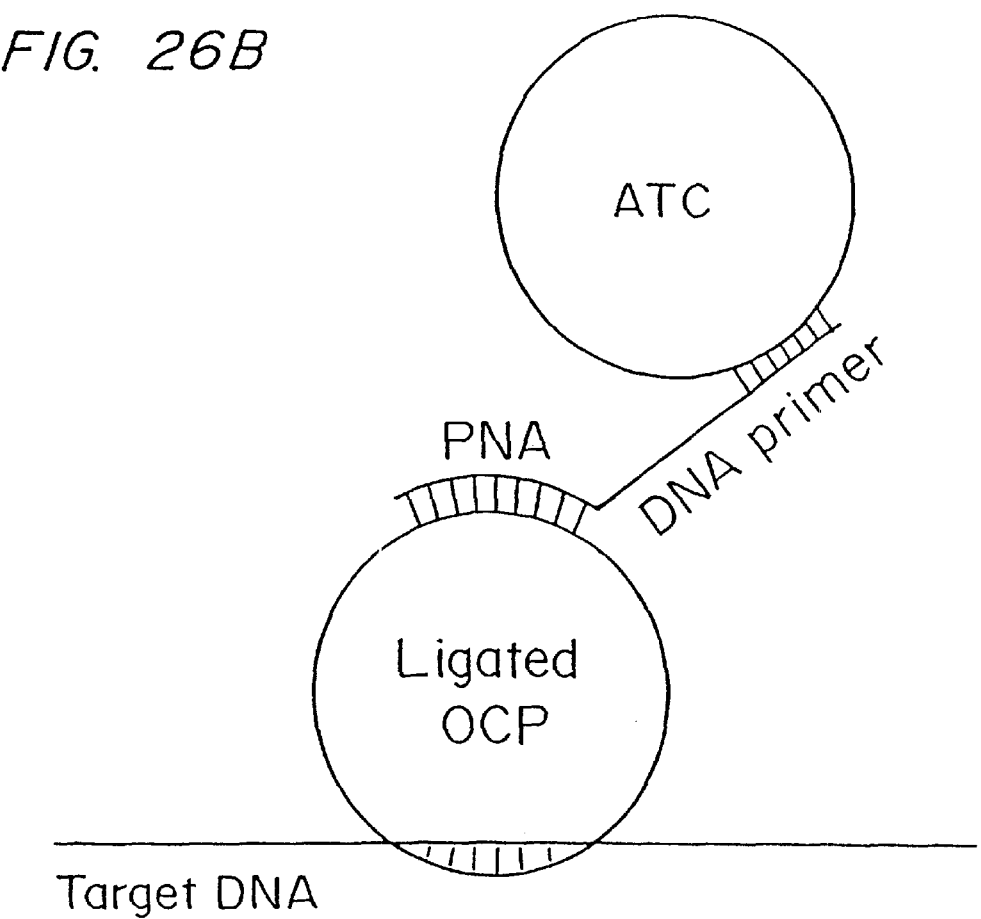
Figure 27A:
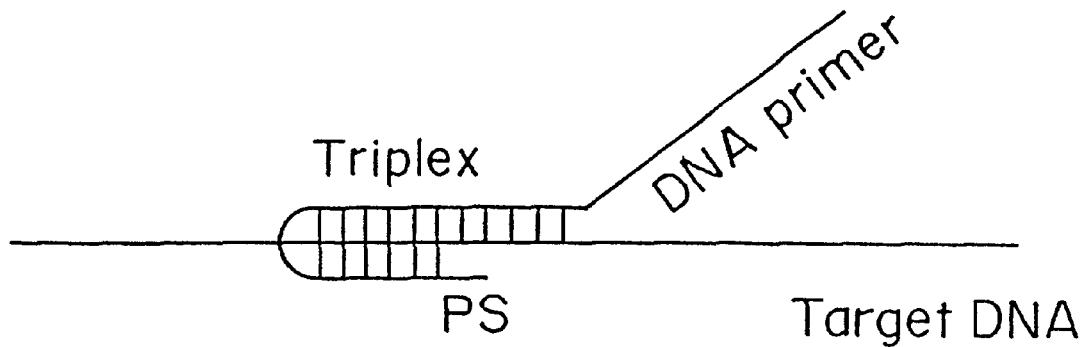
FIGS. 27A and 27B are diagrams of a reporter binding molecule made up of a chemically-linked triple helix-forming oligonucleotide (as the affinity portion) and a rolling circle replication primer as the oligonucleotide portion. The affinity portion is shown hybridized to a target DNA. PS indicates a psoralen derivative creating a chemical link between the affinity portion and the target DNA.
Figure 27B:
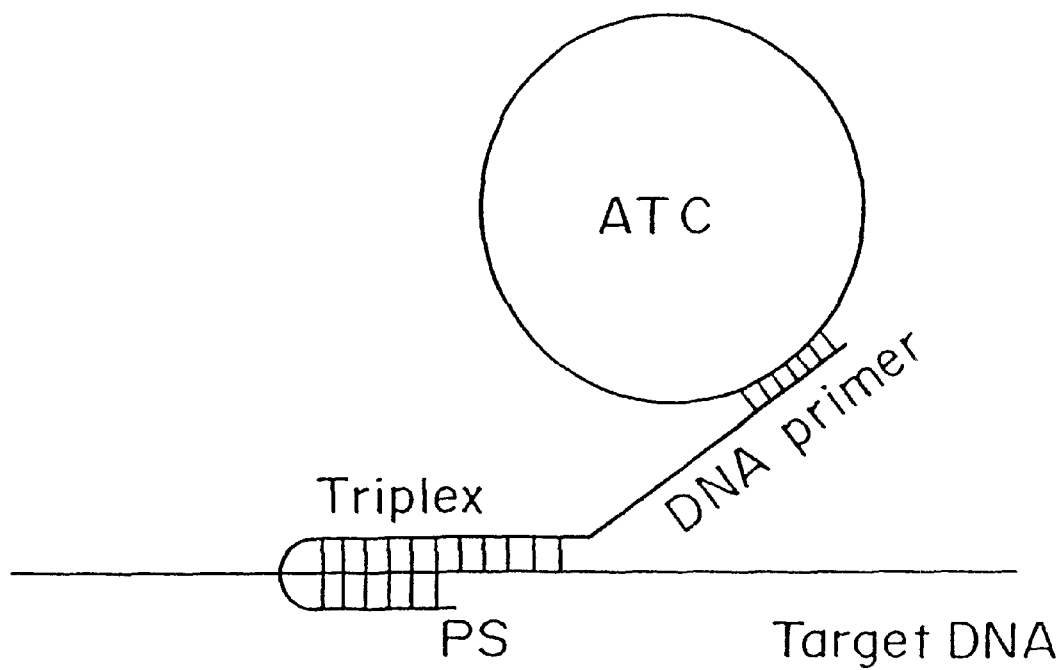
Figure 28A:
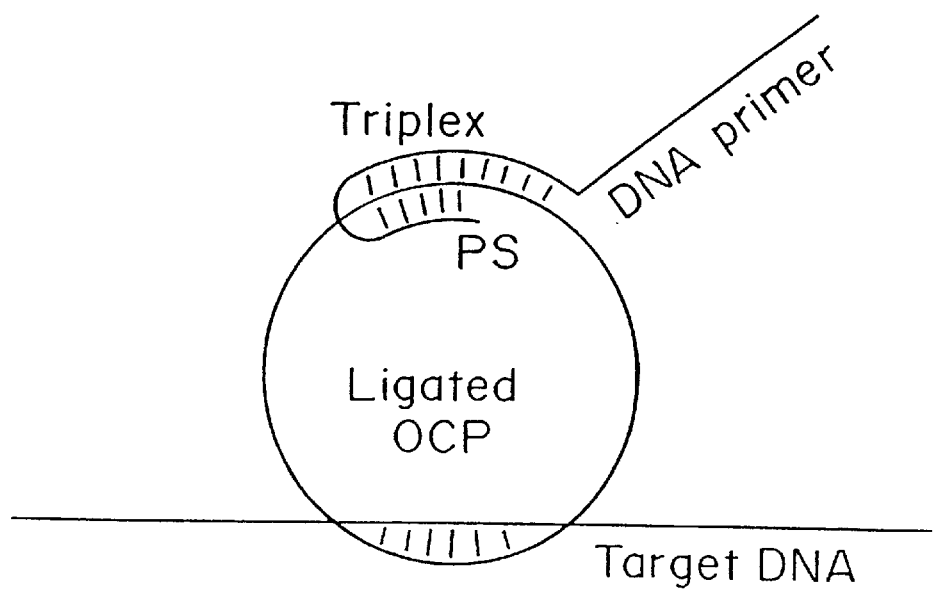
FIGS. 28A and 28B are diagrams of a reporter binding molecule hybridized to a ligated open circle probe that is topologically locked to target DNA. The reporter binding molecule made up of a chemically-linked triple helix-forming oligonucleotide (as the affinity portion) and a rolling circle replication primer as the oligonucleotide portion. PS indicates a psoralen derivative creating a chemical link between the affinity portion and the target DNA.
Figure 28B:
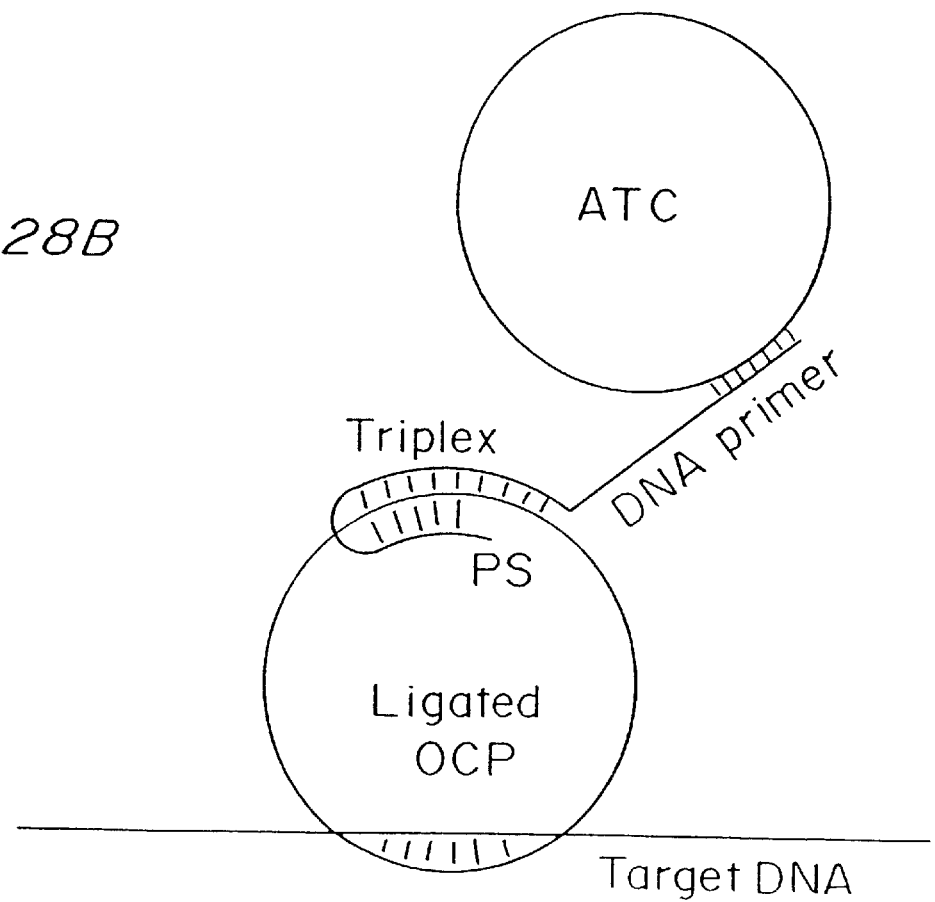

19. The sequence is assembled from the fluorescent spot data obtained from all five slides, by reading the incorporated nucleotide in each related sample dot in the order. FIGS. 19 and 20 diagrammatically depict the incorporated nucleotides for each sample dot in corresponding columns of each of the five slides. FIG. 19 represents the results with the normal target sequence (that is, having 10 repeats of CA). FIG. 20 represents the results with a mutant target sequence (that is, having only nine repeats of CA). The nucleotides are read first from the first sample dot in a given column from each slide in order (that is, the sample dot in row 1 of slide 1, the sample dot in row 1 of slide 2, the sample dot in row 1 of slide 3, the sample dot in row 1 of slide 4, and the sample dot in row 1 of slide 5). The next nucleotides are read from the second sample dot in the column from each slide in order (that is, the second sample dot in row 2 of slides 1 to 5 in order). The reading of nucleotides continues in the same manner for sample dots in rows 3, 4, and 5 in order. The relationship of the sample dots which leads to this order of reading can be seen by carefully examining the relationship of the interrogated nucleotides in FIGS. 22A, 22B, 22C, 22D, 22E, 24A, 24B, 24C, 24D, and 24E. The sequence read from the slides depicted in FIG. 19 is GTGTGTGTGTGT-GTGTGTGTCAATC (nucleotides 105 to 125 of SEQ ID NO:25). The sequence read from the slides depicted in FIG. 20 is GTGTGTGTGTGTGTGTGTCAATCTG (nucleotides 30 to 50 of SEQ ID NO: 18). The difference in the number of GT repeats between these two sequences is readily apparent.

Example 11

Immunoassay for Human TSH Coupled to Rolling Circle Amplification

This example describes single-molecule detection of human thyroid stimulating hormone (hTSH) using a capture antibody, and a reporter antibody. The reporter antibody is of the form illustrated in FIG. 29A where an antibody is coupled to a rolling circle replication primer. The signal that is detected is produced by rolling circle amplification primed by the rolling circle replication primer portion of the reporter antibody.

1. A malemide-modified monoclonal antibody specific for hTSH is coupled to the 5'-end of the 28-base oligonucleotide 5'-[amino]-TTTTTTTTTTGCTGAGACATGACGAGTC-3' (SEQ ID NO:27) using SATA chemistry as described by Hendrickson et al. to form a reporter antibody. The 18 nucleotides at the 3' end of this oligonucleotide are complementary to the ATC described below. This oligonucleotide serves as the rolling circle replication primer for the amplification operation below.

2. hTSH capture antibodies, specific for a different epitope from that recognized by the reporter antibody, are immobilized at defined positions using droplets of 2 mm diameter on derivatized glass slides (Guo et al. (1994)) to make a solid-state detector. Droplets of 1.5 microliters, containing 5 μg/ml of the antibody in sodium bicarbonate pH 9 are applied at each defined position on the slides, incubated overnight, and then the entire slide is washed with PBS-BLA (10 mM sodium phosphate, pH 7.4, 150 mM sodium chloride, 2% BSA, 10% Beta-lactose, 0.02% sodium azide) to block non-adsorbed sites.

3. Serial dilutions of hTSH are added to each of several identical slides, under cover slips. After 1 hour of incubation, the slides are washed three times with TBS/Tween wash buffer (Hendrickson et al.). The hTSH is now captured on the surface of the glass slides.

4. Thirty microliters of appropriately diluted mixture of the reporter antibody (antibody coupled to rolling circle replication primer) is added to each slide, under a cover slip. The slides are incubated at 37° C. for 1 hour, and then washed four times, for 5 minutes each wash, with 2× SSC, 2.8% BSA, 0.12% Tween-20 at 37° C.

5. The ATC is a 94-base closed circular oligonucleotide of the following sequence

```
                                              (SEQ ID NO:28)
5'-AAATCTCCAACTGGAAACTGTTCTGACTCGTCATGTCTC
```
-continued
```
AGCTCTAGTACGCTGATCTCAGTCTGATCTCAGTCATTTGGTCTCAA
AGTGATTG-3'.
```

Figure 29B:
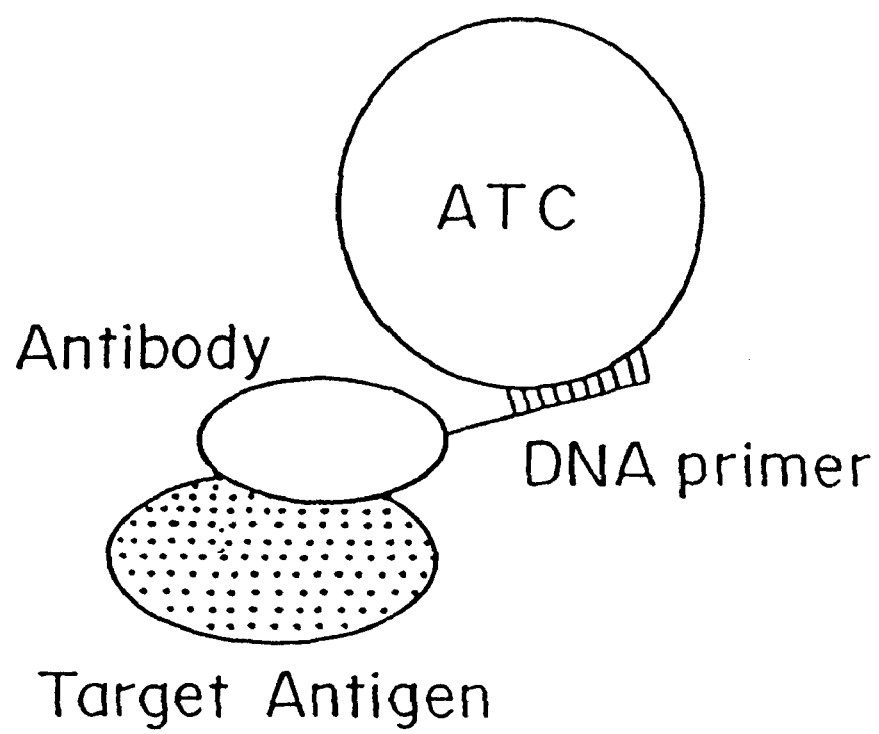

This ATC oligonucleotide is incubated in a volume of 30 microliters on the surface of the glass slide, under a cover slip, in a buffer consisting of 50 mM Tris-Cl, pH 7.4, 40 mM KOAC, 10 mM $MgCl_2$, in order to hybridize the ATC to the rolling circle replication primer portion of the reporter antibodies. This hybridization is illustrated in FIG. 29B.

6. In situ Rolling Circle Amplification is carried out for 12 minutes at 30° C., under a cover slip, in 30 microliters of a buffer containing the following components: 50 mM Tris-HCl pH 7.5, 10 mM $MgCl_2$, 400 μM each of dCTP, dATP, dGTP, 95 μM dTTP, 380 μM BUDR triphosphate (SIGMA), Phage T4 Gene-32 protein at a concentration of 1000 nMolar, and Φ29 DNA polymerase at 200 nM. This reaction generates approximately 350 tandem copies of the ATC. The copies remain bound to the antibody as a single TS-DNA molecule since the rolling circle replication primer is incorporated within the TS-DNA (at the 5' end) and the rolling circle replication primer remains coupled to the antibody.

7. The slide is washed three times for 5 minutes in 2× SSC, 2.8% BSA, 0.12% Tween-20 at 37° C.

8. The slide is then incubated 30 minutes at 37° C. in 50 μl (under cover slip) of 2× SSC, 2.8% BSA, 0.12% Tween-20, and 5 μg/ml Biotinylated AntiBUDR-Mouse.IgG (Zymed Labs).

9. The slide is washed three times for 5 minutes in 2× SSC, 2.8% BSA, 0.12% Tween-20 at 37° C.

10. The slide is then incubated 30 minutes at 37° C. in 50 μl (under cover slip) of 2× SSC, 2.8% BSA, 0.12% Tween-20, and FITC-Avidin at 5 μg/ml.

11. The slide is washed 3×5 min. in 2× ssc, 2.8% BSA, 0.12% Tween-20 at 37° C.

12. The slide is washed 10 minutes with 1× SSC, 0.01% Tween-20 at room temperature.

13. An image of the slide is captured using a microscope-CCD camera system with appropriate filter sets for fluorescein detection, and the number of fluorescent dots is counted. This indicates the presence of, and relative amount of, hTSH present in the sample since each dot represents a single collapsed TS-DNA molecule and each TS-DNA molecule represents a single hTSH molecule captured on the slide.

All publications cited herein, and the material for which they are cited, are hereby specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method for detecting proteins, the method comprising an amplification operation,
wherein a rolling circle replication primer is coupled to a specific binding molecule, wherein the specific binding molecule can interact with a target molecule, wherein the target molecule is a protein,
wherein the amplification operation comprises rolling circle replication of an amplification target circle to produce tandem sequence DNA.

2. The method of claim 1 wherein the specific binding molecule is bound to a target molecule.

3. The method of claim 1 further comprising bringing the specific binding molecule into contact with the target molecule.

4. The method of claim 1 wherein the method includes a step of bringing the specific binding molecule into contact with the target molecule.

5. The method of claim 1 wherein the specific binding molecule is an antibody.

6. The method of claim 1 wherein rolling circle replication of the amplification target circle is primed by the rolling circle replication primer.

7. The method of claim 1 wherein the amplification operation produces tandem sequence DNA and secondary tandem sequence DNA, wherein the method further comprises detecting the tandem sequence DNA, the secondary tandem sequence DNA, or both.

8. The method of claim 1 wherein a plurality of different rolling circle replication primers are used in the amplification operation.

9. The method of claim 8 wherein the rolling circle replication primers are each coupled to a different specific binding molecule.

10. The method of claim 9 wherein the different specific binding molecules each interacts with a different target molecule.

11. A method of detecting proteins, the method comprising,
(a) mixing a specific binding molecule with a target sample comprising a target molecule wherein a rolling circle replication primer is coupled to the specific binding molecule, wherein the specific binding molecule binds to the target molecule,
wherein the target molecule is a protein,
(b) mixing the rolling circle replication primer with an amplification target circle, to produce a primer-ATC mixture, and incubating the primer-ATC mixture under conditions that promote hybridization between the amplification target circle and the rolling circle replication primer in the primer-ATC mixture,
wherein the amplification target circle comprises a single-stranded, circular DNA molecule comprising a primer complement portion, wherein the primer complement portion is complementary to the rolling circle replication primer, and
(c) mixing DNA polymerase with the primer-ATC mixture, to produce a polymerase-ATC mixture, and incubating the polymerase-ATC mixture under conditions that promote replication of the amplification target circle,
wherein replication of the amplification target circle results in the formation of tandem sequence DNA.

12. A method for detecting proteins, the method comprising
an amplification operation,
wherein an amplification target circle is coupled to a specific binding molecule, wherein the specific binding molecule can interact with a target molecule, wherein the target molecule is a protein,
wherein the amplification operation comprises rolling circle replication of the amplification target circle to produce tandem sequence DNA.

13. The method of claim 12 wherein the specific binding molecule is bound to a target molecule.

14. The method of claim 12 further comprising bringing the specific binding molecule into contact with the target molecule.

15. The method of claim 12 wherein the method includes a step of bringing the specific binding molecule into contact with the target molecule.

16. The method of claim 12 wherein the specific binding molecule is an antibody.

17. The method of claim 12 wherein amplification target circle is tethered to the specific binding molecule so that the amplification target circle can rotate freely.

18. The method of claim 12 wherein the amplification operation produces tandem sequence DNA and secondary tandem sequence DNA, wherein the method further comprises detecting the tandem sequence DNA, the secondary tandem sequence DNA, or both.

19. The method of claim 12 wherein a plurality of different amplification target circles are used in the amplification operation.

20. The method of claim 19 wherein the rolling circle replication primers are each coupled to a different specific binding molecule.

21. The method of claim 20 wherein the different specific binding molecules each interacts with a different target molecule.

22. A method of detecting proteins, the method comprising,
(a) mixing a specific binding molecule with a target sample comprising a target molecule wherein an amplification target circle is coupled to the specific binding molecule, wherein the specific binding molecule binds to the target molecule,
wherein the target molecule is a protein,
(b) mixing a rolling circle replication primer with the amplification target circle, to produce a primer-ATC mixture, and incubating the primer-ATC mixture under conditions that promote hybridization between the amplification target circle and the rolling circle replication primer in the primer-ATC mixture,
wherein the amplification target circle comprises a single-stranded, circular DNA molecule comprising a primer complement portion, wherein the primer complement portion is complementary to the rolling circle replication primer, and
(c) mixing DNA polymerase with the primer-ATC mixture, to produce a polymerase-ATC mixture, and incubating the polymerase-ATC mixture under conditions that promote replication of the amplification target circle,
wherein replication of the amplification target circle results in the formation of tandem sequence DNA.

23. A method for detecting proteins, the method comprising
a DNA ligation operation and an amplification operation,
wherein the DNA ligation operation comprises circularization of an open circle probe, wherein circularization of the open circle probe is dependent on hybridization of the open circle probe to a target sequence, wherein the target sequence is coupled to a specific binding molecule, wherein the specific binding molecule can interact with a target molecule, wherein the target molecule is a protein, wherein the amplification operation comprises rolling circle replication of the circularized open circle probe to produce tandem sequence DNA.

24. The method of claim 23 wherein the specific binding molecule is bound to a target molecule.

25. The method of claim 23 further comprising bringing the specific binding molecule into contact with the target molecule.

26. The method of claim 23 wherein the method includes a step of bringing the specific binding molecule into contact with the target molecule.

27. The method of claim 23 wherein the amplification operation produces tandem sequence DNA and secondary tandem sequence DNA, wherein the method further comprises detecting the tandem sequence DNA, the secondary tandem sequence DNA, or both.

28. The method of claim 23 wherein a plurality of different target sequences are used in the amplification operation.

29. The method of claim 28 wherein the rolling circle replication primers are each coupled to a different specific binding molecule.

30. The method of claim 29 wherein the different specific binding molecules each interacts with a different target molecule.

31. A method of detecting proteins, the method comprising,
(a) mixing a specific binding molecule with a target sample comprising a target molecule wherein a target sequence is coupled to the specific binding molecule, wherein the specific binding molecule binds to the target molecule,
wherein the target molecule is a protein,
(b) mixing an open circle probe with the target sample, to produce an OCP-target sample mixture, and incubating the OCP-target sample mixture under conditions that promote hybridization between the open circle probe and the target sequence in the OCP-target sample mixture,
(c) mixing ligase with the OCP-target sample mixture, to produce a ligation mixture, and incubating the ligation mixture under conditions that promote ligation of the open circle probe to form an amplification target circle,
(d) mixing a rolling circle replication primer with the ligation mixture, to produce a primer-ATC mixture, and incubating the primer-ATC mixture under conditions that promote hybridization between the amplification target circle and the rolling circle replication primer in the primer-ATC mixture, and
(e) mixing DNA polymerase with the primer-ATC mixture, to produce a polymerase-ATC mixture, and incubating the polymerase-ATC mixture under conditions that promote replication of the amplification target circle,
wherein replication of the amplification target circle results in the formation of tandem sequence DNA.

32. A method comprising
an amplification operation,
wherein a nucleic acid tag is coupled to a specific binding molecule, wherein the specific binding molecule can interact with a target molecule, wherein the target molecule is a protein, wherein the amplification operation comprises rolling circle replication of an amplification target circle to produce tandem sequence DNA.

33. The method of claim 32 wherein the specific binding molecule is bound to a target molecule.

34. The method of claim 32 further comprising bringing the specific binding molecule into contact with the target molecule.

35. The method of claim 32 wherein the method includes a step of bringing the specific binding molecule into contact with the target molecule.

36. A method for detecting nucleic acid molecules, the method comprising
an amplification operation,
wherein a rolling circle replication primer is coupled to a specific binding molecule, wherein the specific binding molecule can interact with a target molecule, wherein the target molecule is a nucleic acid molecule,
wherein the amplification operation comprises rolling circle replication of an amplification target circle to produce tandem sequence DNA.

37. The method of claim 36 wherein the specific binding molecule is bound to a target molecule.

38. The method of claim 36 further comprising bringing the specific binding molecule into contact with the target molecule.

39. The method of claim 36 wherein the method includes a step of bringing the specific binding molecule into contact with the target molecule.

40. The method of claim 36 wherein rolling circle replication of the amplification target circle is primed by the rolling circle replication primer.

41. The method of claim 36 wherein the amplification operation produces tandem sequence DNA and secondary tandem sequence DNA, wherein the method further comprises detecting the tandem sequence DNA, the secondary tandem sequence DNA, or both.

42. The method of claim 36 wherein a plurality of different rolling circle replication primers are used in the amplification operation.

43. The method of claim 42 wherein the rolling circle replication primers are each coupled to a different specific binding molecule.

44. The method of claim 43 wherein the different specific binding molecules each interacts with a different target molecule.

45. A method of detecting nucleic acid molecules, the method comprising,
(a) mixing a specific binding molecule with a target sample comprising a target molecule wherein a rolling circle replication primer is coupled to the specific binding molecule, wherein the specific binding molecule binds to the target molecule,
wherein the target molecule is a nucleic acid molecule,
(b) mixing the rolling circle replication primer with an amplification target circle, to produce a primer-ATC mixture, and incubating the primer-ATC mixture under conditions that promote hybridization between the amplification target circle and the rolling circle replication primer in the primer-ATC mixture,
wherein the amplification target circle comprises a single-stranded, circular DNA molecule comprising a primer complement portion, wherein the primer complement portion is complementary to the rolling circle replication primer, and (c) mixing DNA polymerase with the primer-ATC mixture, to produce a polymerase-ATC mixture, and incubating the polymerase-ATC mixture under conditions that promote replication of the amplification target circle, wherein replication of the amplification target circle results in the formation of tandem sequence DNA.

46. A method for detecting nucleic acid molecules, the method comprising an amplification operation, wherein an amplification target circle is coupled to a specific binding molecule, wherein the specific binding molecule can interact with a target molecule, wherein the target molecule is a nucleic acid molecule, wherein the amplification operation comprises rolling circle replication of the amplification target circle to produce tandem sequence DNA.

47. The method of claim 46 wherein the specific binding molecule is bound to a target molecule.

48. The method of claim 46 further comprising bringing the specific binding molecule into contact with the target molecule.

49. The method of claim 46 wherein the method includes a step of bringing the specific binding molecule into contact with the target molecule.

50. The method of claim 46 wherein amplification target circle is tethered to the specific binding molecule so that the amplification target circle can rotate freely.

51. The method of claim 46 wherein the amplification operation produces tandem sequence DNA and secondary tandem sequence DNA, wherein the method further comprises detecting the tandem sequence DNA, the secondary tandem sequence DNA, or both.

52. The method of claim 46 wherein a plurality of different amplification target circles are used in the amplification operation.

53. The method of claim 52 wherein the rolling circle replication primers are each coupled to a different specific binding molecule.

54. The method of claim 53 wherein the different specific binding molecules each interacts with a different target molecule.

55. A method of detecting nucleic acid molecules, the method comprising, (a) mixing a specific binding molecule with a target sample comprising a target molecule wherein an amplification target circle is coupled to the specific binding molecule, wherein the specific binding molecule binds to the target molecule, wherein the target molecule is a nucleic acid molecule, (b) mixing the rolling circle replication primer with an amplification target circle, to produce a primer-ATC mixture, and incubating the primer-ATC mixture under conditions that promote hybridization between the amplification target circle and the rolling circle replication primer in the primer-ATC mixture, wherein the amplification target circle comprises a single-stranded, circular DNA molecule comprising a primer complement portion, wherein the primer complement portion is complementary to the rolling circle replication primer, and (c) mixing DNA polymerase with the primer-ATC mixture, to produce a polymerase-ATC mixture, and incubating the polymerase-ATC mixture under conditions that promote replication of the amplification target circle, wherein replication of the amplification target circle results in the formation of tandem sequence DNA.

56. A method for detecting nucleic acid molecules, the method comprising a DNA ligation operation and an amplification operation, wherein the DNA ligation operation comprises circularization of an open circle probe, wherein circularization of the open circle probe is dependent on hybridization of the open circle probe to a target sequence, wherein the target sequence is coupled to a specific binding molecule, wherein the specific binding molecule can interact with a target molecule, wherein the target molecule is a nucleic acid molecule, wherein the amplification operation comprises rolling circle replication of the circularized open circle probe to produce tandem sequence DNA.

57. The method of claim 56 wherein the specific binding molecule is bound to a target molecule.

58. The method of claim 56 wherein the method includes a step of bringing the specific binding molecule into contact with the target molecule.

59. The method of claim 56 wherein the amplification operation produces tandem sequence DNA and secondary tandem sequence DNA, wherein the method further comprises detecting the tandem sequence DNA, the secondary tandem sequence DNA, or both.

60. The method of claim 56 wherein a plurality of different target sequences are used in the amplification operation.

61. The method of claim 60 wherein the rolling circle replication primers are each coupled to a different specific binding molecule.

62. The method of claim 61 wherein the different specific binding molecules each interacts with a different target molecule.

63. A method of detecting nucleic acid molecules, the method comprising, (a) mixing a specific binding molecule with a target sample comprising a target molecule wherein a target sequence is coupled to the specific binding molecule, wherein the specific binding molecule binds to the target molecule, wherein the target molecule is a nucleic acid molecule, (b) mixing an open circle probe with the target sample, to produce an OCP-target sample mixture, and incubating the OCP-target sample mixture under conditions that promote hybridization between the open circle probe and the target sequence in the OCP-target sample mixture, (c) mixing ligase with the OCP-target sample mixture, to produce a ligation mixture, and incubating the ligation mixture under conditions that promote ligation of the open circle probe to form an amplification target circle, (d) mixing a rolling circle replication primer with the ligation mixture, to produce a primer-ATC mixture, and incubating the primer-ATC mixture under conditions that promote hybridization between the amplification target circle and the rolling circle replication primer in the primer-ATC mixture, and (e) mixing DNA polymerase with the primer-ATC mixture, to produce a polymerase-ATC mixture, and incubating the polymerase-ATC mixture under conditions that promote replication of the amplification target circle, wherein replication of the amplification target circle results in the formation of tandem sequence DNA.

64. A method comprising an amplification operation, wherein a nucleic acid tag is coupled to a specific binding molecule, wherein the specific binding molecule can interact with a target molecule, wherein the target molecule is a nucleic acid molecule, wherein the amplification operation comprises rolling circle replication of an amplification target circle to produce tandem sequence DNA.

65. The method of claim 64 wherein the specific binding molecule is bound to a target molecule.

66. The method of claim 64 further comprising bringing the specific binding molecule into contact with the target molecule.

67. The method of claim 64 wherein the method includes a step of bringing the specific binding molecule into contact with the target molecule.

68. A method of detecting target molecules, the method comprising, (a) mixing a rolling circle replication primer with an amplification target circle, to produce a primer-ATC mixture, and incubating the primer-ATC mixture under conditions that promote hybridization between the amplification target circle and the rolling circle replication primer in the primer-ATC mixture, wherein the amplification target circle comprises a single-stranded, circular DNA molecule comprising a primer complement portion, wherein the primer complement portion is complementary to the rolling circle replication primer, wherein the rolling circle replication primer is coupled to a specific binding molecule, and (b) mixing DNA polymerase with the primer-ATC mixture, to produce a polymerase-ATC mixture, and incubating the polymerase-ATC mixture under conditions that promote replication of the amplification target circle, wherein replication of the amplification target circle results in the formation of tandem sequence DNA, (c) mixing the specific binding molecule with a target sample comprising a target molecule, wherein the specific binding molecule binds to the target molecule.

69. The method of claim 68 wherein the target molecule is a nucleic acid molecule, wherein the specific binding molecule is an oligonucleotide complementary to a nucleotide sequence in the nucleic acid molecule.

70. The method of claim 68 wherein the target molecule is a protein.

* * * * *